United States Patent
Drews et al.

(10) Patent No.: US 8,979,882 B2
(45) Date of Patent: Mar. 17, 2015

(54) DEVICES, METHODS, AND KITS FOR FORMING TRACTS IN TISSUE

(75) Inventors: Michael Drews, Palo Alto, CA (US); D. Bruce Modesitt, San Carlos, CA (US)

(73) Assignee: Arstasis, Inc., Fremont, CA (US)

( * ) Notice: Subject to any disclaimer, the term of this patent is extended or adjusted under 35 U.S.C. 154(b) by 499 days.

(21) Appl. No.: 12/507,038

(22) Filed: Jul. 21, 2009

(65) Prior Publication Data
US 2010/0016786 A1    Jan. 21, 2010

Related U.S. Application Data

(60) Provisional application No. 61/082,449, filed on Jul. 21, 2008.

(51) Int. Cl.
A61B 17/34    (2006.01)
A61B 17/00    (2006.01)
(Continued)

(52) U.S. Cl.
CPC ......... *A61B 17/3415* (2013.01); *A61B 17/3478* (2013.01); *A61B 2017/00247* (2013.01); *A61B 2017/00278* (2013.01); *A61B 2017/003* (2013.01); *A61B 2017/2927* (2013.01); *A61B 2017/308* (2013.01); *A61B 2017/3488* (2013.01); *A61B 2018/00392* (2013.01); *A61B 2019/464* (2013.01); *A61B 2217/005* (2013.01); *A61M 1/008* (2013.01)
USPC .......................................... 606/185; 600/201

(58) Field of Classification Search
USPC .............. 606/79, 167, 185, 213; 604/22, 272; 600/201
See application file for complete search history.

(56) References Cited

U.S. PATENT DOCUMENTS

| 2,857,925 A | 10/1957 | Higginbottom |
| 3,727,614 A | 4/1973 | Kniazuk |

(Continued)

FOREIGN PATENT DOCUMENTS

| EP | 0637431 | 2/1995 |
| EP | 0910288 B1 | 8/2002 |

(Continued)

OTHER PUBLICATIONS

Non-final office action dated May 28, 2011, for related U.S. Appl. No. 12/467,251, Inventor D. Bruce Modesitt, filed May 15, 2009, (11 pages).

(Continued)

*Primary Examiner* — Victor Nguyen
(74) *Attorney, Agent, or Firm* — David C. Lundmark

(57) ABSTRACT

Described here are methods and devices for forming tracts in tissue. Some of the devices feature an elongate member, a suction member coupled to a distal portion of the elongate member, and a tissue-piercing member slidably housed within the elongate member for forming a tract in tissue. Other devices feature more than one suction member. Methods for forming tracts in tissue are also described here. In some methods, a device is advanced adjacent tissue, where the device features one or more suction members and a tissue-piercing member. Suction is applied so that the tissue is drawn against the one or more suction members, and a tissue-piercing member is advanced in a first direction through the drawn tissue to form a tract in or through the tissue. Kits incorporating one or more of the devices described here, in conjunction with one or more tools or the like, are also described here.

14 Claims, 45 Drawing Sheets

(51) Int. Cl.
   *A61B 17/29* (2006.01)
   *A61B 17/30* (2006.01)
   *A61B 18/00* (2006.01)
   *A61B 19/00* (2006.01)
   *A61M 1/00* (2006.01)

(56) References Cited

U.S. PATENT DOCUMENTS

| | | |
|---|---|---|
| 3,730,185 A | 5/1973 | Cook et al. |
| 4,006,747 A | 2/1977 | Kronenthal et al. |
| 4,744,364 A | 5/1988 | Kensey |
| 4,774,949 A | 10/1988 | Fogarty |
| 4,850,960 A | 7/1989 | Grayzel |
| 4,890,611 A | 1/1990 | Monfort et al. |
| 4,921,484 A | 5/1990 | Hillstead |
| 4,955,897 A | 9/1990 | Ship |
| 4,962,755 A | 10/1990 | King et al. |
| 5,183,464 A | 2/1993 | Dubrul et al. |
| 5,271,415 A | 12/1993 | Foerster et al. |
| 5,304,184 A | 4/1994 | Hathaway et al. |
| 5,336,221 A | 8/1994 | Anderson |
| 5,358,507 A | 10/1994 | Daily |
| 5,364,389 A | 11/1994 | Anderson |
| 5,368,601 A | 11/1994 | Sauer et al. |
| 5,380,290 A | 1/1995 | Makower et al. |
| 5,383,897 A | 1/1995 | Wholey |
| 5,391,182 A | 2/1995 | Chin |
| 5,391,183 A | 2/1995 | Janzen et al. |
| 5,403,329 A | 4/1995 | Hinchcliffe |
| 5,415,657 A | 5/1995 | Taymor-Luria |
| 5,417,699 A | 5/1995 | Klein et al. |
| 5,437,665 A | 8/1995 | Munro |
| 5,439,469 A | 8/1995 | Heaven et al. |
| 5,451,230 A | 9/1995 | Steinert |
| 5,462,561 A | 10/1995 | Voda |
| 5,467,786 A | 11/1995 | Allen et al. |
| 5,470,338 A | 11/1995 | Whitfield et al. |
| 5,474,568 A | 12/1995 | Scott |
| 5,476,470 A | 12/1995 | Fitzgibbons, Jr. |
| 5,489,288 A | 2/1996 | Buelna |
| 5,496,332 A | 3/1996 | Sierra et al. |
| 5,496,334 A | 3/1996 | Klundt et al. |
| 5,503,634 A | 4/1996 | Christy |
| 5,507,744 A | 4/1996 | Tay et al. |
| 5,527,321 A | 6/1996 | Hinchliffe |
| 5,527,322 A | 6/1996 | Klein et al. |
| 5,536,255 A | 7/1996 | Moss |
| 5,571,169 A | 11/1996 | Plaia et al. |
| 5,613,974 A | 3/1997 | Andreas et al. |
| 5,620,461 A | 4/1997 | Muijs Van De Moer et al. |
| 5,622,188 A | 4/1997 | Plaia et al. |
| 5,645,566 A | 7/1997 | Brenneman et al. |
| 5,653,717 A | 8/1997 | Ko et al. |
| 5,695,504 A | 12/1997 | Gifford, III et al. |
| 5,700,273 A | 12/1997 | Buelna et al. |
| 5,709,224 A | 1/1998 | Behl et al. |
| 5,746,755 A | 5/1998 | Wood et al. |
| 5,749,858 A | 5/1998 | Cramer |
| 5,758,665 A | 6/1998 | Suval |
| 5,762,066 A | 6/1998 | Law et al. |
| 5,766,183 A | 6/1998 | Sauer |
| 5,772,673 A | 6/1998 | Cuny et al. |
| 5,779,719 A | 7/1998 | Klein et al. |
| 5,792,152 A | 8/1998 | Klein et al. |
| 5,797,929 A | 8/1998 | Andreas et al. |
| 5,810,810 A | 9/1998 | Tay et al. |
| 5,810,882 A | 9/1998 | Bolduc et al. |
| 5,817,108 A | 10/1998 | Poncet |
| 5,830,232 A | 11/1998 | Hasson |
| 5,836,955 A | 11/1998 | Buelna et al. |
| 5,846,253 A | 12/1998 | Buelna et al. |
| 5,860,990 A | 1/1999 | Nobles et al. |
| 5,860,991 A | 1/1999 | Klein et al. |
| 5,868,762 A | 2/1999 | Cragg et al. |
| 5,882,302 A | 3/1999 | Driscoll, Jr. et al. |
| 5,902,311 A | 5/1999 | Andreas et al. |
| 5,921,994 A | 7/1999 | Andreas et al. |
| 5,928,246 A | 7/1999 | Gordon et al. |
| 5,941,897 A | 8/1999 | Myers |
| 5,954,732 A | 9/1999 | Hart et al. |
| 5,972,005 A | 10/1999 | Stalker et al. |
| 5,972,013 A | 10/1999 | Schmidt |
| 5,980,539 A | 11/1999 | Kontos |
| 5,984,917 A | 11/1999 | Fleischman et al. |
| 5,984,948 A | 11/1999 | Hasson |
| 5,984,950 A | 11/1999 | Cragg et al. |
| 6,010,514 A | 1/2000 | Burney et al. |
| 6,033,401 A | 3/2000 | Edwards et al. |
| 6,036,699 A | 3/2000 | Andreas et al. |
| 6,036,721 A | 3/2000 | Harren et al. |
| 6,042,601 A | 3/2000 | Smith |
| 6,063,085 A | 5/2000 | Tay et al. |
| 6,071,292 A | 6/2000 | Makower et al. |
| 6,071,300 A | 6/2000 | Brenneman et al. |
| 6,077,276 A | 6/2000 | Kontos |
| 6,080,175 A | 6/2000 | Hogendijk |
| 6,093,173 A | 7/2000 | Balceta et al. |
| 6,117,144 A | 9/2000 | Nobles et al. |
| 6,117,145 A | 9/2000 | Wood et al. |
| 6,136,010 A | 10/2000 | Modesitt et al. |
| 6,139,560 A | 10/2000 | Kremer |
| 6,143,004 A | 11/2000 | Davis et al. |
| 6,146,397 A | 11/2000 | Harkrider, Jr. |
| 6,152,918 A * | 11/2000 | Padilla et al. .................. 606/15 |
| 6,159,232 A | 12/2000 | Nowakowski |
| 6,171,317 B1 | 1/2001 | Jackson et al. |
| 6,179,832 B1 | 1/2001 | Jones et al. |
| 6,190,396 B1 | 2/2001 | Whitin et al. |
| 6,197,042 B1 | 3/2001 | Ginn et al. |
| 6,203,554 B1 | 3/2001 | Roberts |
| 6,206,893 B1 | 3/2001 | Klein et al. |
| 6,206,895 B1 | 3/2001 | Levinson |
| 6,245,079 B1 | 6/2001 | Nobles et al. |
| 6,258,084 B1 | 7/2001 | Goldman et al. |
| 6,302,898 B1 | 10/2001 | Edwards et al. |
| 6,358,244 B1 | 3/2002 | Newman et al. |
| 6,358,556 B1 | 3/2002 | Ding et al. |
| 6,371,975 B2 | 4/2002 | Cruise et al. |
| 6,383,208 B1 | 5/2002 | Sancoff et al. |
| 6,395,015 B1 | 5/2002 | Borst et al. |
| 6,398,782 B1 | 6/2002 | Pecor et al. |
| 6,454,777 B1 | 9/2002 | Green |
| 6,457,182 B1 | 10/2002 | Szczesuil et al. |
| 6,458,147 B1 | 10/2002 | Cruise et al. |
| 6,461,383 B1 | 10/2002 | Gesswein et al. |
| 6,468,228 B1 | 10/2002 | Topel et al. |
| 6,475,182 B1 | 11/2002 | Hnojewyj et al. |
| 6,506,210 B1 | 1/2003 | Kanner |
| 6,517,553 B2 | 2/2003 | Klein et al. |
| 6,524,321 B2 | 2/2003 | Kanesaka |
| 6,524,326 B1 | 2/2003 | Zhu et al. |
| 6,533,795 B1 | 3/2003 | Tran et al. |
| 6,562,059 B2 | 5/2003 | Edwards et al. |
| 6,565,583 B1 | 5/2003 | Deaton et al. |
| 6,569,012 B2 | 5/2003 | Lydon et al. |
| 6,622,731 B2 | 9/2003 | Daniel et al. |
| 6,623,510 B2 | 9/2003 | Carley et al. |
| 6,626,855 B1 | 9/2003 | Weng et al. |
| 6,641,592 B1 | 11/2003 | Sauer et al. |
| 6,656,136 B1 | 12/2003 | Weng et al. |
| 6,663,655 B2 | 12/2003 | Ginn et al. |
| 6,676,685 B2 | 1/2004 | Pedros et al. |
| 6,682,489 B2 | 1/2004 | Tenerz et al. |
| 6,689,152 B2 | 2/2004 | Balceta et al. |
| 6,719,694 B2 | 4/2004 | Weng et al. |
| 6,719,750 B2 | 4/2004 | Varner et al. |
| 6,733,515 B1 | 5/2004 | Edwards et al. |
| 6,743,195 B2 | 6/2004 | Zucker |
| 6,749,621 B2 | 6/2004 | Pantages et al. |
| 6,749,622 B2 | 6/2004 | McGuckin, Jr. et al. |
| 6,767,356 B2 | 7/2004 | Kanner et al. |
| 6,773,699 B1 | 8/2004 | Soltz et al. |
| 6,780,197 B2 | 8/2004 | Roe et al. |
| 6,790,220 B2 | 9/2004 | Morris et al. |

(56) References Cited

U.S. PATENT DOCUMENTS

| | | | |
|---|---|---|---|
| 6,802,822 B1 | 10/2004 | Dodge | |
| 6,818,008 B1 | 11/2004 | Cates et al. | |
| 6,840,952 B2 | 1/2005 | Saker et al. | |
| 6,843,792 B2 | 1/2005 | Nishtala et al. | |
| 6,846,319 B2 | 1/2005 | Ginn et al. | |
| 6,846,320 B2 | 1/2005 | Ashby et al. | |
| 6,846,321 B2 | 1/2005 | Zucker | |
| 6,860,895 B1 | 3/2005 | Akerfeldt et al. | |
| 6,863,680 B2 | 3/2005 | Ashby | |
| 6,890,342 B2 | 5/2005 | Zhu et al. | |
| 6,890,343 B2 | 5/2005 | Ginn et al. | |
| 6,890,344 B2 | 5/2005 | Levinson | |
| 6,893,431 B2 | 5/2005 | Naimark et al. | |
| 6,896,692 B2 | 5/2005 | Ginn et al. | |
| 6,918,890 B2 * | 7/2005 | Schmidt | 604/164.01 |
| 6,929,655 B2 | 8/2005 | Egnelöv et al. | |
| 6,936,053 B1 | 8/2005 | Weiss | |
| 6,939,348 B2 | 9/2005 | Malecki et al. | |
| 6,939,357 B2 | 9/2005 | Navarro et al. | |
| 6,939,363 B2 | 9/2005 | Åkerfeldt | |
| 6,939,364 B1 | 9/2005 | Soltz et al. | |
| 6,942,674 B2 | 9/2005 | Belef et al. | |
| 6,949,080 B2 | 9/2005 | Wolf et al. | |
| 6,949,107 B2 | 9/2005 | McGuckin, Jr. et al. | |
| 6,949,114 B2 | 9/2005 | Milo et al. | |
| 6,964,668 B2 | 11/2005 | Modesitt et al. | |
| 6,969,397 B2 | 11/2005 | Ginn | |
| 6,981,983 B1 | 1/2006 | Rosenblatt et al. | |
| 6,994,686 B2 | 2/2006 | Cruise et al. | |
| 7,001,400 B1 | 2/2006 | Modesitt et al. | |
| 7,008,440 B2 | 3/2006 | Sing et al. | |
| 7,008,442 B2 | 3/2006 | Brightbill | |
| 7,025,746 B2 | 4/2006 | Tal | |
| 7,025,776 B1 | 4/2006 | Houser et al. | |
| 7,029,489 B1 | 4/2006 | Ashby et al. | |
| 7,037,322 B1 | 5/2006 | Sing et al. | |
| 7,037,323 B2 | 5/2006 | Sing et al. | |
| 7,041,119 B2 | 5/2006 | Green | |
| 7,074,232 B2 | 7/2006 | Kanner et al. | |
| 7,077,848 B1 | 7/2006 | de Juan, Jr. et al. | |
| 7,081,125 B2 | 7/2006 | Edwards et al. | |
| 7,083,628 B2 | 8/2006 | Bachman | |
| 7,141,055 B2 | 11/2006 | Abrams et al. | |
| 7,175,646 B2 | 2/2007 | Brenneman | |
| 7,179,270 B2 | 2/2007 | Makower | |
| 7,182,763 B2 | 2/2007 | Nardella | |
| 7,186,251 B2 | 3/2007 | Malecki et al. | |
| 7,226,467 B2 | 6/2007 | Lucatero et al. | |
| 7,235,087 B2 | 6/2007 | Modesitt et al. | |
| 7,247,162 B1 | 7/2007 | Thornton | |
| 7,250,028 B2 | 7/2007 | Julian et al. | |
| 7,279,001 B2 | 10/2007 | Addis et al. | |
| 7,291,159 B2 | 11/2007 | Schmelzeisen-Redeker et al. | |
| 7,316,704 B2 | 1/2008 | Bagaoisan et al. | |
| 7,322,976 B2 | 1/2008 | Yassinzadeh | |
| 7,335,220 B2 | 2/2008 | Khosravi et al. | |
| 7,361,180 B2 | 4/2008 | Saadat et al. | |
| 7,361,183 B2 | 4/2008 | Ginn | |
| 7,377,927 B2 | 5/2008 | Burdulis et al. | |
| 7,381,210 B2 | 6/2008 | Zarbatany et al. | |
| 7,390,328 B2 | 6/2008 | Modesitt | |
| 7,390,329 B2 | 6/2008 | Westra et al. | |
| 7,470,237 B2 | 12/2008 | Beckman et al. | |
| 7,494,460 B2 | 2/2009 | Haarstad et al. | |
| 7,572,274 B2 | 8/2009 | Yassinzadeh | |
| 7,597,705 B2 | 10/2009 | Forsberg et al. | |
| 7,609,673 B2 | 10/2009 | Bergenlid et al. | |
| 7,621,925 B2 | 11/2009 | Saadat et al. | |
| 7,621,936 B2 | 11/2009 | Cragg et al. | |
| 7,635,329 B2 | 12/2009 | Goldfarb et al. | |
| 7,648,517 B2 | 1/2010 | Makower et al. | |
| 7,662,128 B2 | 2/2010 | Salcudean et al. | |
| 7,678,133 B2 | 3/2010 | Modesitt | |
| 7,704,261 B2 | 4/2010 | Sakamoto et al. | |
| 7,704,264 B2 | 4/2010 | Ewers et al. | |
| 7,731,726 B2 | 6/2010 | Belhe et al. | |
| 7,736,347 B2 | 6/2010 | Kaplan | |
| 7,762,977 B2 | 7/2010 | Porter et al. | |
| 7,837,696 B2 | 11/2010 | Modesitt | |
| 7,842,047 B2 | 11/2010 | Modesitt | |
| 7,846,170 B2 | 12/2010 | Modesitt et al. | |
| 7,850,654 B2 | 12/2010 | Belhe et al. | |
| 7,850,701 B2 | 12/2010 | Modesitt et al. | |
| 7,867,249 B2 | 1/2011 | Palermo et al. | |
| 7,875,052 B2 | 1/2011 | Kawaura et al. | |
| 7,967,839 B2 | 6/2011 | Flock et al. | |
| 2001/0031922 A1 | 10/2001 | Weng et al. | |
| 2001/0047165 A1 | 11/2001 | Makower et al. | |
| 2002/0016614 A1 | 2/2002 | Klein et al. | |
| 2002/0062146 A1 | 5/2002 | Makower et al. | |
| 2002/0156495 A1 | 10/2002 | Brenneman et al. | |
| 2003/0093093 A1 | 5/2003 | Modesitt et al. | |
| 2003/0100921 A1 | 5/2003 | Addis et al. | |
| 2003/0144679 A1 | 7/2003 | Irisawa | |
| 2003/0158578 A1 | 8/2003 | Pantages et al. | |
| 2003/0233120 A1 | 12/2003 | Akerfeldt | |
| 2003/0236542 A1 | 12/2003 | Makower | |
| 2004/0044350 A1 | 3/2004 | Martin et al. | |
| 2004/0068242 A1 | 4/2004 | McGuckin | |
| 2004/0086951 A1 | 5/2004 | Archakov et al. | |
| 2004/0092964 A1 | 5/2004 | Modesitt et al. | |
| 2004/0093024 A1 | 5/2004 | Lousararian et al. | |
| 2004/0097978 A1 | 5/2004 | Modesitt et al. | |
| 2004/0122449 A1 | 6/2004 | Modesitt et al. | |
| 2004/0138522 A1 | 7/2004 | Haarstad et al. | |
| 2004/0143290 A1 | 7/2004 | Brightbill | |
| 2004/0153123 A1 | 8/2004 | Palermo et al. | |
| 2004/0158287 A1 | 8/2004 | Cragg et al. | |
| 2004/0172058 A1 | 9/2004 | Edwards et al. | |
| 2004/0176758 A1 | 9/2004 | Yassinzadeh | |
| 2004/0215232 A1 | 10/2004 | Belhe et al. | |
| 2004/0215233 A1 | 10/2004 | Kaplan et al. | |
| 2004/0220594 A1 | 11/2004 | de Canniere | |
| 2004/0220604 A1 | 11/2004 | Fogarty et al. | |
| 2004/0267307 A1 | 12/2004 | Bagaoisan et al. | |
| 2004/0267308 A1 | 12/2004 | Bagaoisan et al. | |
| 2005/0033361 A1 | 2/2005 | Galdonik et al. | |
| 2005/0049634 A1 | 3/2005 | Chopra | |
| 2005/0075653 A1 | 4/2005 | Saadat et al. | |
| 2005/0085773 A1 | 4/2005 | Forsberg | |
| 2005/0085851 A1 | 4/2005 | Fiehler et al. | |
| 2005/0085852 A1 | 4/2005 | Ditter | |
| 2005/0085854 A1 | 4/2005 | Ginn | |
| 2005/0085855 A1 | 4/2005 | Forsberg | |
| 2005/0085856 A1 | 4/2005 | Ginn | |
| 2005/0090860 A1 | 4/2005 | Paprocki | |
| 2005/0096697 A1 | 5/2005 | Forsberg et al. | |
| 2005/0107826 A1 | 5/2005 | Zhu et al. | |
| 2005/0125030 A1 | 6/2005 | Forsberg et al. | |
| 2005/0143761 A1 | 6/2005 | Modesitt et al. | |
| 2005/0149049 A1 | 7/2005 | Assell et al. | |
| 2005/0149065 A1 | 7/2005 | Modesitt | |
| 2005/0228443 A1 | 10/2005 | Yassinzadeh | |
| 2005/0234507 A1 | 10/2005 | Geske et al. | |
| 2005/0251189 A1 | 11/2005 | Saadat et al. | |
| 2005/0267520 A1 * | 12/2005 | Modesitt | 606/213 |
| 2005/0267522 A1 | 12/2005 | Yassinzadeh et al. | |
| 2005/0277967 A1 | 12/2005 | Brenneman et al. | |
| 2005/0277980 A1 | 12/2005 | Yassinzadeh | |
| 2006/0009802 A1 | 1/2006 | Modesitt | |
| 2006/0036218 A1 | 2/2006 | Goodson, IV et al. | |
| 2006/0064101 A1 | 3/2006 | Arramon | |
| 2006/0064159 A1 | 3/2006 | Porter et al. | |
| 2006/0069396 A1 | 3/2006 | Meade et al. | |
| 2006/0079914 A1 | 4/2006 | Modesitt et al. | |
| 2006/0111741 A1 | 5/2006 | Nardella | |
| 2006/0129101 A1 | 6/2006 | McGuckin, Jr. et al. | |
| 2006/0135990 A1 | 6/2006 | Johnson | |
| 2006/0135991 A1 | 6/2006 | Kawaura et al. | |
| 2006/0136035 A1 | 6/2006 | Hermann et al. | |
| 2006/0142785 A1 | 6/2006 | Modesitt et al. | |
| 2006/0167476 A1 | 7/2006 | Burdulis, Jr. et al. | |
| 2006/0206125 A1 | 9/2006 | Fogarty et al. | |
| 2006/0235449 A1 | 10/2006 | Schubart et al. | |

(56) References Cited

U.S. PATENT DOCUMENTS

| | | |
|---|---|---|
| 2006/0259017 A1 | 11/2006 | Heil, Jr. |
| 2006/0264975 A1 | 11/2006 | Pipenhagen et al. |
| 2006/0271078 A1 | 11/2006 | Modesitt |
| 2007/0027454 A1 | 2/2007 | Modesitt |
| 2007/0027455 A1 | 2/2007 | Modesitt |
| 2007/0032802 A1 | 2/2007 | Modesitt |
| 2007/0032803 A1 | 2/2007 | Modesitt |
| 2007/0032804 A1 | 2/2007 | Modesitt |
| 2007/0106246 A1 | 5/2007 | Modesitt |
| 2007/0167959 A1 | 7/2007 | Modesitt et al. |
| 2007/0255313 A1 | 11/2007 | Modesitt |
| 2008/0097347 A1 | 4/2008 | Arvanaghi |
| 2008/0114364 A1* | 5/2008 | Goldin et al. .................... 606/79 |
| 2009/0105744 A1 | 4/2009 | Modesitt et al. |
| 2009/0312786 A1 | 12/2009 | Trask et al. |
| 2009/0318889 A1 | 12/2009 | Modesitt |
| 2010/0016786 A1 | 1/2010 | Drews et al. |
| 2010/0016810 A1 | 1/2010 | Drews et al. |
| 2010/0063375 A1* | 3/2010 | Kassab et al. ................. 600/375 |
| 2010/0125296 A1 | 5/2010 | Modesitt |
| 2011/0125178 A1 | 5/2011 | Drews et al. |
| 2011/0208215 A1 | 8/2011 | Modesitt et al. |
| 2011/0230906 A1 | 9/2011 | Modesitt et al. |

FOREIGN PATENT DOCUMENTS

| | | |
|---|---|---|
| JP | 2002-330973 | 11/2002 |
| JP | 2003-126024 | 5/2003 |
| WO | 01/12102 | 2/2001 |
| WO | 01/66018 | 9/2001 |
| WO | WO-03/082363 A1 | 10/2003 |
| WO | WO-2005/112791 A2 | 12/2005 |
| WO | WO-2005/112791 A3 | 12/2005 |
| WO | WO-2006/017023 A2 | 2/2006 |
| WO | WO-2006/017023 A3 | 2/2006 |
| WO | WO-2006/124896 A2 | 11/2006 |
| WO | WO-2006/124896 A3 | 11/2006 |
| WO | WO 2008/042034 A2 | 4/2008 |
| WO | WO 2008/042034 A3 | 4/2008 |
| WO | WO 2008/070238 A2 | 6/2008 |
| WO | WO 2008/070238 A3 | 6/2008 |
| WO | WO-2008/097955 A1 | 8/2008 |

OTHER PUBLICATIONS

Office action for related AU Patent Application No. 2006247355, dated Mar. 16, 2011, (16 pages).
International Search Report mailed on Nov. 6, 2009, for PCT Application No. PCT/US2009/51320, filed on Jul. 21, 2009, six pages.
Written Opinion mailed on Nov. 6, 2009, for PCT Application No. PCT/US2009/51320, filed on Jul. 21, 2009, six pages.
Final Office Action mailed Dec. 8, 2009, for U.S. Appl. No. 11/544,149, filed Oct. 6, 2006, 9 pages.
Final Office Action mailed on Nov. 27, 2009, for U.S. Appl. No. 11/544,196, filed Oct. 6, 2006, 6 pages.
Final Office Action mailed on Nov. 25, 2009, for U.S. Appl. No. 11/544,177, filed Oct. 6, 2006, 8 pages.
Final Office Action mailed on Nov. 25, 2009, for U.S. Appl. No. 11/545,272, filed Oct. 6, 2006, 6 pages.
Non-Final Office Action mailed on Apr. 15, 2010, for U.S. Appl. No. 11/432,982, filed May 12, 2006, eight pages.
Notice of Allowance mailed on Nov. 3, 2009, for U.S. Appl. No. 10/888,682, filed Jul. 10, 2004, nine pages.
European Search Report mailed on Jun. 26, 2009, for EP Patent Application No. 08011884.7, filed on May 12, 2005, five pages.
Final Office Action mailed on Nov. 18, 2009, for U.S. Appl. No. 11/544,365, filed Oct. 6, 2006, six pages.
Final Office Action mailed on Aug. 21, 2009, for U.S. Appl. No. 11/788,509, filed Apr. 19, 2007, ten pages.
Final Office Action mailed on Aug. 14, 2009, for U.S. Appl. No. 11/544,317, filed Oct. 6, 2006, eight pages.
Final Office Action mailed on Jul. 6, 2009, for U.S. Appl. No. 10/844,247, filed May 12, 2004, nine pages.
Final Office Action mailed on Jun. 11, 2009, for U.S. Appl. No. 11/432,982, filed May 12, 2006, seven pages.
Final Office Action mailed on May 6, 2009, for U.S. Appl. No. 10/888,682, filed Jul. 10, 2004, eight pages.
Franklin, I.J. et al. (1999). "Uptake of Tetracycline by Aortic Aneurysm Wall and Its Effect on Inflammation and Proteolysis," *Brit. J. Surgery* 86(6):771-775.
International Preliminary Report on Patentability mailed on Mar. 5, 2009, for PCT Application No. PCT/US2005/016623, filed on May 12, 2005, five pages.
International Preliminary Report on Patentability mailed on Mar. 3, 2009, for PCT Application No. PCT/US2005/023107, filed on Jun. 30, 2005, five pages.
International Preliminary Report on Patentability mailed on Nov. 14, 2007, for PCT Application No. PCT/US2006/018915, filed on May 12, 2006, five pages.
International Search Report mailed Aug. 20, 2007, for PCT Application No. PCT/US06/18915, filed on May 12, 2006, three pages.
International Search Report mailed on Jun. 5, 2008, for PCT Application No. PCT/US05/23107, filed on Jun. 30, 2005, two pages.
International Search Report mailed on Aug. 8, 2008, for PCT Application No. PCT/US05/16623, filed on May 12, 2005, three pages.
International Search Report mailed on Sep. 3, 2009, for PCT Application No. PCT/US2009/051317, filed on Jul. 21, 2009, three pages.
Invitation to Pay Additional Fees mailed on Sep. 10, 2009, for PCT Application No. PCT/US09/51320, filed on Jul. 21, 2009, two pages.
Non-Final Office Action mailed on Jul. 31, 2008, for U.S. Appl. No. 10/888,682, filed Jul. 10, 2004, twelve pages.
Non-Final Office Action mailed on Oct. 8, 2008, for U.S. Appl. No. 11/432,982, filed May 12, 2006, seven pages.
Non-Final Office Action mailed on Oct. 29, 2008, for U.S. Appl. No. 11/788,509, filed Apr. 19, 2007, eight pages.
Non-Final Office Action mailed on Nov. 12, 2008, for U.S. Appl. No. 10/844,247, filed May 12, 2004, nine pages.
Non-Final Office Action mailed on Jan. 9, 2009, for U.S. Appl. No. 11/544,317, filed Oct. 6, 2006, eleven pages.
Non-Final Office Action mailed on Feb. 18, 2009, for U.S. Appl. No. 11/544,149, filed Oct. 6, 2006, eight pages.
Non-Final Office Action mailed on Feb. 18, 2009, for U.S. Appl. No. 11/545,272, filed Oct. 6, 2006, seven pages.
Non-Final Office Action mailed on Feb. 23, 2009, for U.S. Appl. No. 11/544,196, filed Oct. 6, 2006, seven pages.
Non-Final Office Action mailed on Feb. 23, 2009, for U.S. Appl. No. 11/544,365, filed Oct. 6, 2006, six pages.
Non-Final Office Action mailed on Feb. 24, 2009, for U.S. Appl. No. 11/544,177, filed Oct. 6, 2006, seven pages.
Pyo, R. et al. (Jun. 2000). "Targeted Gene Disruption of Matrix Metalloproteinase-9 (Gelatinase B) Suppresses Development of Experimental Abdominal Aortic Aneurysms," *J. Clinical Investigation* 105(11):1641-1649.
Tambiah, J. et al. (2001). "Provocation of Experimental Aortic Inflammation and Dilatation by Inflammatory Mediators and *Chlamydia pneumoniae*," *Brit. J. Surgery* 88(7):935-940.
Walton, L.J. et al. (Jul. 6, 1999). "Inhibition of Prostaglandin $E_2$ Synthesis in Abdominal Aortic Aneurysms," *Circulation* 100:48-54.
Written Opinion mailed on Aug. 20, 2007, for PCT Application No. PCT/US06/18915, filed May 12, 2006, four pages.
Written Opinion mailed on Jun. 5, 2008, for PCT Application No. PCT/US05/23107, filed on Jun. 30, 2005, four pages.
Written Opinion mailed on Aug. 8, 2008, for PCT Application No. PCT/US05/16623, filed on May 12, 2005, three pages.
Written Opinion mailed on Sep. 3, 2009, for PCT Application No. PCT/US2009/051317, filed on Jul. 21, 2009, seven pages.
Xu, Q. et al. (Aug. 11, 2000). "Sp1 Increases Expression of Cyclooxygenase-2 in Hypoxic Vascular Endothelium," *J. Biological Chemistry* 275(32):24583-24589.
File history for related U.S. Appl. No. 10/844,247, filed May 12, 2004, Inventor D. Bruce Modesitt, including (211 pages total): Amendment Response to Final Office Action mailed Jul. 6, 2009, for U.S. Appl. No. 10/844,247, submitted on Dec. 7, 2009; Examiner Interview Summary Record for U.S. Appl. No. 10/844,247, mailed

(56) References Cited

OTHER PUBLICATIONS

Sep. 30, 2009; Final Office Action for U.S. Appl. No. 10/844,247, mailed Jul. 6, 2009; Applicant Arguments/Remarks Made in an Amendment in Response to Examiner Interview Summary Record mailed Mar. 24, 2009, for U.S. Appl. No. 10/844,247, submitted on Apr. 9, 2009; Examiner Interview Summary Record for U.S. Appl. No. 10/844,247, mailed Mar. 24, 2009; Amendment Response to Non Final Office Action mailed Nov. 12, 2008, for U.S. Appl. No. 10/844,247, submitted on Mar. 12, 2009; Non Final Office Action for U.S. Appl. No. 10/844,247, mailed Nov. 12, 2008; Response to Election/Restriction mailed Jun. 16, 2008 for U.S. Appl. No. 10/844,247, submitted on Jul. 16, 2008; Requirement for Restriction/Election for U.S. Appl. No. 10/844,247, mailed Jun. 16, 2008; Examiner Interview Summary Record for U.S. Appl. No. 10/844,247, mailed Oct. 9, 2007; Amendment Response to Final Office Action mailed Jun. 28, 2007, for U.S. Appl. No. 10/844,247, submitted on Sep. 27, 2007; Final Office Action for U.S. Appl. No. 10/844,247, mailed Jun. 28, 2007; Amendment Response to Non Final Office Action mailed Jan. 4, 2007, for U.S. Appl. No. 10/844,247, submitted on Apr. 4, 2007; Non Final Office Action for U.S. Appl. No. 10/844,247, mailed Jan. 4, 2007; Response to Election/Restriction mailed Sep. 28, 2006 for U.S. Appl. No. 10/844,247, submitted on Oct. 31, 2006; Requirement for Restriction/Election for U.S. Appl. No. 10/844,247, mailed Sep. 28, 2006; Application for U.S. Appl. No. 10/844,247, filed May 12, 2004.

File history for related U.S. Appl. No. 11/544,196, filed Oct. 6, 2006, Inventor D. Bruce Modesitt, including (126 pages total): Terminal Disclaimer for U.S. Appl. No. 11/544,196, submitted Mar. 18, 2011; Amendment Response to Non Final Office Action mailed Jun. 23, 2010, for U.S. Appl. No. 11/544,196, submitted on Dec. 23, 2010; Examiner Interview Summary Record for U.S. Appl. No. 11/544,196, mailed Dec. 16, 2010; Non Final Office Action for U.S. Appl. No. 11/544,196, mailed Jun. 23, 2010; Amendment Response to Final Office Action mailed Nov. 27, 2009, for U.S. Appl. No. 11/544,196, submitted on May 7, 2010; Examiner Interview Summary Record for U.S. Appl. No. 11/544,196, mailed Feb. 16, 2010; Final Office Action for U.S. Appl. No. 11/544,196, mailed Nov. 27, 2009; Examiner Interview Summary Record for U.S. Appl. No. 11/544,196, mailed Aug. 6, 2009; Supplemental Amendment Response to Non Final Office Action mailed Sep. 2, 2003, for U.S. Appl. No. 11/544,196, submitted on Aug. 3, 2009; Amendment Response to Non Final Office Action mailed Sep. 2, 2003, for U.S. Appl. No. 11/544,196, submitted on Jun. 23, 2009; Non Final Office Action for U.S. Appl. No. 11/544,196, mailed Feb. 23, 2009; Preliminary Amendment for U.S. Appl. No. 11/544,196, submitted Oct. 6, 2006; Application for U.S. Appl. No. 11/544,196, filed Oct. 6, 2006.

File history for related U.S. Appl. No. 11/545,272, filed Oct. 6, 2006, Inventor D. Bruce Modesitt, including (154 pages total): Terminal Disclaimer for U.S. Appl. No. 11/545,272, submitted Dec. 23, 2010; Amendment Response to Non Final Office Action mailed Jun. 23, 2010, for U.S. Appl. No. 11/545,272, submitted on Dec. 23, 2010; Examiner Interview Summary Record for U.S. Appl. No. 11/545,272, mailed Dec. 16, 2010; Non Final Office Action for U.S. Appl. No. 11/545,272, mailed Jun. 23, 2010; Amendment Response to Final Office Action mailed Nov. 25, 2009, for U.S. Appl. No. 11/545,272, submitted on May 7, 2010; Examiner Interview Summary Record for U.S. Appl. No. 11/545,272, mailed Feb. 16, 2010; Final Office Action for U.S. Appl. No. 11/545,272, mailed Nov. 25, 2009; Examiner Interview Summary Record for U.S. Appl. No. 11/545,272, mailed Aug. 3, 2009; Supplemental Amendment Response to Non Final Office Action mailed Feb. 18, 2009, for U.S. Appl. No. 11/545,272, submitted on Aug. 3, 2009; Amendment Response to Non Final Office Action mailed Feb. 18, 2009, for U.S. Appl. No. 11/545,272, submitted on Jun. 18, 2009; Non Final Office Action for U.S. Appl. No. 11/545,272, mailed Feb. 18, 2009; Preliminary Amendment for U.S. Appl. No. 11/545,272, submitted Oct. 6, 2006; Application for U.S. Appl. No. 11/545,272, filed Oct. 6, 2006.

File history for related U.S. Appl. No. 11/544,365, filed Oct. 6, 2006, Inventor D. Bruce Modesitt, including (152 pages total): Terminal Disclaimer for U.S. Appl. No. 11/544,365, submitted Dec. 23, 2010; Amendment Response to Non Final Office Action mailed Jun. 25, 2010, for U.S. Appl. No. 11/544,365, submitted on Dec. 23, 2010; Examiner Interview Summary Record for U.S. Appl. No. 11/544,365, mailed Dec. 16, 2010; Non Final Office Action for U.S. Appl. No. 11/544,365, mailed Jun. 25, 2010; Amendment Response to Final Office Action mailed Nov. 18, 2009, for U.S. Appl. No. 11/544,365, submitted on May 7, 2010; Examiner Interview Summary Record for U.S. Appl. No. 11/544,365, mailed Feb. 16, 2010; Final Office Action for U.S. Appl. No. 11/544,365, mailed Nov. 18, 2009; Examiner Interview Summary Record for U.S. Appl. No. 11/544,365, mailed Aug. 6, 2009; Supplemental Amendment Response to Non Final Office Action mailed Feb. 23, 2009, for US U.S. Appl. No. 11/544,365, submitted on Aug. 6, 2009; Amendment Response to Non Final Office Action mailed Feb. 23, 2009, for U.S. Appl. No. 11/544,365, submitted on Jun. 22, 2009; Non Final Office Action for U.S. Appl. No. 11/544,365, mailed Feb. 23, 2009; Preliminary Amendment for U.S. Appl. No. 11/544,365, submitted Oct. 6, 2006; Application for U.S. Appl. No. 11/544,365, filed Oct. 6, 2006.

File history for related U.S. Appl. No. 11/544,177, filed Oct. 6, 2006, Inventor D. Bruce Modesitt, including (167 pages total): Terminal Disclaimer for U.S. Appl. No. 11/544,177, submitted Mar. 18, 2011; Amendment Response to Non Final Office Action mailed Jun. 22, 2010, for U.S. Appl. No. 11/544,177, submitted on Dec. 22, 2010; Terminal Disclaimer for U.S. Appl. No. 11/544,177, submitted Dec. 22, 2011; Non Final Office Action for U.S. Appl. No. 11/544,177, mailed Jun. 22, 2010; Amendment Response to Final Office Action mailed Nov. 25, 2009, for U.S. Appl. No. 11/544,177, submitted on May 7, 2010; Examiner Interview Summary Record for U.S. Appl. No. 11/544,177, mailed Feb. 16, 2010; Final Office Action for U.S. Appl. No. 11/544,177, mailed Nov. 25, 2009; Examiner Interview Summary Record for U.S. Appl. No. 11/544,177, mailed Aug. 6, 2009; Supplemental Amendment Response to Non Final Office Action mailed Feb. 24, 2009, for U.S. Appl. No. 11/544,177, submitted on Aug. 6, 2009; Amendment Response to Non Final Office Action mailed Feb. 24, 2009, for U.S. Appl. No. 11/544,177, submitted on Jun. 24, 2009; Non Final Office Action for U.S. Appl. No. 11/544,177, mailed Feb. 24, 2009; Preliminary Amendment for U.S. Appl. No. 11/544,177, submitted Oct. 6, 2006; Application for U.S. Appl. No. 11/544,177, filed Oct. 6, 2006.

File history for related U.S. Appl. No. 11/544,149, filed Oct. 6, 2006, Inventor D. Bruce Modesitt, including (170 pages total): Terminal Disclaimer for U.S. Appl. No. 11/544,149, submitted Mar. 18, 2011; Amendment Response to Non Final Office Action mailed Jun. 24, 2010, for U.S. Appl. No. 11/544,149, submitted on Dec. 23, 2010; Terminal Disclaimer for U.S. Appl. No. 11/544,149, submitted Dec. 23, 2011; Non Final Office Action for U.S. Appl. No. 11/544,149, mailed Jun. 24, 2010; Amendment Response to Final Office Action mailed Dec. 8, 2009, for U.S. Appl. No. 11/544,149, submitted on May 3, 2010; Examiner Interview Summary Record for U.S. Appl. No. 11/544,149, mailed Feb. 16, 2010; Final Office Action for U.S. Appl. No. 11/544,149, mailed Dec. 8, 2009; Examiner Interview Summary Record for U.S. Appl. No. 11/544,149, mailed Aug. 6, 2009; Supplemental Amendment Response to Non Final Office Action mailed Feb. 18, 2009, for U.S. Appl. No. 11/544,149, submitted on Aug. 6, 2009; Amendment Response to Non Final Office Action mailed Feb. 18, 2009, for U.S. Appl. No. 11/544,149, submitted on Jun. 18, 2009; Non Final Office Action for U.S. Appl. No. 11/544,149, mailed Feb. 18, 2009; Preliminary Amendment for U.S. Appl. No. 11/544,149, submitted Oct. 6, 2006; Application for U.S. Appl. No. 11/544,149, filed Oct. 6, 2006.

File history for related U.S. Appl. No. 10/888,682, filed Jul. 10, 2004, Inventor D. Bruce Modesitt, including (141 pages total): Supplemental Amendment Response to Final Office Action mailed May 6, 2009 for U.S. Appl. No. 10/888,682, submitted on Aug. 28, 2009 Amendment Response to Final Office Action dated May 6, 2009 for U.S. Appl. No. 10/888,682, submitted on Jul. 1, 2009 Final Office Action for U.S. Appl. No. 10/888,682, mailed May 6, 2009 Amendment Response to Non Final Office Action mailed Jul. 31, 2008 for U.S. Appl. No. 10/888,682, submitted on Nov. 26, 2008 Non Final Office

(56) References Cited

OTHER PUBLICATIONS

Action for U.S. Appl. No. 10/888,682, mailed Jul. 31, 2008 Response to Restriction and Election mailed Feb. 15, 2008 for U.S. Appl. No. 10/888,682, submitted on Apr. 30, 2008 Requirement for Restriction and Election for U.S. Appl. No. 10/888,682, mailed on Feb. 15, 2008 Application for U.S. Appl. No. 10/888,682, filed Jul. 10, 2004.
File history for related U.S. Appl. No. 12/693,395, filed Jan. 25, 2010, Inventor D. Bruce Modesitt, including (61 pages): Preliminary Amendment for U.S. Appl. No. 12/693,395, submitted on Jan. 25, 2010 Application for U.S. Appl. No. 12/693,395, filed Jan. 25, 2010.
File history for related U.S. Appl. No. 11/432,982, filed May 12, 2006, Inventor D. Bruce Modesitt, including (128 pages): Examiner Interview Summary Record for U.S. Appl. No. 11/432,982, dated Mar. 14, 2011 Notice Regarding Non-Responsive Amendment for U.S. Appl. No. 11/432,982, dated Jan. 5, 2011 Amendment Response to Non Final Office Action mailed Apr. 15, 2010 for U.S. Appl. No. 11/432,982, submitted on Oct. 15, 2010 Non Final Office Action for U.S. Appl. No. 11/432,982, mailed Apr. 15, 2010 Amendment Response to Final Office Action mailed Jun. 11, 2009 for U.S. Appl. No. 11/432,982, submitted on Aug. 27, 2009 Final Office Action for U.S. Appl. No. 11/432,982, mailed Jun. 11, 2009 Amendment Response to Non Final Office Action mailed Oct. 8, 2008 for U.S. Appl. No. 11/432,982, submitted on Jan. 6, 2009 Non Final Office Action for U.S. Appl. No. 11/432,982, mailed Oct. 8, 2008 Application for U.S. Appl. No. 11/432,982, filed May 12, 2006.
File history for related U.S. Appl. No. 11/544,317, filed Oct. 6, 2006, Inventor D. Bruce Modesitt, including (163 pages): Terminal Disclaimer Decision for U.S. Appl. No. 11/544,317, mailed on Mar. 15, 2011 Amendment Response to Non Final Office Action mailed Jun. 24, 2010 for U.S. Appl. No. 11/544,317, submitted on Dec. 23, 2010 Terminal Disclaimer for U.S. Appl. No. 11/544,317, filed Dec. 23, 2010 Non Final Office Action for U.S. Appl. No. 11/544,317, mailed Jun. 24, 2010 Amendment Response to Final Office Action mailed on Aug. 14, 2009 for U.S. Appl. No. 11/544,317, submitted on Feb. 12, 2010 Final Office Action for U.S. Appl. No. 11/544,317, mailed Aug. 14, 2009 Amendment Response to Non Final Office Action mailed Jan. 9, 2009 for U.S. Appl. No. 11/544,317, submitted on May 11, 2009 Non Final Office Action for U.S. Appl. No. 11/544,317, mailed Jan. 9, 2009 Preliminary Amendment to Application filed on Oct. 6, 2006 for U.S. Appl. No. 11/544,317, submitted on Oct. 6, 2006 Application for U.S. Appl. No. 11/544,317, filed Oct. 6, 2006.
File history for related U.S. Appl. No. 11/788,509, filed Apr. 19, 2007, Inventor D. Bruce Modesitt, including (288 pages): Terminal Disclaimer Decision for U.S. Appl. No. 11/788,509, mailed on Mar. 21, 2011 Terminal Disclaimer for U.S. Appl. No. 11/788,509, as filed on Mar. 18, 2011 Terminal Disclaimer Decision for U.S. Appl. No. 11/788,509, mailed on Mar. 11, 2011 Amendment Response to Non Final Office Action mailed Jun. 24, 2010 for U.S. Appl. No. 11/788,509, submitted on Dec. 23, 2010 Terminal Disclaimer for U.S. Appl. No. 11/788,509, filed Dec. 23, 2010 Non Final Office Action for U.S. Appl. No. 11/788,509, mailed Jun. 24, 2010 Supplemental Amendment Response to Final Office Action mailed Aug. 21, 2009 for U.S. Appl. No. 11/788,509, submitted on Apr. 29, 2010 Amendment Response to Final Office Action mailed Aug. 21, 2009 for U.S. Appl. No. 11/788,509, submitted on Feb. 19, 2010 Final Office Action for U.S. Appl. No. 11/788,509, mailed Aug. 21, 2009 Amendment Response to Notice Regarding Non-Responsive Amendment dated Apr. 15, 2009 for U.S. Appl. No. 11/788,509, submitted on May 14, 2009 Notice Regarding Non-Responsive Amendment for U.S. Appl. No. 11/788,509, dated Apr. 15, 2009 Amendment Response to Non Final Office Action mailed Oct. 29, 2008 for U.S. Appl. No. 11/788,509, submitted on Jan. 6, 2009 Non Final Office Action for U.S. Appl. No. 11/788,509, mailed Oct. 29, 2008 Response to PTO Notice to Applicant mailed May 15, 2007 for U.S. Appl. No. 11/788,509, submitted on Jul. 16, 2007 PTO Notice to Applicant for U.S. Appl. No. 11/788,509, mailed May 15, 2007 Preliminary Amendment to Application as filed on Apr. 19, 2007 for U.S. Appl. No. 11/788,509, submitted on Apr. 19, 2007 Application for U.S. Appl. No. 11/788,509, filed Apr. 19, 2007.
File history for related U.S. Appl. No. 12/467,251, filed May 15, 2009, Inventor D. Bruce Modesitt, including (46 pages): Preliminary Amendment to Application as filed on May 15, 2009 for U.S. Appl. No. 12/467,251, submitted on May 15, 2009 Application for U.S. Appl. No. 12/467,251, filed May 15, 2009.
File history for related U.S. Appl. No. 11/873,957, filed Oct. 17, 2007, Inventor D. Bruce Modesitt, et al., including (90 pages): Amendment Response to Notice Regarding Non-Responsive Amendment dated Feb. 7, 2011 for U.S. Appl. No. 11/873,957, submitted on Mar. 2, 2011 Examiner Interview Summary Record for U.S. Appl. No. 11/873,957, dated Feb. 7, 2011 Notice Regarding Non-Responsive Amendment for U.S. Appl. No. 11/873,957, dated Feb. 7, 2011 Amendment Response to Non Final Office Action mailed Aug. 2, 2010 for U.S. Appl. No. 11/873,957, submitted on Feb. 2, 2011 Terminal Disclaimer for U.S. Appl. No. 11/873,957, filed Feb. 2, 2011 Non Final Office Action for U.S. Appl. No. 11/873,957, mailed Aug. 2, 2010 Application for U.S. Appl. No. 11/873,957, filed Oct. 17, 2007.
File history for related U.S. Appl. No. 12/507,043, filed Jul. 21, 2009, Inventor Michael Drews, et al., including (97 pages): Application for U.S. Appl. No. 12/507,043, filed May 14, 2010.
File history for related U.S. Appl. No. 12/780,768, filed May 14, 2010, Inventor Michael Drews, et al., including (97 pages): Application for U.S. Appl. No. 12/780,768, filed May 14, 2010.
File History for related U.S. Appl. No. 12/888,209, filed Sep. 22, 2010, Inventor D. Bruce Modesitt, et al., including (125 pages): Application for U.S. Appl. No. 12/888,309, filed Sep. 22, 2010.
File history for related U.S. Appl. No. 13/004,848, filed Jan. 11, 2011, Inventor D. Bruce Modesitt, et al., including (91 pages): Application for U.S. Appl. No. 13/004,848, filed Jan. 11, 2011.
Office Action dated Apr. 13, 2010, for Australian Patent Application No. 2005244834, with a filing date of May 12, 2005. (3 pages).
Office Action dated Jun. 3, 2010, for Chinese Patent Application No. 200580023327.X, with a filing date of May 12, 2005, with English translation provided by Chinese associate. (7 pages).
Further Office Action dated Sep. 6, 2010, for Israeli Patent Application No. 179173, with a filing date of Jun. 30, 2005, with English translation provided by Israeli associate. (9 pages).
Response to Office Action submitted Jul. 13, 2010, for Israeli Patent Application No. 179173, with a filing date of Jun. 30, 2005. (1 page).
Initial Office Action dated Jan. 25, 2010, for Israeli Patent Application No. 179173, with a filing date of Jun. 30, 2005, with English translation provided by Israeli associate. (5 pages).
Office Action dated Jan. 24, 2011, for Japanese Patent Application No. 2007-513356, with a filing date of May 12, 2005, and with English translation provided by Japanese associate, (7 pages).
Office Action dated Jan. 24, 2011, for Japanese Patent Application No. 2008-123950, with a filing date of May 12, 2005, and with English translation provided by Japanese associate, (4 pages).
Office Action dated Jun. 4, 2010, for Australian Patent Application No. 2005272102, with a filing date of Jun. 30, 2005. (3 pages).
Response to Office Action submitted Oct. 18, 2010, for Chinese Patent Application No. 2005800293656, with English instructions to respond provided to Chinese associate, (27 pages).
Office Action dated Jun. 4, 2010, for Chinese Patent Application No. 2005800293656, with a filing date of Jun. 30, 2005, with English translation provided by Chinese associate. (10 pages).
Office Action dated Feb. 14, 2011, for European Patent Application No. 05787529.6, with a filing date of Jun. 30, 2005, (15 pages).
European Search Report from European Patent Office for EP application No. EP05787529.6, Applicant Arstasis, Inc., EPO Forms 1507, 1503, and P0459, dated Nov. 5, 2010. (5 pages).
Further Office Action dated May 24, 2010, for Israeli Patent Application No. 180497, with a filing date of May 12, 2005, with English translation provided by Israeli associate. (5 pages).
Response to Office Action submitted May 23, 2010, for Israeli Patent Application No. 180497, with a filing date of May 12, 2005, with English translation provided by Israeli associate. (7 pages).
Initial Office Action dated Jan. 24, 2010, for Israeli Patent Application No. 180497, with a filing date of May 12, 2005, with English translation provided by Israeli associate. (5 pages).

(56) References Cited

OTHER PUBLICATIONS

Office Action dated Dec. 8, 2010, for Japanese Patent Application No. 2007-0520363, with a filing date of Jun. 30, 2005, and with English translation provided by Japanese associate, (5 pages).
Response to Office Action submitted Nov. 6, 2010, for Chinese Patent Application No. 2006800252468, with English instructions to respond provided to Chinese associate. (29 pages).
Office Action dated May 22, 2009, for Chinese Patent Application No. 2006800252468, with a filing date of May 12, 2006, with English translation provided by Chinese associate. (7 pages).
PCT International Preliminary Report on Patentability for PCT/US2009/051320, Applicant Arstasis, Inc., Forms PCT/IB/373 and PCT/ISA/237 dated Jan. 25, 2011. (7 pages).
PCT International Search Report and Written Opinion for PCT/US2009/051320, Applicant Arstasis, Inc., Forms PCT/ISA/210, 220, and 237 dated Nov. 6, 2009. (11 pages).
PCT International Search Report and Written Opinion for PCT/US2010/035001, Applicant Arstasis, Inc., Forms PCT/ISA/210, 220, and 237 dated Jul. 19, 2010. (11 pages).
PCT International Search Report and Written Opinion for PCT/US2010/049859, Applicant Arstasis, Inc., Forms PCT/ISA/210, 220, and 237 dated Nov. 5, 2010. (14 pages).
Second Office Action, Chinese Patent Application No. 200980135885.3, mailed on Sep. 26, 2013.
International Search Report and Written Opinion, International Application No. PCT/US13/42743, mailed on Oct. 24, 2013 (11 pages).
Office Action dated Jan. 14, 2014 for Israeli Application No. 210754 (5 pages).
Office Action dated Jan. 14, 2014 for Israeli Application No. 210755 (4 pages).
International Search Report and Written Opinion, International PCT Application No. PCT/US2013/052926, International Filing Date of Jul. 31, 2013; mailed on Nov. 26, 2013. (9 pages).
Second Office Action for Chinese Patent Application No. 200980135885.3, mailed on Sep. 26, 2013. (6 pages).
Search Report dated Nov. 30, 2012 for European Application No. EP12156932.1. (9 pages).
Office Action dated May 24, 2012 for Canadian Application No. 2566743. (4 pages).
Further Office Action dated Mar. 8, 2013 for Canadian Application No. 2566743. (5 pages).
Further Office Action dated Dec. 23, 2013 for Canadian Application No. 2566743. (6 pages).
Decision of Rejection and Translation dated Jul. 4, 2012 for Chinese Application No. 200580023327_X. (6 pages).
Office Action dated May 10, 2013 for Chinese Application No. 200580023327_X. (5 pages).
Further Office Action dated Nov. 25, 2013 for Chinese Application No. 200580023327_X. (3 pages).
Official Communication dated Nov. 26, 2012 for European Application No. 05747814.1. (5 pages).
Supplementary Search Report dated Jul. 23, 2012 for European Application No. 05747814.1. (4 pages).
Office Action dated Aug. 27, 2013 for Israeli Application No. 179173 (7 pages).

Examination Report dated Feb. 27, 2012 for European Application No. 08011884.7. (3 pages).
Office Action dated Sep. 10, 2012 for Japanese Application No. 2008123950 (6 pages).
Notice of Final Rejection dated Nov. 17, 2011 for Japanese Application No. 2008-123950 (5 pages).
Partial Search Report dated Aug. 12, 2013 for European Application No. 12156932.1 (6 pages).
Search Report dated Nov. 12, 2013 for European Application No. 12156932.1 (9 pages).
Examination Report dated Nov. 1, 2012 for Australian Application No. 2012200175. (4 pages).
Office Action dated Nov. 20, 2013 for Japanese Application No. 2012-061872 (6 pages).
Office Action dated May 23, 2012 for Canadian Application No. 2573065. (3 pages).
Office Action dated Feb. 5, 2013 for Israeli Application No. 187109 (5 pages).
Office Action dated Dec. 28, 2012, for Chinese Patent Application No. 2005800293656, with a filing date of Jun. 30, 2005, with English translation provided by Chinese associate. (6 pages).
Office Action dated Apr. 22, 2013, for Chinese Patent Application No. 2005800293656, with a filing date of Jun. 30, 2005, with English translation provided by Chinese associate. (6 pages).
Supplementary Search Report dated Nov. 5, 2010 for European Application No. 05787529.6. (5 pages).
Official Communication dated Feb. 14, 2011 for European Application No. 05787529.6. (4 pages).
Examination Report dated Sep. 11, 2012 for Australian Application No. 2012201140. (4 pages).
Examination Report dated Mar. 16, 2011 for Australian Application No. 2006247355. (4 pages).
Examination Report No. 2 dated Oct. 25, 2012 for Australian Application No. 2006247355. (3 pages).
Office Action dated Jan. 16, 2013 for Canadian Application No. 2607387. (2 pages).
Notice of Rejection (Translation) dated Nov. 13, 2012 for Japanese Application No. 2010-101185. (3 pages).
First Office Action dated Jan. 7, 2013, for Chinese Patent Application No. 200980135885.3, with English translation provided by Chinese associate. (6 pages).
Second Office Action dated Sep. 26, 2013, for Chinese Patent Application No. 200980135885.3, with English translation provided by Chinese associate. (12 pages).
Notice of Rejection and English Translation dated Sep. 2, 2013 for Japanese Application No. 2010-520145. (4 pages).
Office Action dated Feb. 2, 2014 for Israeli Application No. 216263 (5 pages).
First Office Action dated Mar. 5, 2014, for Chinese Patent Application No. 201080052596.X, English translation provided by Chinese associate. (17 pages).
Office Action mailed on Jan. 14, 2014 for Israeli Application No. 210755 (4 pages).
Office Action mailed on Jan. 14, 2014 for Israeli Application No. 210754 (5 Pages).

\* cited by examiner

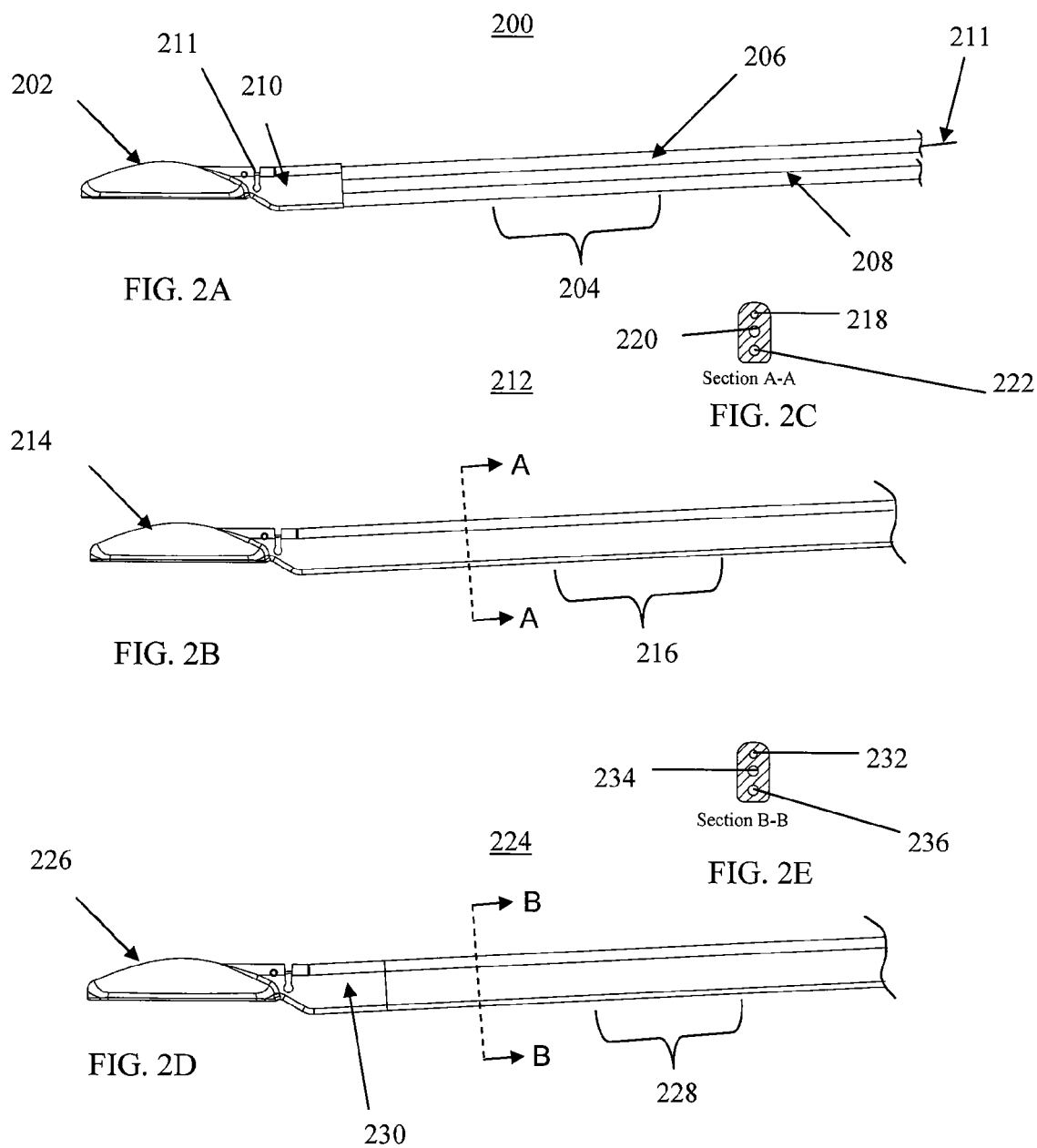

Detail C 902    906    904

904    906

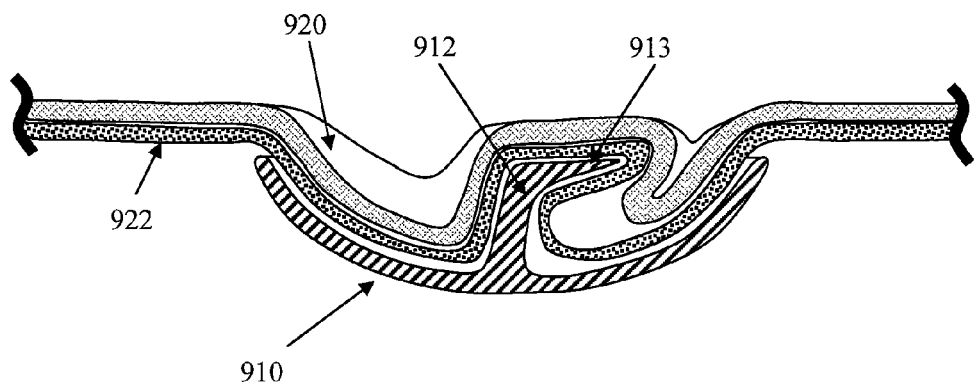
FIG. 9I
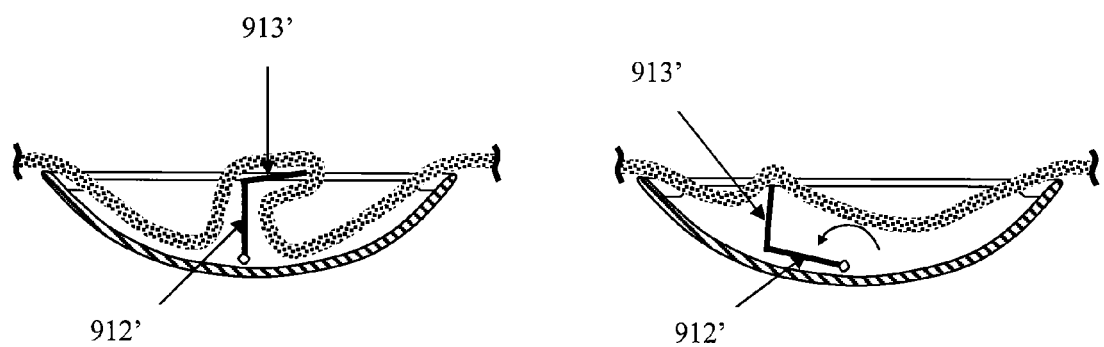
FIG. 9J
FIG. 9K

DEVICES, METHODS, AND KITS FOR FORMING TRACTS IN TISSUE

CROSS-REFERENCE TO RELATED APPLICATIONS

This application claims the benefit of U.S. Provisional Application No. 61/082,449, filed Jul. 21, 2008, the disclosure of which is incorporated herein by reference in its entirety.

FIELD

In general, the methods, devices, and kits described herein are useful for forming tracts in tissue. More specifically, the methods, devices, and kits described herein are useful for forming tracts in tissue using one or more suction members.

BACKGROUND

A number of devices and methods have previously been described for forming tracts in or through tissue. For example, U.S. patent application Ser. Nos. 10/844,247, 11/544,196, 11/545,272, 11/544,365, 11/544,177, 11/544,149, 10/888,682, 11/432,982, 11/544,317, 11/788,509, 11/873,957 all of which are incorporated by reference in their entirety herein, describe devices and methods for forming tracts in tissue. In general, the tracts described there self-seal or seal with minimal or no need for supplemental closure devices or techniques. These tracts may be quite useful in providing access to a tissue location (e.g., an organ lumen) so that one or more tools may be advanced through the tract, and a procedure may be performed. Given the tremendous applicability of such methods, additional devices and methods of forming tracts in tissue would be desirable.

BRIEF SUMMARY

Described here are methods and devices for forming tracts in tissue. In some variations, the devices comprise an elongate member, a suction member coupled to a distal portion of the elongate member, and a tissue-piercing member slidably housed within the elongate member for forming a tract in tissue. The elongate member may or may not be flexible. In some variations, the suction member is coupled to the elongate member via a flexible portion, e.g., a hinge or the like.

The elongate member may be articulatable, the tissue-piercing member may be articulatable, the suction member may be articulatable, or any combination of the foregoing members may be articulatable. These members may be articulatable for instance, using one or more pull wires, one or more hinges, or the like.

In some variations, the tissue-piercing member is a needle. The needle may be hollow or solid, and may have any suitable tip. That is, the tip may have any suitable shape (conical, offset conical, etc.), may be blunt, sharpened or pointed, and may be beveled or non-beveled.

The suction member may be connected to one or more vacuum sources. For example, the elongate member may have one or more lumens, slots, holes, openings, etc. for facilitating connection of the suction member to a vacuum source. In some variations, the suction member has one or more tissue apposition members thereon. The tissue apposition member may be, for example, a contoured surface, such as a rib. Any number of tissue apposition members may be used as desirable or appropriate. Similarly, the suction members may comprise one or more heating elements, one or more electrodes, or one or more sensors (e.g., Doppler, pressure, nerve sensors, ultrasound sensors, etc.), one or more drug delivery ports along a surface thereof, one or more traction members, or the like. The suction member may have any suitable geometry. In some variations, the basal surface of the suction member is generally elliptical in shape. In other variations, the basal surface of the suction member is generally circular in shape. In still other variations, the basal surface of the suction member has an irregular geometry.

Other devices for forming tracts in tissue comprise an elongate member, a first suction member coupled to a distal portion of the elongate member and positionable against tissue, a second suction member opposed to the first suction member, and a tissue-piercing member for forming a tract in tissue. The tissue-piercing member may be slidably housed within the elongate member, slidably housed within the first or second suction members, or both slidably housed within the elongate member and within either the first or second suction member. The first suction member may be coupled to a distal portion of the elongate member via a flexible portion, e.g., a hinge. Similarly, the second suction member may be coupled to a distal portion of the elongate member, or the first and second suction members may be coupled together, e.g., via a flexible portion such as a hinge. One or more suction members may be movable with respect to the elongate member, with respect to other suction members, or both.

In these variations, the elongated shaft may be articulatable, flexible, or both. Of course, the elongated shaft may also be non-articulatable and/or rigid. The first and second suction members may be connected to a vacuum source, may be moveable relative to one another, and may have any suitable geometry (e.g., generally elliptical, generally circular, generally semi-circular, etc.). Either the first or second suction members may have one or more tissue apposition members thereon, e.g., a contoured surface or rib. Similarly, either the first or second suction members may comprise one or more heating elements, one or more electrodes, or one or more sensors (e.g., Doppler, pressure, etc.), one or more traction members, one or more ports, and the like. In some variations, the tissue-piercing member is a needle. As with the devices described above, the needle may be hollow or solid, and may have any suitable tip. That is, the tip may have any suitable shape (conical, offset conical, etc.), may be blunt, sharpened or pointed, and may be beveled or non-beveled.

In some variations, the device further comprises one or more energy applicators and the method further comprises applying energy to the tissue. The energy may come from any suitable energy source (e.g., energy selected from the group consisting of ultrasound, RF, light, magnetic, or combinations thereof). In some variations, the device comprises one or more sensors and the method further comprises sensing at least one useful parameter, e.g., temperature, pressure, tissue identification or location (e.g., nerves or various anatomical structures), blood flow within a vessel, and combinations thereof. For example, in some variations, the parameter is blood flow within a vessel, and the method further comprises repositioning the device if blood flow within a vessel is detected. Kits incorporating one or more of the devices described here, in conjunction with one or more tools or the like, are also described here.

Methods for forming tracts in tissue are also described here. In accordance with some methods, a device is advanced adjacent tissue, where the device comprises one or more suction members and a tissue-piercing member. Suction is applied so that the tissue is drawn against the one or more suction members, and a tissue-piercing member is advanced in a first direction through the drawn tissue to form a tract in or through the tissue. The methods may further comprise, articulating the tissue-piercing member and advancing the tissue-piercing member in a second direction. In some variations, the method further comprises articulating the one or more suction members to reposition the tissue, with or without advancing the tissue-piercing member through the repositioned tissue. The methods may further comprise rotating the device to rotate the tissue, and advancing the tissue-piercing member through the rotated tissue. Of course, the methods may also include visualizing the tissue, advancing one or more tools through the tissue tract, performing a procedure adjacent to, through, or on the tissue, determining the location of the device with respect to the tissue, combinations thereof, and the like.

The methods described here may also comprise delivering one or more fluids or agents to the tissue. The fluids may be useful, for example, for irrigation, sterilization, treatment of tissue (therapeutic, etc.), or the like. The fluids may comprise any suitable agent or combination of agents. For example, the agent may be selected from the group consisting of antibiotics, antiseptics, sterilizing agents, chemotherapeutics, non-steroidal anti-inflammatory drugs (NSAIDs), cyclooxygenase-1 (COX-1) inhibitors, cyclooxygenase-2 (COX-2) inhibitors, opioids, or any other drug or agent, and mixtures and combinations thereof. The fluid may also comprise one or more cryogenic agents, e.g., to freeze tissue, reduce inflammation, cause localized cell death, some combination of the foregoing, or the like. The cryogenic agent may be, for example, liquid nitrogen or some other cryogenic agent. Furthermore, a metal or polymer tubular conduit may be located within, outside, around, or adjacent to, the suction member, and may be coupled to a conduit located in, around, or adjacent to the elongated member, such that the cryogenic agent passes from one conduit to the next without ever directly contacting the tissue. In this way, a heat exchanger of sorts is created, so that he heat is removed from within the suction member and the temperature of the tissue is reduced to a therapeutic level. In some variations, as will be described in more detail below, the tissue-piercing member is configured to provide for injection of an agent.

The methods may be used with any suitable tissue. In some variations, the tissue is an organ, e.g., an organ of the cardiovascular system, an organ of the digestive system, an organ of the respiratory system, an organ of the excretory system, an organ of the reproductive system, or an organ of the nervous system. In some variations, the organ is an organ of the cardiovascular system, e.g., an artery. When the methods described here are used, the tract may seal in a relatively short amount of time, and may seal with or without additional aid. In some variations, the tract seals within 15 minutes or less, within 12 minutes or less, within 10 minutes or less, within 5 minutes or less, within 3 minutes or less, or within 1 minute or less. Of course, pressure or suction may be applied to the tract after it has been formed to aid in sealing. In addition, one or more closure devices may also be used.

In accordance with the methods described here, the tissue-piercing member may be advanced in an undulating fashion, or may be rotated during advancement. In some variations, the tissue-piercing member enters the tissue at a first location, and exits the tissue at a second location, and the length between the first location and the second location is greater than the thickness of the tissue. In some variations, the length of the tract is greater than the thickness of the tissue. In some variations, the methods further comprise enlarging the cross-sectional area of the tract.

Some variations of methods described here may be used to form a single self-sealing tract in tissue, or may be used to form one or more self-sealing tracts in tissue by advancing a single tissue-piercing member into the tissue. This may, for example, result in minimal stress on the tissue. Moreover, the tissue may recover relatively quickly, thereby resulting in relatively short procedure time.

Certain variations of the methods described here may comprise forming a tract in tissue by advancing a first tissue-piercing member (e.g., a needle, such as a hollow needle) in a first direction through the tissue, where formation of the tract requires advancement of only the first tissue-piercing member through the tissue, and where the tract is self-sealing. The methods may also comprise advancing a device comprising the first tissue-piercing member adjacent to the tissue prior to advancing the first tissue-piercing member through the tissue. In some variations, the methods may comprise applying suction to the tissue to position the tissue. For example, the device may further comprise one or more suction members, and the methods may comprise applying suction to the tissue to draw the tissue against the suction member or members. In certain variations, the first tissue-piercing member may be advanced in the first direction through the drawn tissue. In some variations, the tract may be formed in the tissue after the tissue has been positioned by the application of suction. The tract may, for example, be an arteriotomy.

Some variations of the methods described here may comprise advancing a tissue-piercing member in a first direction through tissue to form a single tract in the tissue, where the single tract is self-sealing. Certain variations of the methods described here may comprise advancing a device adjacent tissue, where the device comprises at least one tissue-piercing member. The methods may further comprise forming a tract in the tissue by advancing the tissue-piercing member or members through the tissue. Formation of the tract may require advancement only of the tissue-piercing member or members through the tissue. The tract may be self-sealing.

BRIEF DESCRIPTION OF THE DRAWINGS

FIGS. 2A-2F depict various suitable configurations of how elongate members and suction members may be coupled to one other including depictions of the lumen configurations associated therewith.

FIG. 9I is an illustrative cross-sectional depiction of how tissue may fold around and/or underneath the ridge of the suction member depicted in FIGS. 9G and 9H.

FIGS. 9J and 9K provide an illustrative cross-sectional depiction of how tissue may fold around and/or underneath an illustrative articulatable or moveable ridge of a suction member.

FIG. 9O depicts a basal surface of a suction member, where the basal surface of the suction member defines a series of apertures or windows.

FIGS. 10A-10D depict illustrative suction members where the suction members have one or more discrete features thereon or therein, such as electrodes, heating elements, sensors, markers, cameras, or the like.

DETAILED DESCRIPTION

Described here are methods and devices for forming tracts in tissue. In general, the devices described here comprise one or more suction members for drawing tissue thereagainst, for facilitating advancement of a tissue-piercing member therethrough. The devices may take on a variety of forms and may have a number of additional or useful features, as will be described in detail below. The devices may be used to form tracts through any type of tissue. The tissue may be tissue of the cardiovascular system, the digestive system, the respiratory system, the excretory system, the reproductive system, the nervous system, or the like.

In general, when the devices described here are used to form tracts in or through the tissue, the tracts are capable of self-sealing with minimal or no additional sealing efforts, as described, for example, in U.S. patent application Ser. Nos. 10/844,247, 11/544,196, 11/545,272, 11/544,365, 11/544,177, 11/544,149, 10/888,682, 11/432,982, 11/544,317, 11/788,509, 11/873,957, 12/467,251, 61/119,316, and 61/178,895, each of which is incorporated by reference herein in their entirety. It should be understood from the outset, however, that the devices and methods described here may be complemented by the use of one or more additional closure mechanisms or techniques (e.g., closure devices, delivery of energy, application of pressure, etc.). Kits incorporating one or more of the devices described here, in conjunction with one or more tools or the like, are also described here. Variations of the devices, methods, and kits will now be described.

I. Devices

Figure 1:
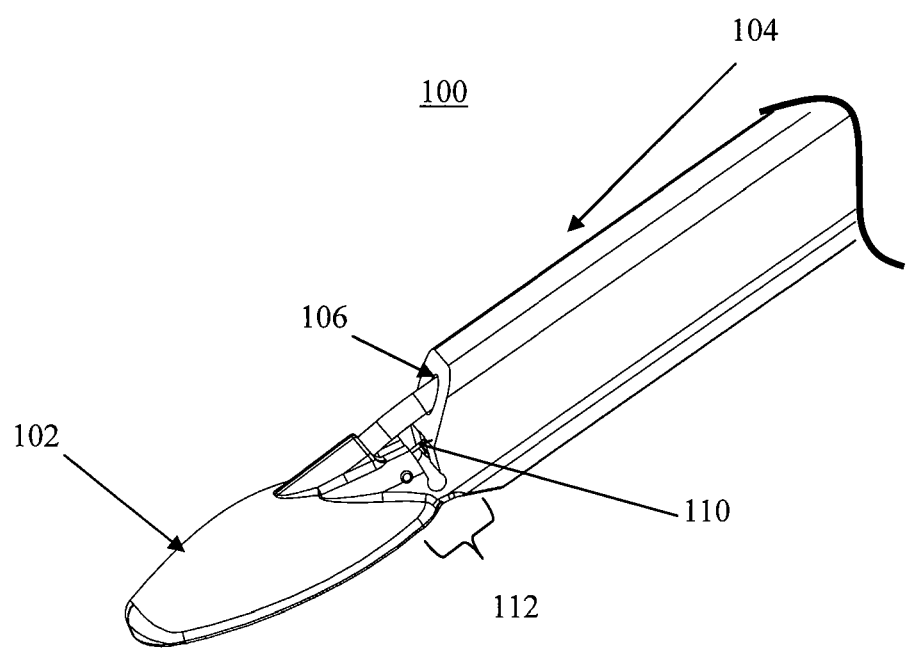
FIG. 1 is an illustrative depiction of the distal end of an exemplary device that may be used to form tracts in tissue as described here.

FIG. 1 provides an illustrative device (100) for forming tracts in tissue in accordance with the methods described herein. Shown there is suction member (102) coupled to an elongate member (104). The elongate member may be any suitable member that serves to connect the suction member (102) to the proximal end of the device (not shown). The elongate member (104) may comprise one or more lumens for providing additional features or controls for the device. For example, the elongate member (104) may comprise a lumen for vacuum or suction (106), a lumen for housing a tissue-piercing member therein, or the like. The elongate member (104) may also comprise one or more lumens for housing one or more pull wires (110), optical or electrical connections (e.g., to deliver power, to connect sensors, to provide visualization, etc.), and the like.

Additional variations of suitable lumen and elongate member configurations will be described with reference to FIGS. 2A-2F below. Proximal control will be described in more detail below with reference to the methods, however, it is noted at the outset that proximal controls may include one or more buttons, switches, or sliders to actuate one or more features of the device (e.g., to actuate a tissue-piercing member, to actuate delivery of fluid, to actuate vacuum, to actuate delivery of energy, to actuate visualization, etc.). Of course, the proximal control may also include (alone or in combination with those controls just described) one or more valves (e.g., two-way or three-way valves) to help turn on or off the vacuum, on or off a flush line, and the like.

When pull wires are used, they may be used, for example, to help facilitate movement, control, or actuation of the device. In the variation shown in FIG. 1, pull wire (110) is used to articulate the suction member (102) at region (112). Region (112) may comprise a region of reduced thickness or greater flexibility when compared with the remainder of the suction member (102) or the elongate member (104). Region (112) may be made of the same or different material than the suction or elongate members. For example, region (112) may comprise a softer material, a thinner material, a more flexible material, or other different material than the suction or elongate members, or region (112) may be made of the same general material as the suction or elongate members with one or more physical or chemical property modifications. Region (112) may also comprise one or more joints or hinges (e.g., single or multiple flexure joints, revolute joints, pivot hinges, molded plastic live hinges, ball and socket joints, slidable tubes with counter-opposed flexure elements, etc).

Of course, the elongate member may be made of any suitable biocompatible material. For example, it may comprise or be made of stainless steels, for example, 304, 304L, 316, 316L, 440C, or the like, titanium alloys, for example 6Al-4V or the like, nickel-titanium alloys (Nitinol), cobalt-chromium alloys, for example Elgiloy® (Elgiloy Specialty Metals, Elgin, Ill.), MP35N® (SPS Technologies, Inc, Jenkintown, Pa.), Phynox® (Imphy Ugine Precision, France), or the like, aluminum, polymers, for example, ABS, nylon, acetal, high-density polyethylene (HDPE), low-density polypolyethylene (LDPE) polyester, polyurethane, polypropylene, polyolefin, urethane, silicone, polyvinylchloride (PVC), polycarbonate, polyetherimide (PEI), polyethersulfone, polyarylethersulfone, polysulfone, ultrahighmolecularweightpolyethlene (UHMW-PE), polyetheretherketone (PEEK), polyetherketoneketone (PEKK), PEBAX® (Colombes Cedex, France), polytetrafluroethylene (PTFE), or any other polymer, polymer blend or filled polymer, for example, glass-fiber, carbon-fiber, or other suitable carbon based material. Additionally, any compound/agent to improve the polymers radioopacity may be incorporated, for example, barium sulphate, platinum, gold, tungsten, or the like. The elongate member may also be made to have one or more scalloped or contoured edges (e.g., top, bottom, side) to help impart flexibility.

Similarly, the suction member may be made of any suitable biocompatible material. For example, the suction member may comprise or be made from stainless steels, for example, 304, 304L, 316, 316L, 440C, or the like, titanium alloys, for example 6Al-4V or the like, nickel-titanium alloys (Nitinol), cobalt-chromium alloys, for example Elgiloy® (Elgiloy Specialty Metals, Elgin, Ill.), MP35N® (SPS Technologies, Inc, Jenkintown, Pa.), Phynox® (Imphy Ugine Precision, France), or the like, polymers, for example, ABS, nylon, acetal, high-density polyethylene (HDPE), low-density polypolyethylene (LDPE) polyester, polyurethane, polypropylene, polyolefin, urethane, silicone, polyvinylchloride (PVC), polycarbonate, polyetherimide (PEI), polyethersulfone, polyarylethersulfone, polysulfone, ultrahighmolecularweightpolyethlene (UHMW-PE), polyetheretherketone (PEEK), polyetherketoneketone (PEKK), PEBAX® (Colombes Cedex, France), polytetrafluroethylene (PTFE), polyimide, or any other polymer or polymer blend or filled polymer, for example, glass-fiber, carbon-fiber, or any other suitable carbon-based material. Additionally, any compound/agent to improve the polymers radioopacity may be incorporated, for example, barium sulphate, platinum, gold, tungsten, or the like.

The suction member, the elongate member, or both members may be made of one or more materials to impart flexibility, rigidity, or any other suitable characteristic. It should also be understood that a variety of different materials may be used for each of these members, and that the members may be constructed accordingly. For example, the suction member (102) may be made with a flexible periphery using an overmolding technique, understood by those having ordinary skill in the art. Also, while the suction member (102) is shown in FIG. 1 as having a generally elliptical basal (or tissue contacting) surface, it should be understood that the basal surface of the suction member may have any suitable or desirable geometry (e.g., circular, rectangular, triangular, toroidal, etc.). Of course, the geometry need not be symmetric, uniform, regular, or easily describable. As will be described in more detail below, the suction member (102) may also comprise one or more additional features (e.g., contoured surfaces, electrodes, sensors, tissue apposition members, traction members, channels, ports, cameras, markers, etc.).

FIGS. 2A-2D provide illustrative depictions of suitable devices detailing various suitable suction member-elongate member junctions. Shown in FIG. 2A is device (200) comprising a suction member (202) and elongate portion (204). In this variation, the elongate portion (204) comprises discrete elongate bodies (206 and 208), each separately defining a lumen. Elongate body (206) may provide a conduit for vacuum or suction, while elongate body (208) may serve to slidably house a tissue-piercing member therein. In the variation shown in FIG. 2A, both elongate members (206 and 208) are connected or attached to (e.g., by overlapping fit, edge-to-edge, fit etc.) connector (210), which in turn is connected to the suction member (202). The connection between connector (210) and suction member (202) may be effected in any suitable manner. For example, the connector (210) and the suction member (202) may be connected via welding (ultrasonic, heat, chemical, etc.), snap-fit, press-fit, using interlocking features, using one or more adhesives or glues, using one or more mechanical features or fixtures (e.g., screws, clamps, crimps, rivets, tabs, bolts, etc.), or the like.

The variation depicted in FIG. 2A may find particular utility in instances where greater flexibility is desirable (e.g., when maneuvering through tortuous anatomy). It should be understood that the connector (210) may be integral with the suction member (202) (i.e., the connector and suction member may be formed from a single piece of material), but need not be. It should also be understood that while the elongate bodies (206 and 208) depicted in FIG. 2A have generally circular cross-sections, the elongate bodies may have cross-sections having any suitable geometry.

FIG. 2B provides an alternative variation of a device for use with the methods described herein. Shown in FIG. 2B is a device (212) comprising suction member (214) and elongate member (216). In this variation, the elongate member (216) defines discrete lumens (218, 220, 222) as shown in FIG. 2C. In variations where additional flexibility may be desirable, the elongate member (216) of FIG. 2B may have one or more scalloped or contoured edges as described above.

Any of the lumens described herein may be used for any suitable purpose (e.g., facilitating vacuum or suction, delivering fluids or drugs, housing one or more electrodes, housing one or more pull wires, housing one or more tissue-piercing members, etc.). It should be understood that more than one lumen may be used for the same general purpose (e.g., two lumens for housing two pull wires, two lumens for delivering two separate drugs, etc.), and that the lumens may have any suitable cross-sectional geometry (whether the same or different). It should also be understood, that a single lumen may be useful in facilitating more than one function (e.g., a single lumen may house a pull wire (211), and serve as a conduit for vacuum or suction, as with the variation shown in FIG. 2A above). The lumens may be concentric and may or may not define complete enclosures (e.g., one or more lumens may approximate a slit or groove). The lumens may also be variously positioned about or along the elongate member. For example, the lumens may be vertically positioned as shown in FIG. 2C, horizontally positioned, randomly positioned, or selectively positioned along a plane to help impart additional flexibility to the device. The lumens may or may not be positioned in accordance with any given pattern.

FIG. 2D depicts a device (224) similar to that of FIG. 2B, except that the elongate member (228) is connected to the suction member (226) via connector (230). FIG. 2E provides a cross-sectional representation of the device (224) taken along line B-B. The lumens shown there (232, 234, 236) may have any of the features or characteristics described just above. The variations shown in FIGS. 2B and 2D may be of particular utility when device rigidity and/or torquability is desired.

Figure 2F:
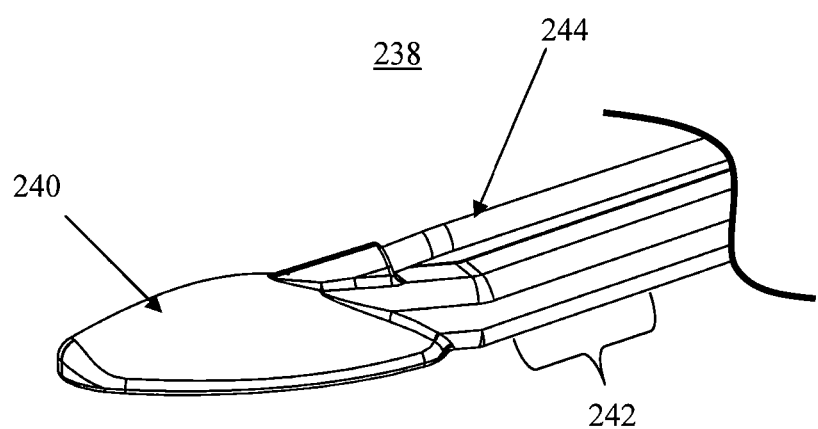

FIG. 2F provides an illustration of a device having both integral lumens, and a discrete connector for vacuum. Shown there is device (238) comprising suction member (240), elongate member (242), and vacuum hose or connector (244). In this variation, the tissue-piercing member is configured to exit within the suction member (240), as will be discussed in more detail below. Thus, the basal surface of the elongate member need not extend beyond the basal surface of the suction member. This may be useful, for instance, in that it may impart a reduced profile to the device, and may help prevent unwanted potential interference with tissue.

Figure 3A:
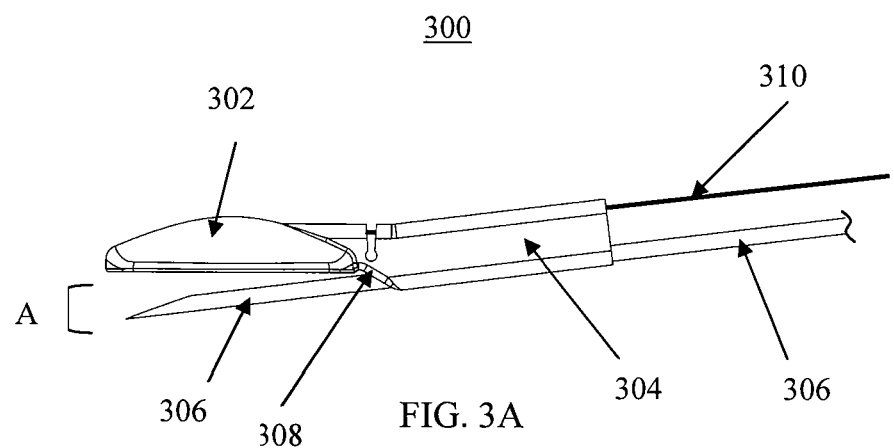
FIGS. 3A and 3B provide depictions of an illustrative device as described herein, in an unflexed and flexed state respectively.
Figure 3B:
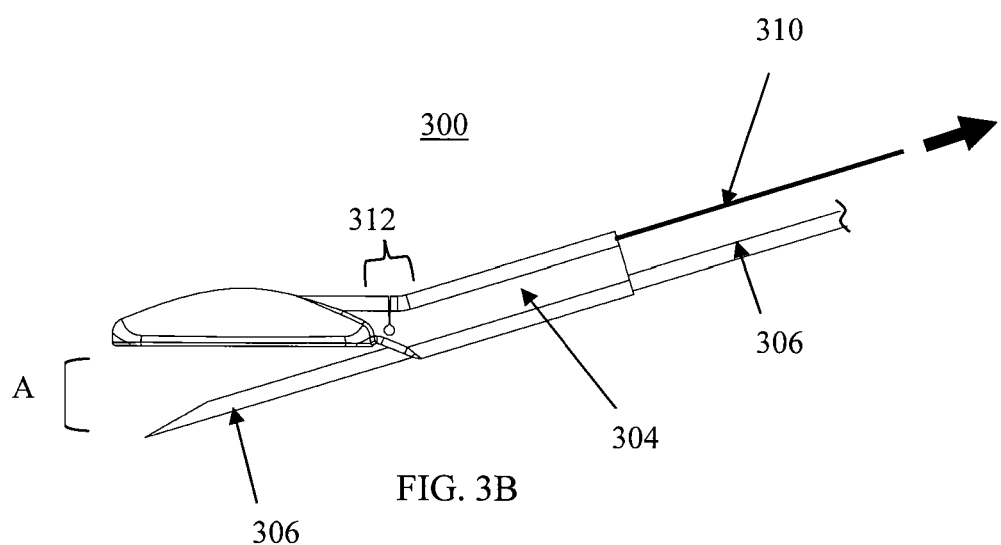

FIGS. 3A and 3B provide depictions of an illustrative device in an unflexed and flexed state respectively. Flexure and articulation of the device along with redirection of the tissue-piercing member will be discussed in greater detail below with reference to the methods. Shown in FIGS. 3A and 3B is device (300), comprising suction member (302) and elongate member (304). In both figures, elongate member (304) has been removed along a proximal portion for ease of explanation. As shown there, elongate member houses tissue-piercing member (306) slidably therein (e.g., in a lumen defined by the elongate member). In FIG. 3A the device is shown in an actuated, but unflexed fashion (i.e., the tissue-piercing member has been advanced out of exit port (308), but has not been flexed).

The initial (i.e., unflexed or unarticulated) angle (A) defined by the basal surface of the suction member (302) and the tissue-piercing member (306) may be any suitable angle. For example, the angle may be from about 0° to about 180°, from about 0° to about 90°, from about 90° to about 180°, from about 0° to about 60°, from about 0° to about 30°, from about 3° to about 10°, about 5°, or the like.

FIG. 3B shows device (300) after pull wire (310) has been pulled proximally causing flexure at region (312). In the variation shown in FIG. 3B, flexure of the device changes the angle (A) defined by the basal surface of the suction member (302) and the tissue-piercing member (306) (e.g., increases or decreases the angle) as the tissue-piercing member lumen is deflected downward. The tissue-piercing member shown in FIGS. 3A and 3B is a beveled needle, though the tissue-piercing member need not be a needle (e.g., the tissue-piercing member may be a wire, energy delivery device, etc.). In variations, where the tissue-piercing member is a needle, the needle may be solid or hollow, may have two or more concentric needle members, may be beveled or non-beveled, and may be pointed, sharpened, or blunt. When needles are used, the needle tip may have any suitable geometry, e.g., conical, offset conical, rounded, or the like. The tissue-piercing member may be individually, discretely, or separately articulated by one or more pull wires. Of course, in instances where the tissue-piercing member is housed within one or more lumens of the elongate member or the like, the tissue-piercing member may be sterilized and kept sterilized prior to use.

It should also be understood that while tissue-piercing member lumen (308) is shown in FIGS. 3A and 3B as exiting adjacent to the suction member (302), the lumen may instead exit within or through the suction member (302), as will be described in more detail below. Of course, the elongate member may comprise any number of ports (e.g., for multiple tissue-piercing members, for additional tools, or the like), which in turn may be connected to one or more lumens.

FIGS. 4-10 depict illustrative variations of suitable suction members for use with the devices and methods described here. These figures provide views of the underside of the suction members. Beginning with FIGS. 4A and 4B, a suction member (400) is shown having one or more tissue apposition members. In this variation, the tissue apposition member comprises one or more joining ribs (402) connected to a peripheral or bounding rib (404). It should be understood that while four ribs (402) are shown connected to the peripheral rib (404), any number of ribs (e.g., 0, 1, 2, 3, 4, 5 to a great many ribs) may be used, as will be apparent below. Indeed, in some variations, the suction member has only a peripheral or bounding rib, which is not joined by or connected to any other ribs. In other variations, the suction member has only a peripheral or bounding rib and a single central rib (positioned laterally or longitudinally) connected thereto.

Figure 4A:
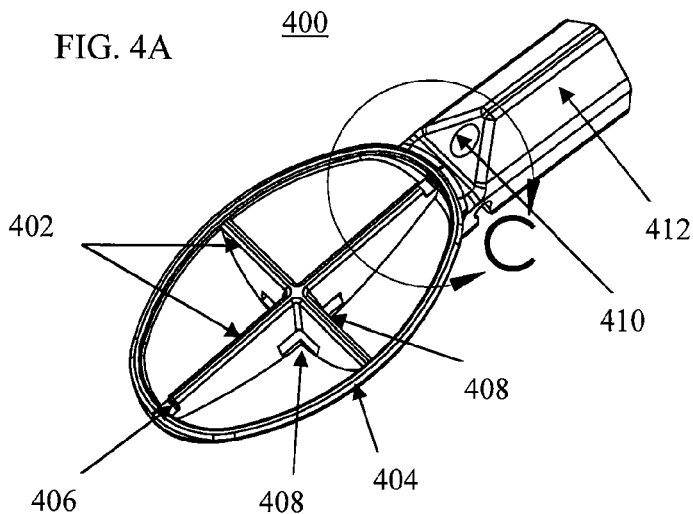
FIG. 4A depicts an illustrative suction member having one or more tissue apposition members, here in the form of four ribs and one peripheral rib (forming a generally cross-shape configuration).

The peripheral and joining ribs need not be separate members (i.e., the entire tissue apposition member may be formed from a single piece of material). In some instances, whether the tissue apposition member is formed from a single piece of material or is formed by connection of more than one member, it may be desirable to provide for one or more recesses (406) where the peripheral and joining ribs connect, as shown in FIG. 4A and in more detail in FIG. 4B. This may, for example, be desirable in order to provide a better vacuum seal along the basal surface of the suction member by providing a greater contact surface with the tissue. This in turn may make the seal less prone to disruption by tissue movement.

The ribs may be useful, for example, to keep the tissue at a distance from the vacuum ports (shown in FIG. 4A as (408)) to help prevent tissue from plugging those ports, and to help facilitate even distribution of vacuum (which in turn provides for greater uniformity in tissue apposition). The ribs may also help provide lateral traction for the suction member, since the boundaries of the ribs form discrete regions where tissue may enter. The number and geometry of the ribs may be selected to effect greater or lesser traction as desirable. When the methods and devices described here are used with very soft, compliant, or thin tissue (e.g., intestinal tissue), a greater number of ribs may be desirable.

Figure 4B:
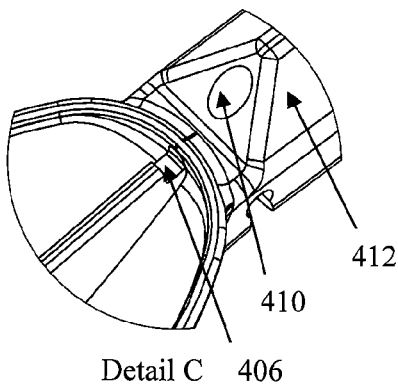
FIG. 4B is a close-up of the device of FIG. 4A taken along detail C.

Also shown in FIGS. 4A and 4B is lumen (410) within elongate member (412). Lumen (410), for example, may be useful for housing a tissue-piercing member slidably therein. Of course, the lumen may also be used for any of the purposes described above.

Figure 5:
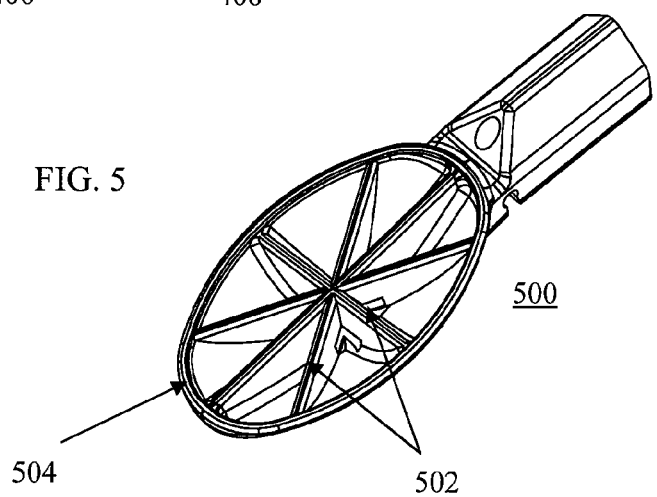
FIG. 5 depicts an illustrative suction member having one or more tissue apposition members, here in the form of eight ribs and one peripheral rib (forming a generally star-shape configuration).
Figure 6:
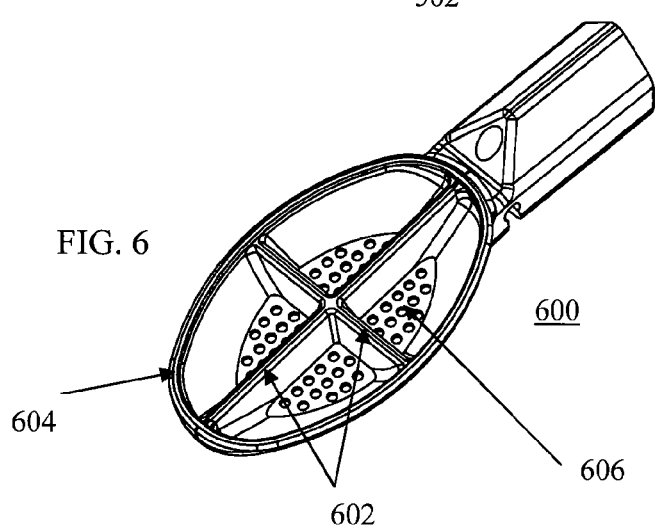
FIG. 6 provides an illustration of a suction member having a mesh or screen covering the suction ports.

FIG. 5 provides an illustration of a suction member (500) having eight ribs (502) connected to peripheral rib (504), forming a generally star-shaped configuration. FIG. 6 provides an illustration of a suction member (600) having four ribs (602) connected to a peripheral rib (604). In the variation shown here, a mesh or screen (606) is provided that covers the suction ports. In this way, tissue may be prevented from entering and plugging the ports. While the screen (606) shown in FIG. 6 is positioned immediately adjacent to the suction ports, the screen may be placed at any suitable distance from the ports. That is, the screen (606) may be located at any depth within the suction member, and the depth may be selected as desirable, e.g., to affect tissue traction.

Figure 7A:
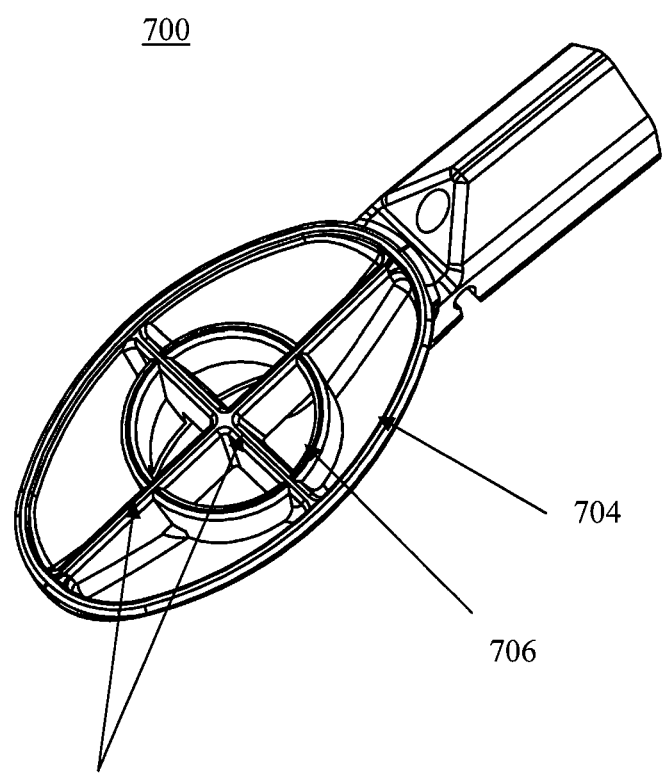
FIG. 7A depicts an illustrative suction member having a central circular rib in addition to the four joining ribs and one peripheral rib.

FIG. 7A provides another variation of a suction member (700), here having four joining ribs (702), one circular central rib (706), and a peripheral rib (704). Of course, the central circular rib (706) may itself be made from several ribs, or the central circular rib, in addition to the entire tissue apposition member, may be made from a single piece of material. It should be clear that while a circular central rib (706) is shown in FIG. 7A, any rib geometry may be used for the central rib member. Indeed, it should be clear that any number and geometry (width, length, depth, shape, etc.) of ribs may be used as desirable, and that these ribs may be separate or integrally formed.

The ribs may be made from any suitable biocompatible material or combination of materials. For example, the ribs may be made from stainless steel, for example, 304, 304L, 316, 316L, 440C, or the like, titanium alloys, for example 6Al-4V or the like, nickel-titanium alloys (Nitinol), cobalt-chromium alloys, for example Elgiloy® (Elgiloy Specialty Metals, Elgin, Ill.), MP35N® (SPS Technologies, Inc, Jenkintown, Pa.), Phynox® (Imphy Ugine Precision, France), or the like, polymers, for example, ABS, nylon, acetal, high-density polyethylene (HDPE), low-density polypolyethylene (LDPE) polyester, polyurethane, polypropylene, polyolefin, urethane, silicone, polyvinylchloride (PVC), polycarbonate, polyetherimide (PEI), polyethersulfone, polyarylethersulfone, polysulfone, ultrahighmolecularweightpolyethlene (UHMW-PE), polyetheretherketone (PEEK), polyetherketoneketone (PEKK), PEBAX® (Colombes Cedex, France), polytetrafluroethylene (PTFE), polyimide, or any other polymer or polymer blend or filled polymer, for example, glass-fiber, carbon-fiber, or other suitable carbon-based materials.

Figure 7B:
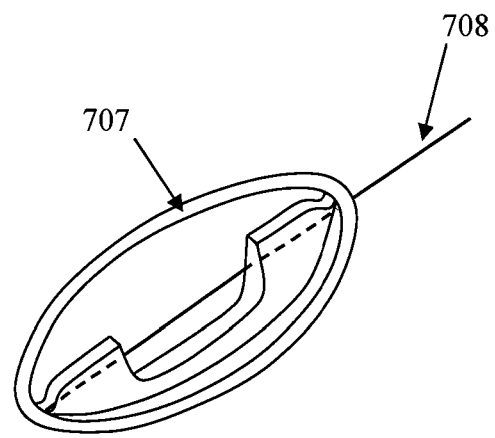
FIGS. 7B and 7C depict a suction member where the peripheral rib is collapsible or inwardly distortable, shown in its non-collapsed and collapsed state respectively.
Figure 7C:
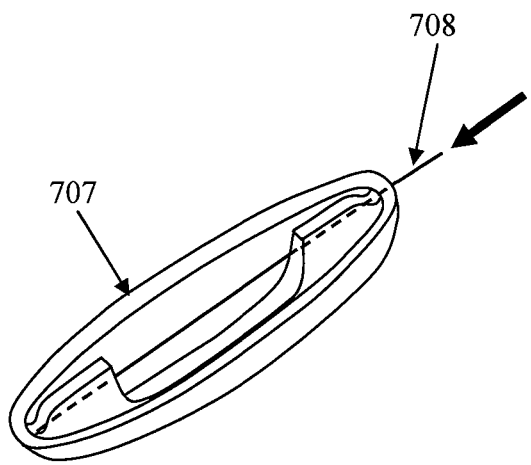

The ribs may also comprise or have one or more discrete members or features thereon, as will be described in greater detail below. The joining or peripheral ribs may also be collapsible, movable, or otherwise articulatable to provide greater maneuverability of the suction member along the tissue, or to enable gripping of tissue after the vacuum has been turned off. For example, the peripheral rib may be collapsible or inwardly distortable to capture tissue between its edges, as shown in FIGS. 7B and 7C. In this variation, the peripheral rib (707) distorts or collapses inwardly upon pushing wire (708). Of course, the peripheral rib (707) may be distortable by other mechanisms as well (e.g., pull wire, shape memory actuation, etc.). Also, while FIGS. 7B and 7C show a variation where the peripheral rib (707) is distorted in an elongated fashion, the peripheral rib may also be distorted in a lateral fashion, or an inwardly radial fashion.

Figure 7D:
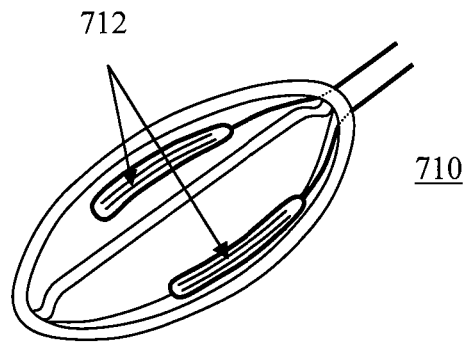
FIG. 7D shows a variation of a suction member having tongs to capture tissue therebetween.
Figure 7E:
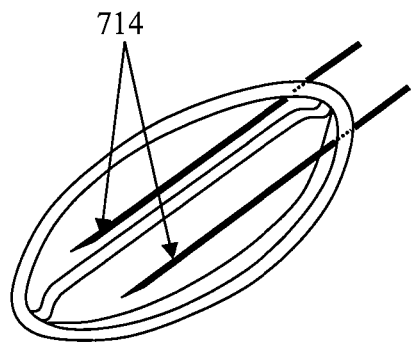
FIG. 7E shows a variation of a suction member having needles to puncture tissue.

FIG. 7D shows a variation of suction member (710) having tongs (712). One or both of the tongs may be actuatable, and the tongs may be actuatable in any suitable fashion (e.g., push-pull wire, etc.). This variation may be useful to capture or clamp tissue after the vacuum has pulled the tissue into the suction member cavity. While tongs are shown here, any suitable type of clamping, or gripping mechanism may be used. Of course, any of the suction members described here may have any number of clamping or gripping mechanisms. FIG. 7E is a similar variation to FIG. 7D, but here having needles (714) to puncture and hold tissue, instead of tongs (712).

Figure 8A:
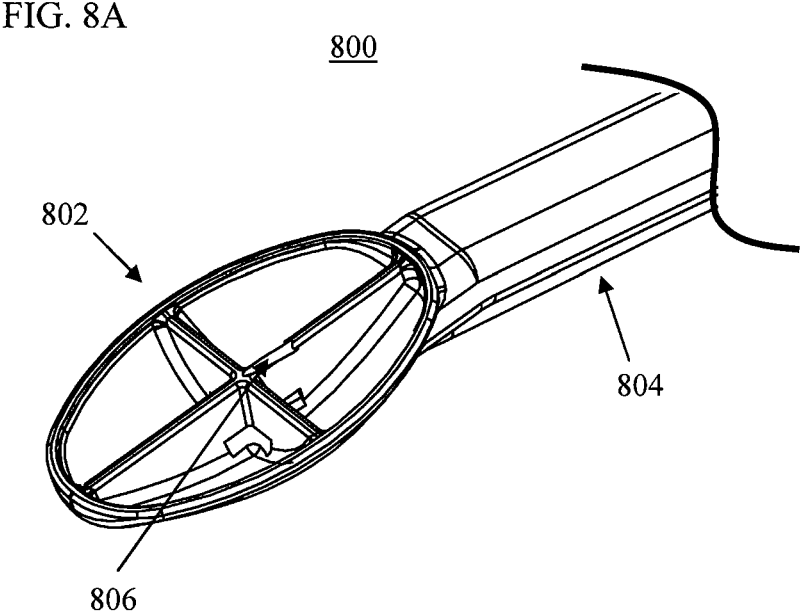
FIGS. 8A and 8B provide an illustration of tissue-piercing member deployment when the tissue-piercing member exits within or through the suction member.
Figure 8B:
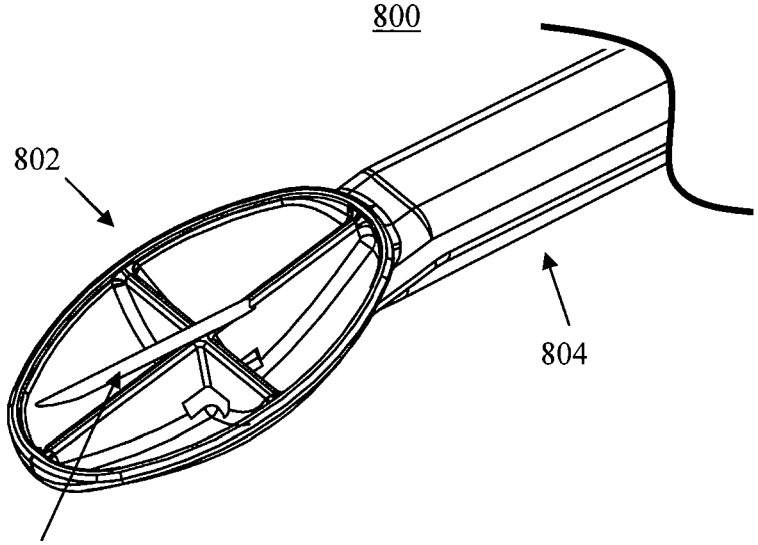

FIGS. 8A and 8B provide an illustration of tissue-piercing member deployment when the tissue-piercing member exits within or through the suction member. That is, in contrast to those devices described above where the tissue-piercing member exits immediately adjacent the suction member, the tissue-piercing member shown in FIGS. 8A and 8B exits within the suction member itself. Of course, it should be understood that (while not shown in FIGS. 8A and 8B), the elongate member may comprise or define one or more ports immediately adjacent to the suction member for one or more purposes unrelated to tissue-piercing members, as described above. Shown in FIG. 8A is device (800) comprising a suction member (802) and elongate member (804). As described above, the tissue-piercing member (806) in this variation exits within the suction member (802). FIG. 8B shows tissue-piercing member (806) being further deployed. This for example, may be effected via the use of one or more pull wires or other controls, or manually by the user advancing the tissue-piercing member (806) distally.

Figure 8C:
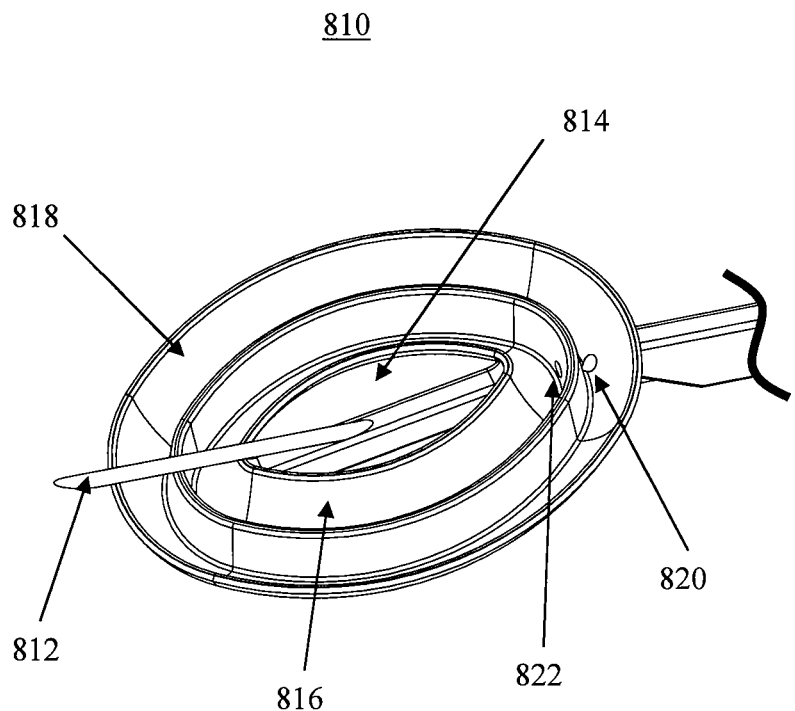
FIG. 8C shows a variation of a suction member where the tissue-piercing member exits within or through the suction member, where the suction member is toroidal or donut shaped defining one or more apertures therethrough.

FIG. 8C shows another variation of a suction member (810), where the tissue-piercing member (812) exits within the suction member cavity. A device of this configuration may help facilitate tissue traction as the device is moved along tissue. In this variation, the suction member (810) is generally donut shaped, or generally toroidal and defines a central opening or aperture (814). The suction member (810) of this variation comprises two toroidal shaped cavities (816, 818), which may be of the same or different height or depth, and which may independently be configured to allow for a particular volume of tissue therein. The device of this variation also comprises main vacuum port (820) connected via opening or conduit to inner vacuum port (822). In this way, suction may be facilitated about both toroidal cavities (816, 818). Of course, the suction member (810) may include any number of suitable vacuum or suction ports, placed at any suitable location, as described above. Importantly, the toroidal shape of the suction member is just one shape that may be used with the devices described herein. As described hereinthroughout, the suction member may have any suitable geometry.

Figure 9A:
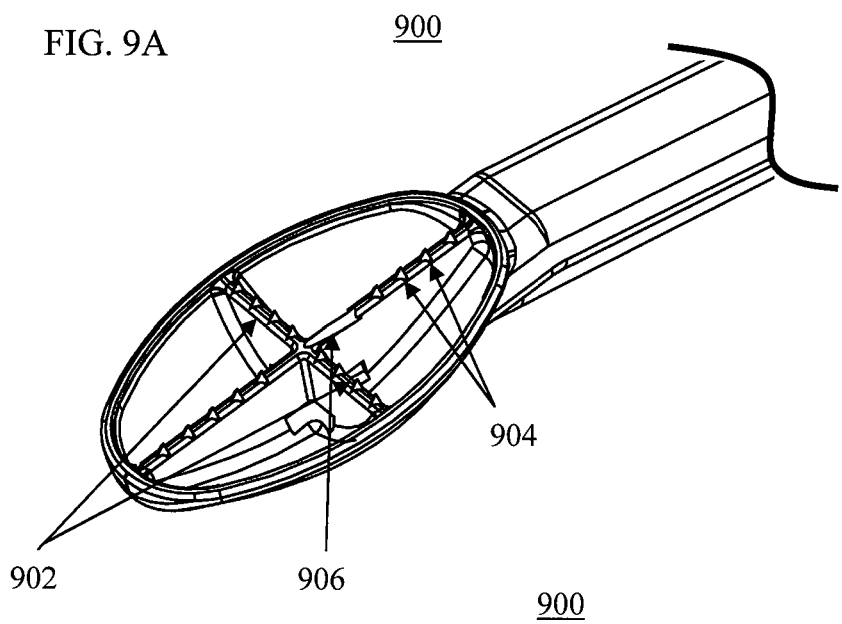
FIGS. 9A and 9B provide an illustration of tissue-piercing member deployment when the tissue-piercing member exits within or through the suction member, where the tissue apposition members have one or more traction members thereon.
Figure 9B:
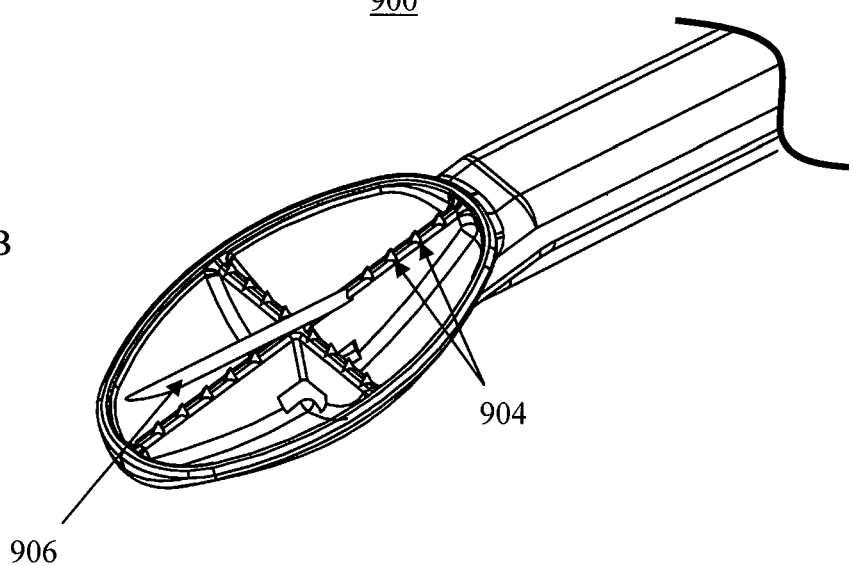
Figure 9C:
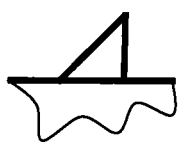
FIGS. 9C-9F depict illustrative traction members.
Figure 9D:
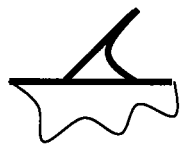
Figure 9E:
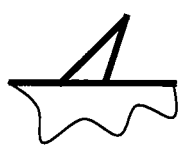
Figure 9F:

FIGS. 9A and 9B are similar to FIGS. 8A and 8B except that the device (900) of FIGS. 9A and 9B comprise tissue apposition members (902) having one or more traction members (904) thereon. This may be useful, for example, to increase tissue apposition and traction without having to alter the number of ribs or particularly select their geometry, and may be particularly useful or helpful during deployment of the tissue-piercing member. The traction members themselves may have any suitable geometry, size, or configuration, and may be made of, or coated with, any suitable material. Illustrative traction members are shown, for example, in FIGS. 9C-9F. Any of the traction members may have one or more ports, lumens, or apertures for delivery of agents or fluids therethrough. In this way, the traction members may additionally be used to locally deliver drugs (e.g., antibiotics for local sterilization purposes, etc.) or to flush the tissue adjacent to the traction members and/or suction member. It should be understood that while the suction member shown in FIGS. 9A and 9B only have traction members on the joining ribs, it should be understood that traction members may also be placed along or about the peripheral rib, in any suitable location or fashion.

Figure 9G:
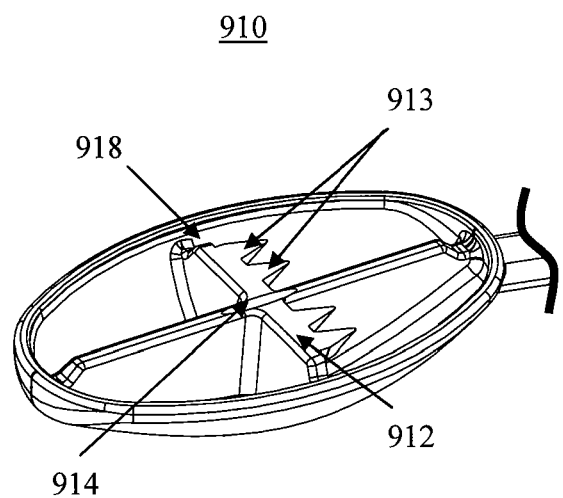
FIGS. 9G and 9H provide an illustration of tissue-piercing member deployment when the tissue-piercing member exits within or through the suction member, where the tissue suction member comprises a ridge having one or more teeth.
Figure 9H:
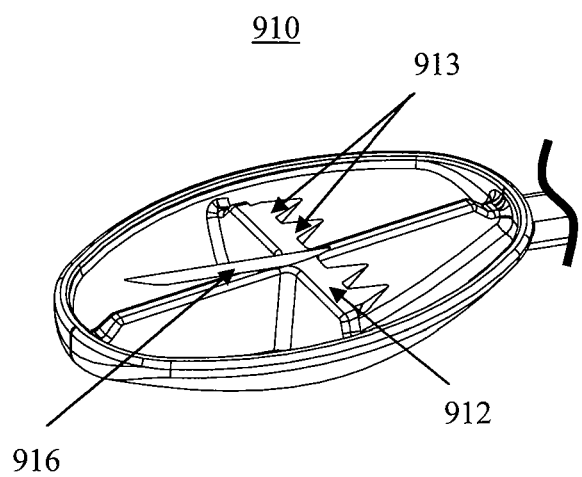

FIGS. 9G and 9H show an alternative variation of a tissue suction member (910), here having a ridge (912) with teeth (913). Also shown in this variation is tissue-piercing member exit port (914, FIG. 9G) and tissue-piercing member (916, FIG. 9H) advanced out of tissue-piercing member exit port (914). In this variation, tissue may fold around and/or underneath ridge (912) when suction is applied, as shown in FIG. 9I (here shown with two tissue layers 920, 922). In this way, traction and gripping of tissue may be enhanced as the edge of the teeth (913) provide a tortuous path for the tissue to cross, while clogging of the suction port or ports may be mitigated, as previously described. This variation may be particularly useful when the devices are used with tissue that is slippery, amorphous, mucousy, or otherwise difficult to manipulate. Additionally, as with all variations having teeth described hereinthroughout, the teeth (913) may be oriented in any suitable manner. For example, the teeth (913) may be oriented in a direction that opposes the direction of the tissue-piercing member as it is advanced into tissue. Having a space (918) between the outer rim of the suction member and the ridge (912) may help to further increase the ability of the tissue to collapse about the ridge (912) and further enhance the robustness of the vacuum seal by minimizing the disruption of the tissue during normal amounts of manipulation (or handling) that could otherwise lead to a vacuum leak.

The orientation and or geometry of the ridge (912) may be modified to affect more or less tissue capture in the suction member cavity. Similarly, the number and geometry (length, width, shape, etc.) of the teeth may be modified as desirable to affect tissue capture. For example, the ridge may include one tooth, two teeth, four teeth, six teeth, or even more teeth, and these teeth may be inwardly biased or outwardly biased, and may have any suitable shape. The teeth (913) need not be made from the same material as the ridge (912), and the teeth may or may not be planar with the ridge (912). The ridge (912) may be made from a single molded piece of material, as generally shown in FIGS. 9G and 9H, or may be made from a separate piece of material, and then clamped, welded, glued, or otherwise fastened or affixed to the suction member. Of course, the ridge may be made of any suitable biocompatible material (e.g., stainless steel, plastic, combination of materials, etc.).

Of course, when ridges are used in combination with the suction members described herein, they may be articulatable, controllable, tiltable, disengageable, or otherwise moveable. For example, FIG. 9J and FIG. 9K, depict one variation of a ridge (912') that is articulatable or rotatable within the suction member cavity. In this way, teeth (913') disengage from the tissue (shown in FIG. 9K), which may help the suction member release tissue that has been captured therein. This may be useful, for example, when attempting to remove, withdraw, or reposition the device. For example, in some variations, vacuum or suction may be maintained after the ridge (912') has been rotated into the suction member cavity so that the device can be translated along the approximated tissue surface. Once the device has been advanced to a second location, the ridge (912') may be redeployed or rotated back to its original position in order to "lock" onto or into or otherwise engage captured tissue. The ridge (912') may be actuated or rotated or otherwise controlled in any suitable manner. For example, one or more push-pull wires, spring(s) acting about the axis of articulation in conjunction with a pull-wire, pneumatic or hydraulic actuation, or the like. Of course, the rotatable ridge described here is just one variation of a suitable ridge. As described herein throughout, any moveable ridge, having any of the features described here may be used with the devices and methods described here. One specific alternative variation of a moveable ridge is described in FIG. 9N below.

Figure 9L:
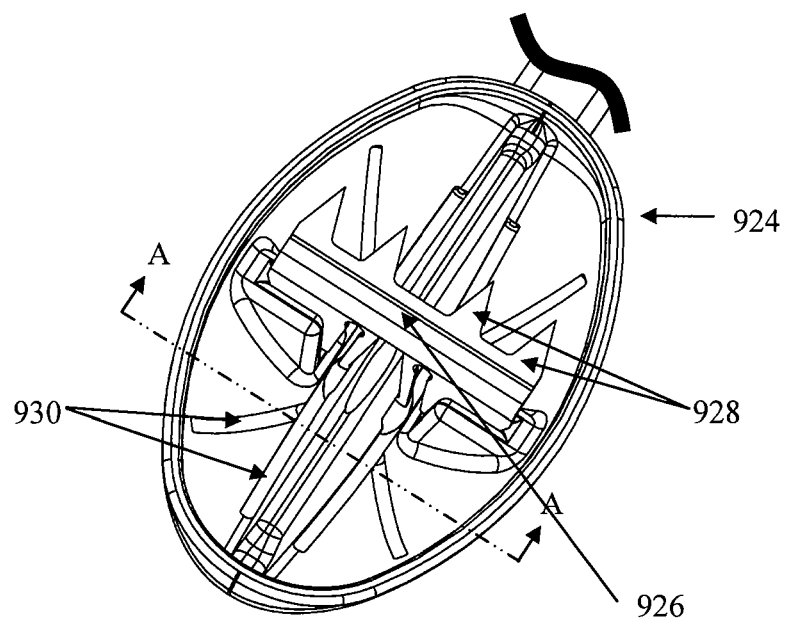
FIG. 9L depicts an illustrative suction member comprising a ridge having teeth and also channels for distributing vacuum.
Figure 9M:
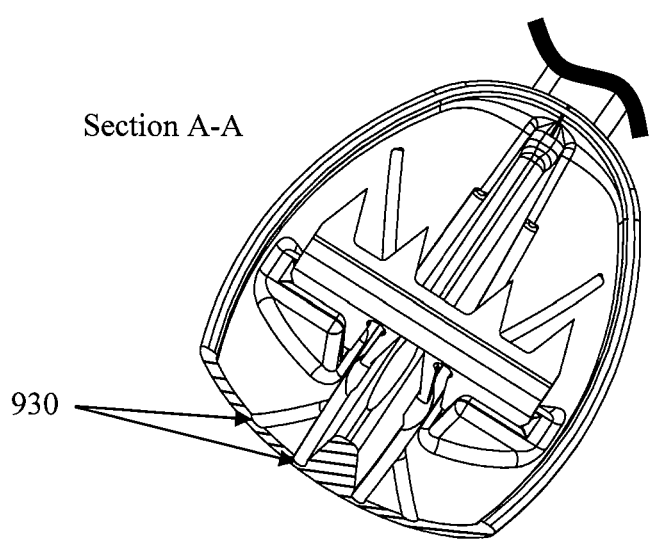
FIG. 9M is a cross-sectional view of the device of FIG. 9L taken along line A-A to better illustrate channels for distributing vacuum.
Figure 9N:
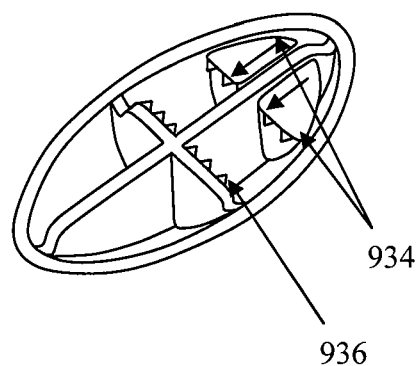
FIG. 9N shows a variation of a suction member having one or movable members to clamp tissue therebetween where the members are in the form of ridges with teeth.

FIG. 9L depicts another variation of a suction member (924) having a ridge (926) with one or more teeth (928) thereon, where the suction member (924) has one or more channels (930) therein. FIG. 9M provides a cross-sectional view of the device of FIG. 9L taken along line A-A. This variation functions similarly to the variation of FIG. 9G described just above, with the addition of having channels. The channels may be useful, for example, to facilitate (or deliver and/or distribute) vacuum or suction, or delivery or collection of fluid, as will be described, e.g., with respect to FIGS. 15B and 15C below. Of course, the channels (930) may be used in conjunction with one or more ports located along or within the suction member to provide for delivery of one or more useful fluids (e.g., therapeutic, sterilization, flushing, etc.), as described hereinthroughout. FIG. 9N depicts yet another variation of a suction member (932), here having one or more moveable ridge members (934) to facilitate capture of tissue. As with the devices described just above, members (934) may have any number of teeth (936), may have any suitable geometry, and may be made of any suitable material.

Figure 9P:
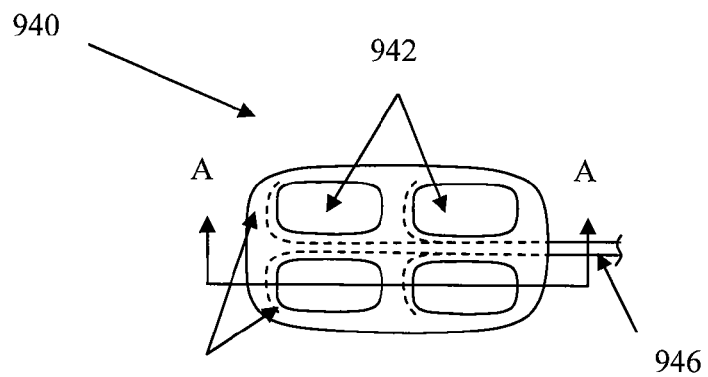
FIGS. 9P and 9Q are cross-sectional views of the suction member of FIG. 9O depicting how tissue may be captured against one ore more walls defining the windows or apertures.
Figure 9Q:
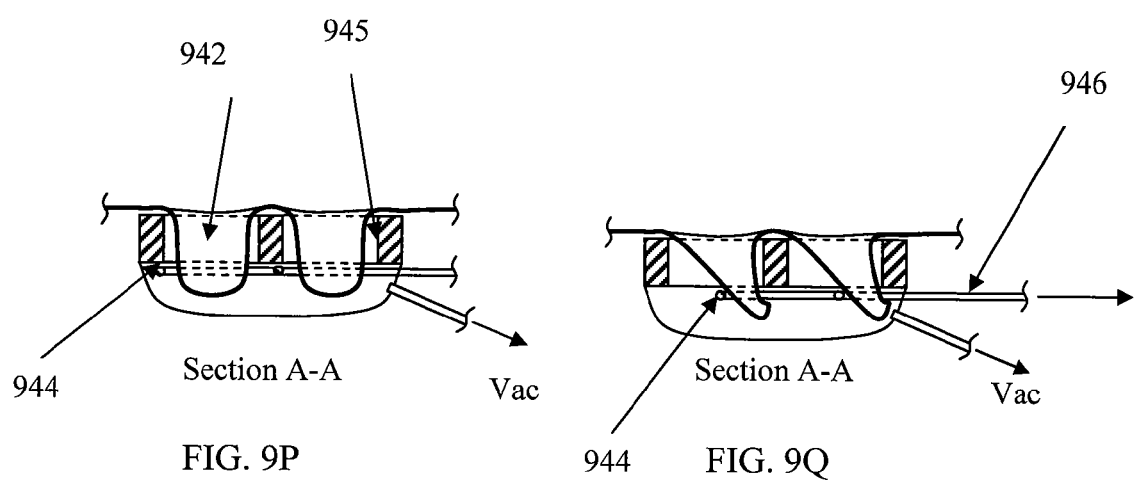

FIGS. 9O-9Q depict another variation of a suitable suction member, here having one or more apertures or windows for capturing tissue thereagainst. Specifically, FIG. 9O depicts the basal surface of a suction member (940) where the basal surface defines a series of apertures or windows (942). In this variation, four apertures are provided, but any suitable number of apertures may be used, and they may have any geometry and be oriented about the basal surface in any fashion. Also shown in FIG. 9O are arms (944) which when articulated pull tissue against one or more of the aperture walls (945) thereby capturing tissue. This variation may be particularly useful when it is desirable to capture or accommodate excess tissue. This variation may also be particularly useful when used with thin tissue or tissue of a tubular organ or the like. FIGS. 9P and 9Q are cross-sectional representations of the suction member of FIG. 9O taken along line A-A where the arms are in an initial and actuated state respectively. As depicted by those figures, as push-pull wire (946) is withdrawn proximally, arms (944) move proximally and pull tissue against one or more walls (945) of the apertures (942). Of course a push-pull wire (946) is just but one way to actuate arms (944). Any suitable actuation mechanism may be used. Once the tissue has been captured in this fashion, a tissue-piercing member (not shown) may be advanced through the tissue in the same or opposite direction as the tension applied to the captured tissue.

Figure 9R:
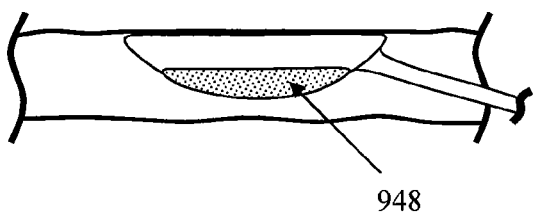
FIGS. 9R-9U depict how an expandable or other tissue-contacting member may be used to contact or engage tissue opposite the basal surface of the suction member so that tissue may be stretched across the basal surface of the suction member.
Figure 9S:
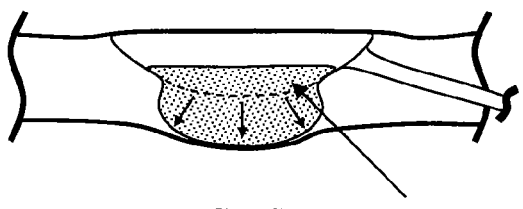
Figure 9T:
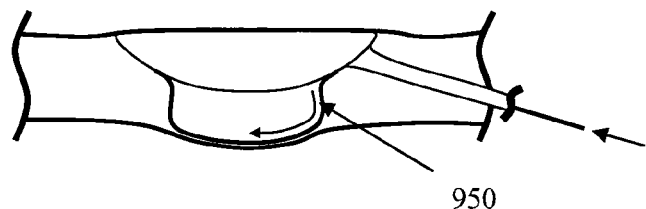
Figure 9U:
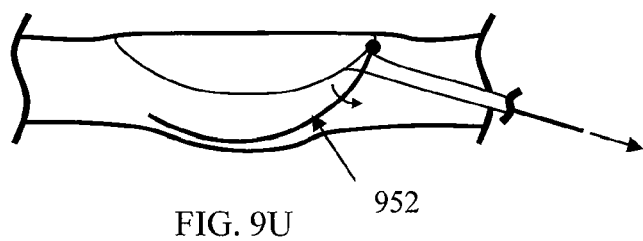

FIGS. 9R-9U depict various alternative ways to accommodate excess tissue, and as with the variations described just above, these variations may be particularly useful when dealing with thin tissue, tissue of a tubular or small geometry organ, or the like. In general, in these variations, an expandable member or other tissue-contacting member is actuated or activated so that it abuts, contacts, or apposes tissue opposite the basal surface of the suction member. In this way, excess tissue is displaced and target tissue becomes taught or tensioned across the basal surface of the suction member, resulting in better tissue capture. The variation shown in FIGS. 9R and 9S is an expandable member (948) in its unexpanded and expanded state respectively. The expandable member (948) may be any suitable expandable member. For example, it may be a balloon, expandable polymeric member, etc., which may be expanded in any suitable fashion, e.g., pressurized saline, water, air, etc. FIG. 9T depicts another variation of an expandable or articulatable member, here shown as an expandable wire or strut (950). The wire may be made of any suitable material. FIG. 9U shows yet another variation of an articulatable member, in this case, a rotatable or articulatable arm (952). Again, the arm (952) may be made of any suitable material.

Figure 10A:
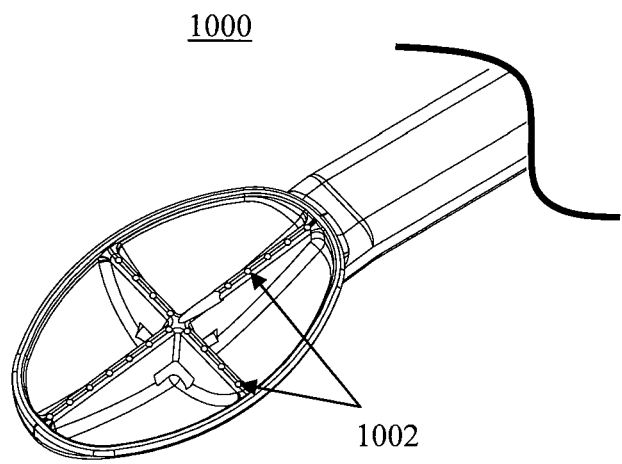

FIGS. 10A-10D provide additional variations of suction members. FIG. 10A shows suction member (1000) from the underside, where the suction member is shown having a number of discrete features (1002). Features (1002) may be one or more heating elements, one or more electrodes (e.g., for delivering energy, such as RF, ultrasound, light, magnetic, combinations of the foregoing, etc.), one or more sensors (e.g., Doppler sensor, pressure sensor, temperature sensor, and the like), one or more radio-opaque markers to facilitate visualization, a camera to facilitate direct visualization, one or more ports, etc. The features may be placed in accordance with a predetermined pattern or be placed randomly along or about the suction member or its tissue apposition members. The spacing between the features may be uniform, as shown in FIG. 10A, but need not be. Similarly, the features need not have a uniform size or shape. Any number and combination of features may be used.

Of course, while a camera has been described here as a potential feature, it should be understood that a camera with or without a corresponding light or illumination source, may be placed on the device at any suitable location to facilitate direct visualization of the tissue (e.g., located at a position along the elongate member). This may be particularly useful, for example, when the device is used as stand alone device, and not introduced through an endoscope, gastroscope, or other similar sheathed structure that provides for visualization of the working area. Methods for using the devices described here, alone or in combination with sheathed structures, will be described in more detail below.

Figure 10B:
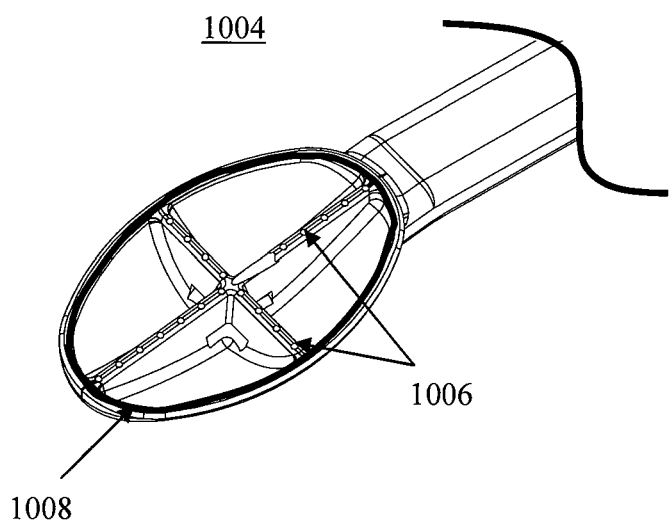

FIG. 10B depicts a device (1004) similar to the device (1000) of FIG. 10A, except that the device (1004) of FIG. 10B has an additional peripheral feature (1008). The peripheral feature (1008) may be any of those features described just above, e.g., heating elements, electrodes, sensors, ports, illumination, etc., or some combination thereof. In some variations, feature (1008) is an electrode for delivering energy for ablation or sealing, while features (1006) comprise one or more sensors for sensing one or more useful parameters (e.g., temperature, pressure, movement, such as blood flow, etc.). Of course, the features need not be different from one another. For example, feature (1008) may be of the same general nature as features (1006) (for example, both features may be for sensing). Similarly, feature (1008) may be of the same general nature as features (1006), where the two features are used in concert to accomplish a particular task. For example, feature (1008) and features (1006) may both be electrodes that may be used separately or in concert to detect, sense, or measure a particular tissue parameter or property (e.g., resistance, impedance, conductivity, capacitance, or the like). The features may be oriented in any suitable or desirable way to map, sense, detect, measure, etc., any suitable or desirable tissue parameter or property. Of course, these are just a few illustrative examples. It should be understood that any combination of the described features may be used.

Figure 10C:
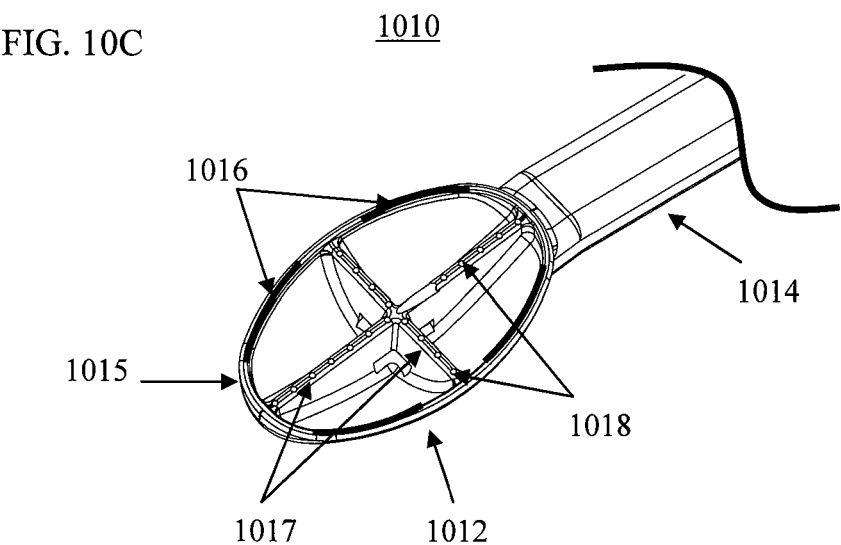
Figure 10D:
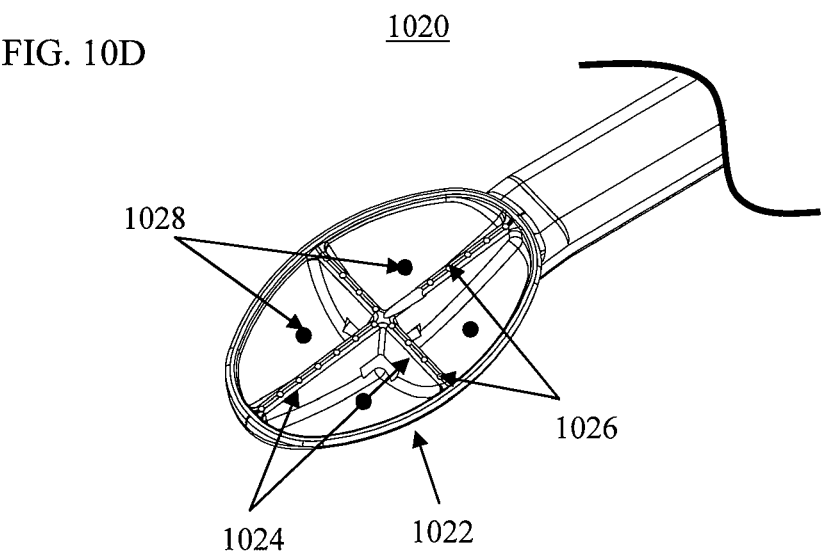

FIGS. 10C and 10D provide additional depictions of feature locations and configurations within and about the suction member. FIG. 10C shows a device (1010) comprising a suction member (1012) and an elongate member (1014). The suction member (1012) comprises tissue apposition members in the form of ribs, having features thereon. The peripheral rib (1015) has four discretely located features (1016) and the joining ribs (1017) have a plurality of discretely located features (1018) thereon. In FIG. 10D, the suction member (1022) of device (1020) comprises a tissue apposition member in the form of ribs, having features thereon, as well as having features along an inner surface of the suction member (1022). Specifically, shown there are joining ribs (1024) having a plurality of discretely located features (1026) thereon, and features (1028) located along an inner surface of the suction member (1022). Again, the features may be any of those features described above, and may be of any suitable number, size, shape, or configuration.

Figure 11A:
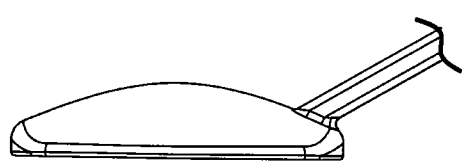
FIGS. 11A-11D provide illustrative variations of elongate member-suction member attachments, detailing various suitable angles of attachment.
Figure 11B:
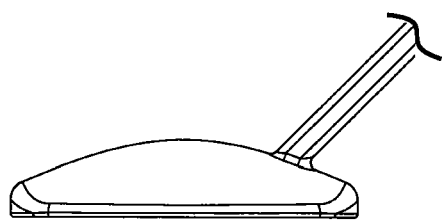
Figure 11C:
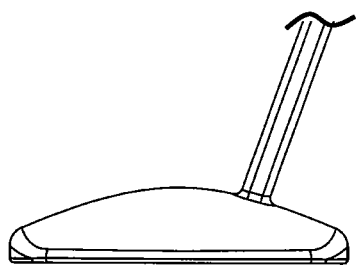
Figure 11D:
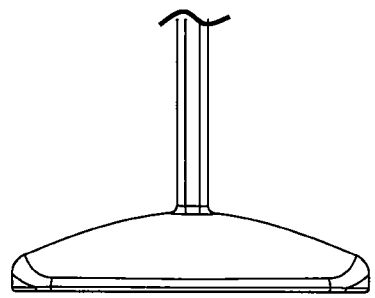

FIGS. 11A-11D provide illustrative variations the angle of attachment between an elongate member and a suction member. Shown there are the various angles of connection or attachment, from substantially acute, as shown in FIG. 11A to perpendicular as shown in FIG. 11D. The angle of attachment may be selected depending on the indication or use. For example, in some instances it may be quite desirable to have the suction member positioned so that it is relatively isolated from the elongate member and the attachment point. In this way, the suction member is free to move about or traverse tissue without interference from the elongate member or the attachment point, for example as shown in FIGS. 11C and 11D. Of course it should be appreciated that the attachment angle may be selected to accomplish a particular or desired angle of approach (e.g., based on tissue location), may be selected to help facilitate ergonometric use of the device, may be selected to help facilitate control of the device, or may be selected based upon some combination of these factors. In addition, it should be understood that the elongate member need not be attached in a perpendicular or substantially perpendicular to the surface of the suction member. Indeed, the attachment itself may be angled or straight, with any amount of lateral displacement from the basal surface of the device.

Devices having more than one suction member are also contemplated. For example, the device may comprise two, three, four, five, or even more suction members. In some variations, the device comprises two suction members, as shown for example, in FIGS. 12A and 12B. In general, at least one of the suction members is movable with respect to the other suction member, and in some variations, both suction members are movable with respect to one another. These variations may be particularly useful when clamping tissue between two surfaces is helpful or required, e.g., with thin, soft, or flexible tissue such as stomach or intestinal wall tissue.

Each suction member may be connected to an elongate member, or only one suction member may be coupled to the elongate member, and the suction members may be coupled to the elongate member in any suitable fashion. In some variations, the one or more suction members are coupled to the elongate member via a flexible portion, which in some instances may be a hinge. The suction members of these variations may have any suitable geometry, and may comprise or include, any of the features or any combination of the features (traction members, apposition members, electrodes, sensors, cameras, light sources, etc.) described above.

Figure 12A:
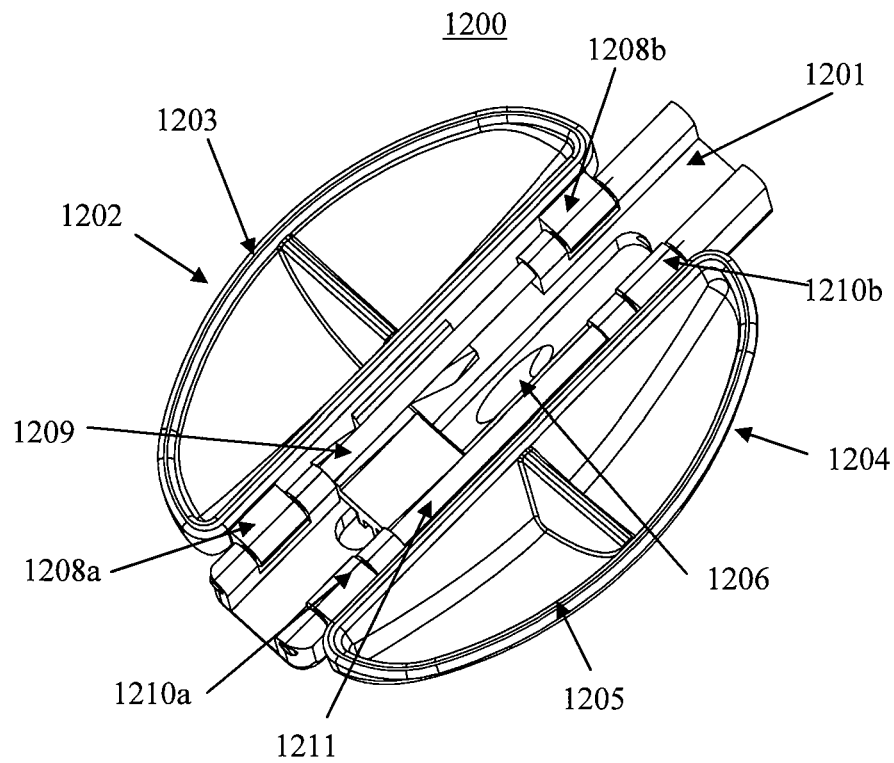
FIGS. 12A and 12B depict one variation of a device having two suction members, shown in an open and collapsed configuration respectively.
Figure 12B:
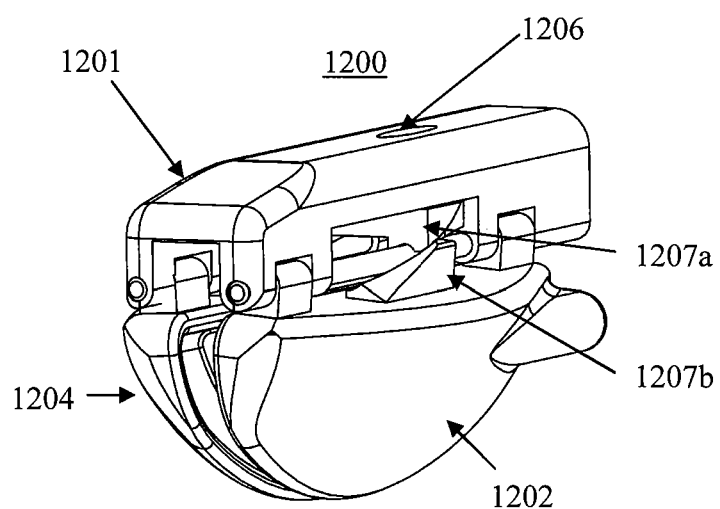

Turning now to the figures, FIGS. 12A and 12B depict one variation of a device (1200) having two suction members (1202, 1204), here, shown in an open and collapsed configuration respectively. The suction members may transition between their collapsed and expanded configuration by movement of a slidable actuator having any particular geometry (e.g., a helical cam structure (1207a, 1207b), a wedged cam structure, a push-pull wire, or the like). In this variation, suction members (1202, 1204) have basal surfaces that are generally semi-elliptical in shape, although, the suction members may have any suitable geometry as described above.

Tissue apposition members are also shown, and in this variation, are in the form of ribs (1203, 1205).

In this variation, each suction member is connected to the elongate body (1201) via a hinge mechanism. Specifically, retention pin or shaft (1209) is retained by retaining tabs (1208a and 1208b), leaving the suction member (1202) free to rotate about pin (1209). Suction member (1202) is thus moveable with respect to both the elongate member (1201) and suction member (1204). In this variation, suction member (1204) is also moveable with respect to the elongate member (1201) and suction member (1202). In a corresponding manner to suction member (1202), here, pin or shaft (1211) is retained by retention tabs (1210a and 1210b). Of course, other hinge mechanisms may also be used e.g., single or multiple flexure joints, revolute joints, molded plastic live hinges, ball and socket joints, slidable tubes with counter-opposed flexure elements, etc. Also shown in these figures is tissue-piercing member exit port (1206). Again, it should be understood that FIGS. 12A and 12B are merely illustrative. Finally, it should be understood that any of the devices or tools described herein may be robotically operated or used in combination with robotic devices or systems.

II. Methods

Methods of using devices for forming tracts in tissue are also described here. In accordance with some methods, a device having one or more suction members is advanced adjacent to tissue, suction is applied to draw tissue against the one or more suction members, and then a tissue-piercing member is advanced through the drawn tissue to form a tract in or through the tissue. The device may be advanced to the target tissue site using any suitable devices and/or methods. As an example, in some variations, the device may be disposed within a lumen of a trocar, and the trocar may be advanced to the target tissue site. Once at the target tissue site, the device may be deployed from the trocar and used to form a tissue tract. As another example, in some variations the device may be relatively small and easy to navigate, and may be advanced through tissue without being positioned in any other devices. In some such variations, the device may include one or more regions (e.g., edges) that are sharpened, serrated, etc., such that the device may relatively easily cut a path through tissue surrounding the target site. In certain such variations, the device may include one or more relatively rigid portions (e.g., to provide enhanced pushability). Devices may in some cases be guided to a target tissue site using one or more imaging techniques, such as ultrasound, and/or using one or more localization techniques (e.g., by measuring blood flow with vascular Doppler).

The device may be, for example, any of the devices described above. For example, the device may comprise one or more suction members, one or more energy applicators (e.g., ultrasound, RF, light, magnetic, combinations thereof, etc.), one or more sensors (e.g., to sense temperature, pressure, blood flow, combinations thereof, etc.), more than one tissue-piercing member, etc. The suction members may have any of the above described features. When devices having more than one suction member are used, the devices may be advanced when the suction members are in their open configuration, collapsed configuration, or some intermediate configuration therebetween. It should be noted that some variations of devices may not comprise any suction members, and/or some variations of methods may not include applying suction to tissue. For example, a device may be used to form a single self-sealing tract in tissue by advancing only a tissue-piercing member through the tissue, and without applying any suction to the tissue.

The methods described here may be used to form tracts in any tissue in connection with any technique or procedure. The tissue may be any tissue where it is desirable to form a tract therethrough. For example, it may be tissue of the cardiovascular system, digestive system, respiratory system, excretory system, reproductive system, nervous system, etc. In some variations the tissue is tissue of the cardiovascular system, such as an artery, or a heart. In other variations the tissue is tissue that is accessed through a natural orifice (e.g., to perform natural orifice translumenal endoscopic surgery "NOTES"), such as tissue of the reproductive system, excretory system, digestive system, or the like. Of course, it should be understood that methods of forming multiple tracts in tissue, whether through similar or different tissue, are also contemplated.

As will be described in more detail below, the methods may include creating a tract that self-seals within a period of time (e.g., 15 minutes or less, 12 minutes or less, 10 minutes or less, 5 minutes or less, 3 minutes or less, 1 minute or less, etc.). Of course, tracts that may otherwise self-seal after a period of time may be nevertheless have sealing expedited by other mechanisms as well (e.g., application of mechanical pressure, application of suction, application of one or more sealing agents, etc.). The methods may also comprise application of energy, delivery of one or more fluids or useful agents, delivery of one or more useful tools to a tissue site, performing a procedure, visualization, determining the location of the device with respect to the tissue, combinations thereof, and the like. The device may be rotated, repositioned, or otherwise manipulated during these methods, as will be described below.

Figure 13A:
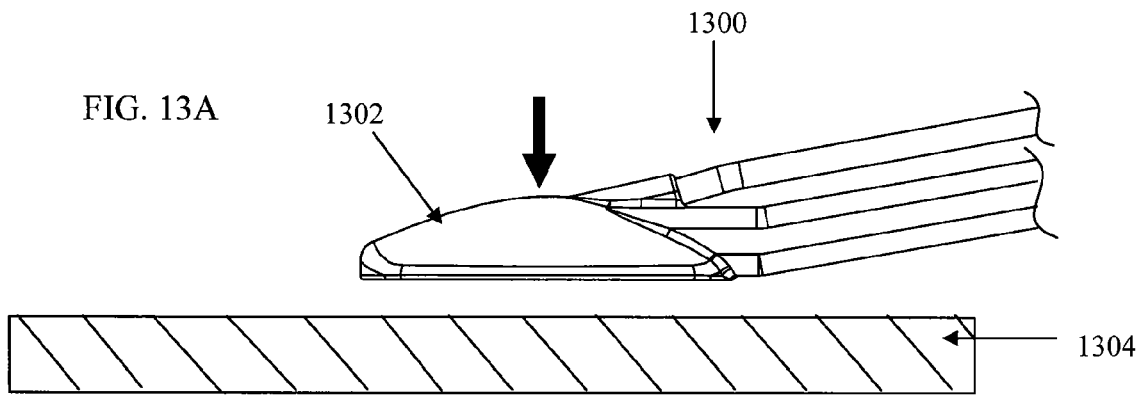
FIGS. 13A-13M depict an illustrative method for forming a tract in or through tissue with FIGS. 13G and 13H specifically depicting suitable distal expandable features of a guide wire for use with the methods described herein.
Figure 13B:
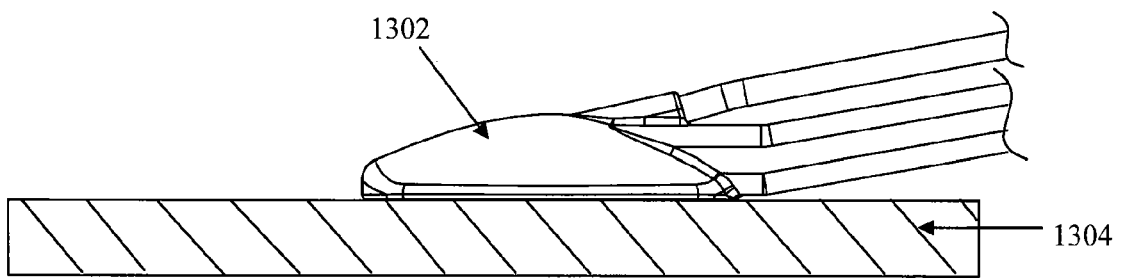
Figure 13C:
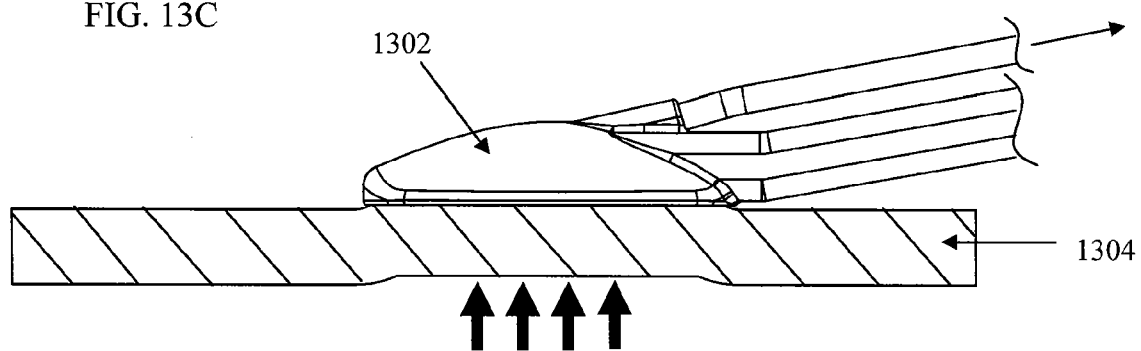

With specific reference now to the figures, FIGS. 13A-13M depict one illustrative method for forming a tract in tissue. As shown in FIG. 13A, device (1300) comprising one or more suction members (1302) is advanced adjacent to tissue (1304). Suction may then be applied to the suction member so that the suction member is pulled toward the tissue until it contacts the tissue, as shown in FIG. 13B, and against the suction member as shown by the arrows in FIG. 13C. Of course, suction may be applied at any stage of the method. For example, suction may always remain on, and the device may be advanced while suction remains on. Conversely, the device may be advanced adjacent to tissue and then suction applied, as shown here. Alternatively, suction may be toggled on and off, regulated, or otherwise modulated, to control the vacuum strength or flow using, e.g., any of the proximal controls described hereinthroughout.

Figure 13D:
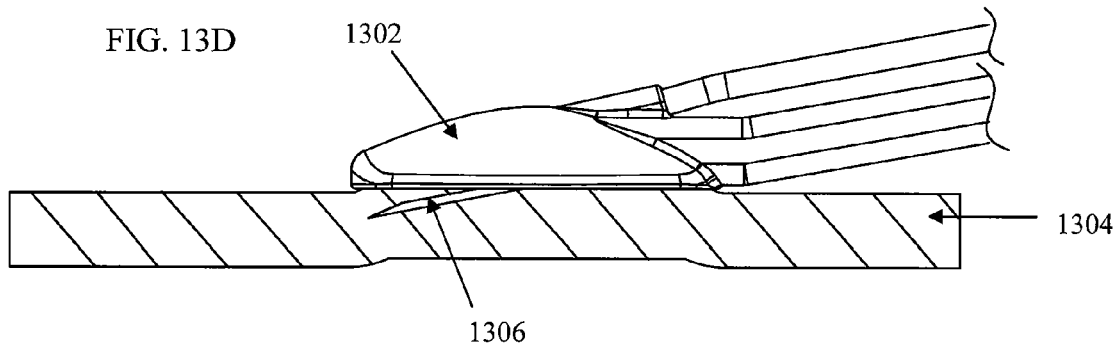
Figure 13E:
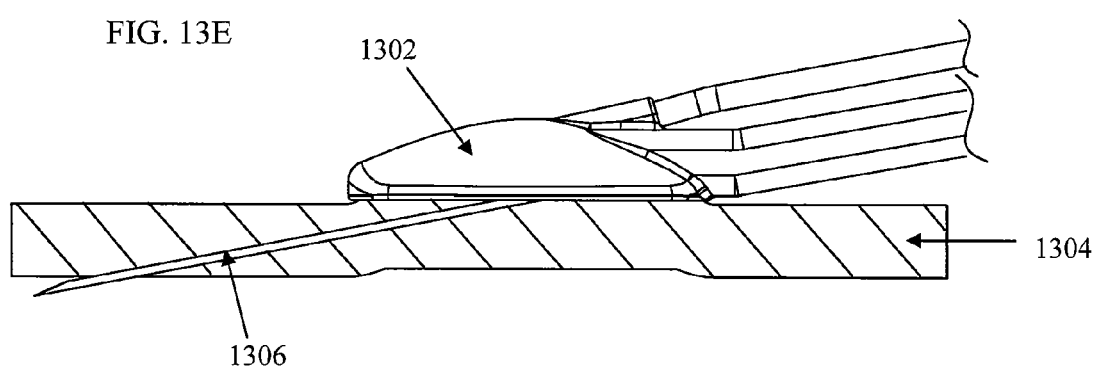
Figure 13F:
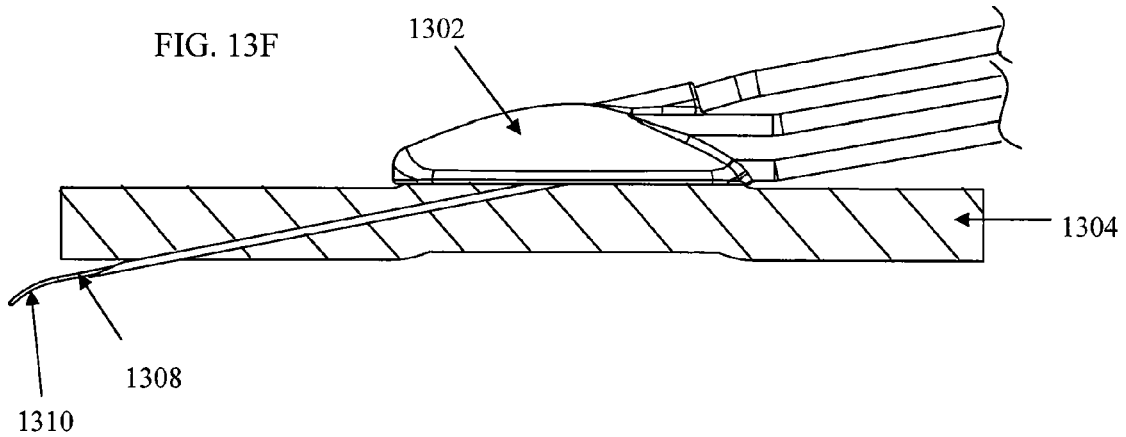

Returning to the figures, once the tissue has been drawn against the suction member, a tissue-piercing member may be advanced through the drawn tissue to form a tract in the tissue as shown in FIG. 13D. The tract may be of any length, and may traverse through the tissue as shown in FIG. 13E. Once a tract has been formed, one or more tools may be advanced through the tract. For example, in FIG. 13F, a guide wire (1308), may be advanced through the tissue-piercing member, and through the tract.

Figure 13G:
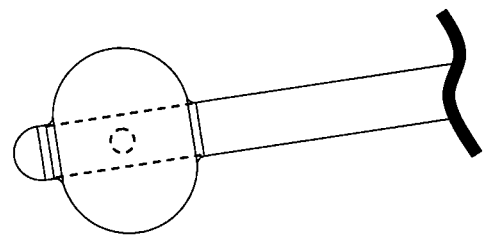
Figure 13H:
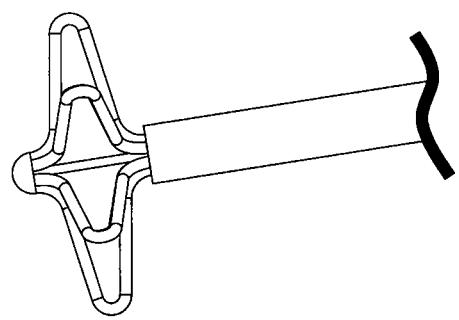
Figure 13I:
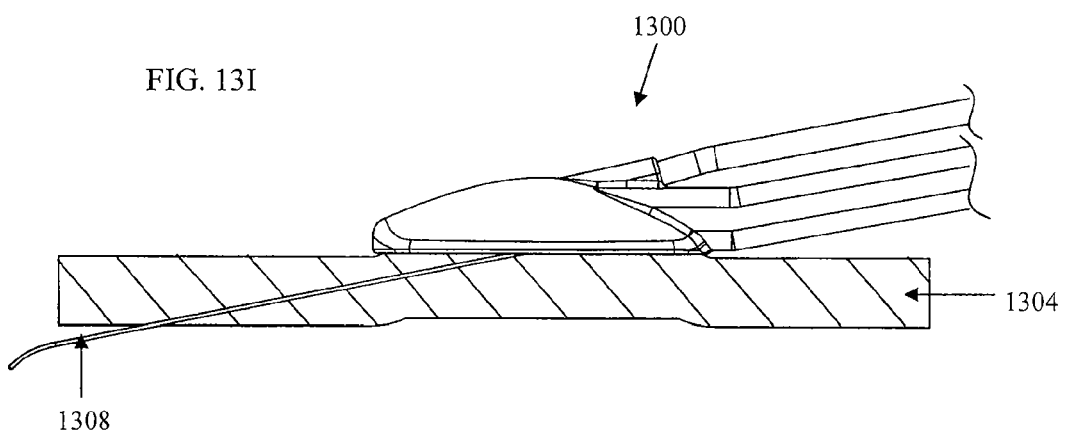

The guide wire (1308) may be any guide wire having a diameter suitable for use with the corresponding tissue-piercing member (1306). The guide wire (1308) may also have one or more expandable members (e.g., expandable balloon as shown in FIG. 13G, expandable cage or flower wire formation as shown in FIG. 13H, expandable arms, etc.) or similar such features on its distal end (1310). In this way, the distal end of the guide wire may be used to help locate or position the device with respect to the tissue and to maintain its position for a portion of the procedure. For example, the guide wire (1308) may be advanced through the tissue (1304), and the distal expandable feature expanded. The guide wire (1308) may then be gently pulled proximally, (i.e., in the direction of the tissue). Once the expandable member abuts the tissue (as determined via tactile feedback, for example), the location of tissue has been determined and this information may be used as a guide for the rest of the procedure. Of course, these tissue location methods may not be necessary when indirect (e.g., fluoroscopic guidance, ultrasound, etc.) or direct (e.g., camera, scope, etc.) visualization is employed, which visualization techniques may be used with any of the methods described here. Vacuum checks may also be useful in determining the location of the tissue, or the device with respect to tissue. An additional useful method for determining the location of tissue is described in more detail below with respect to FIGS. 13N-P.

Figure 13J:
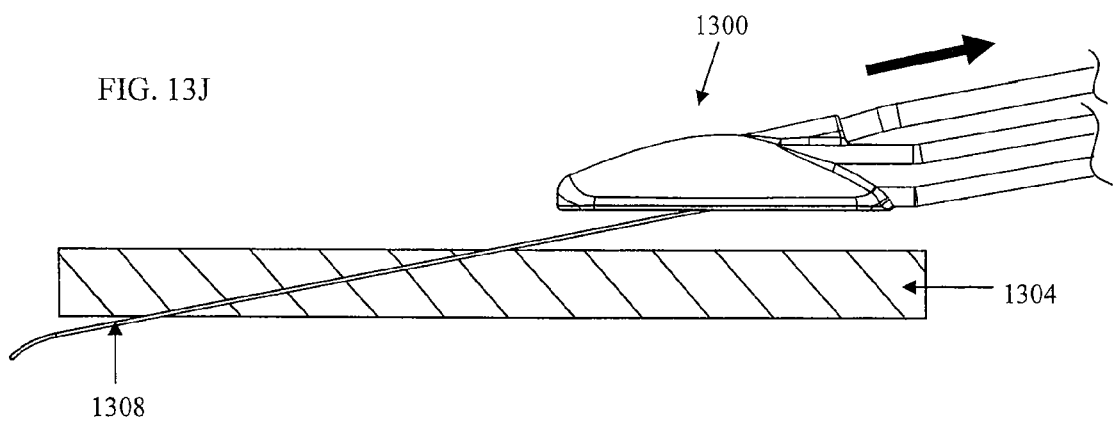
Figure 13K:
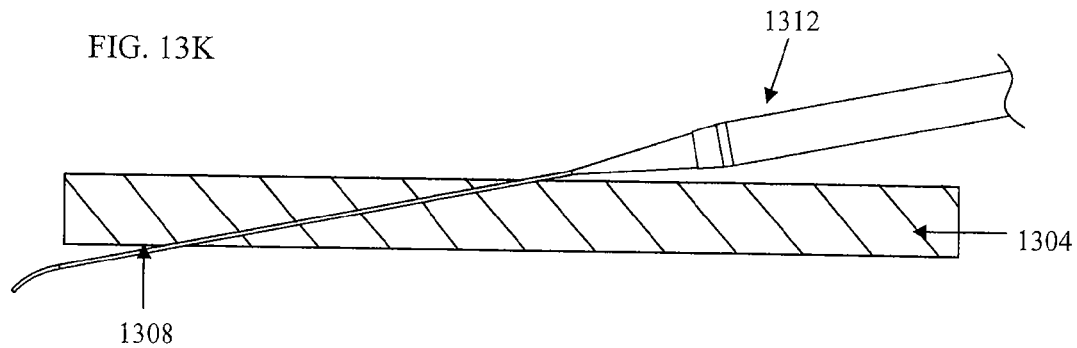
Figure 13L:
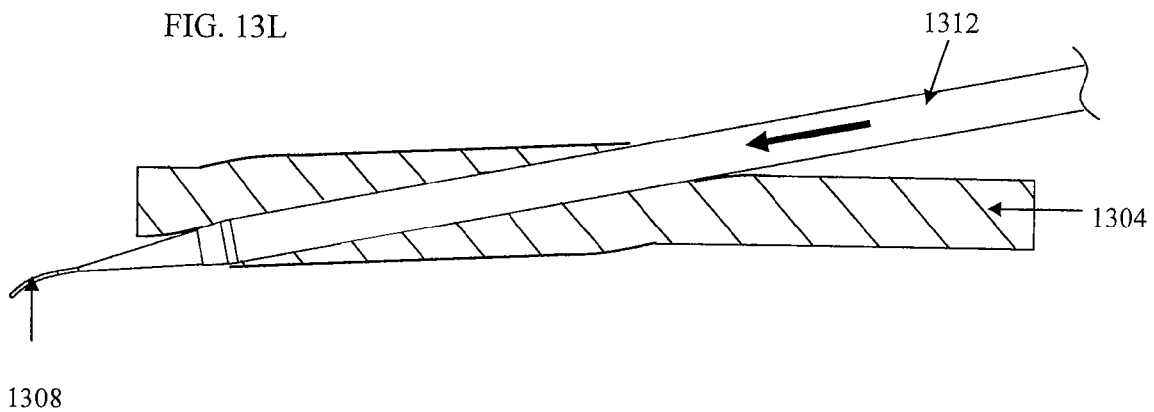
Figure 13M:
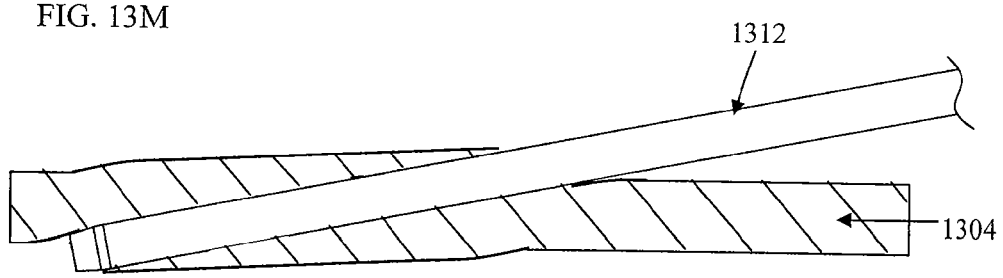

Turning back now to FIG. 13I, after the guide wire (1308) has been advanced through tissue (via a lumen in the tissue-piercing member for example), the tissue-piercing member (1306) may be withdrawn. Suction may be turned off, if desired, and the device may be withdrawn proximally, as shown in FIG. 13J. One or more dilators (or a single step-up dilator) or introducers (1312) may then be advanced over the guide wire (1308) if necessary to expand the tissue tract. Once sufficient access to the target site has been obtained, the guide wire (1308) may be withdrawn, as shown in FIGS. 13K-13M. One or more additional tools may then be introduced through the introducer, to carry out any suitable procedure. In some variations, the method described just here is used to carry out an arteriotomy to provide access to the vasculature. Once all procedures have been performed, the tools and introducer may be removed, allowing the tract to self-seal. Of course, as described above, sealing of the tract may be facilitated or expedited by mechanical pressure, delivery of energy (RF, ultrasound, microwave, etc.), or the use of one or more agents or a closure device, a combination of the foregoing, or the like.

Figure 13N:
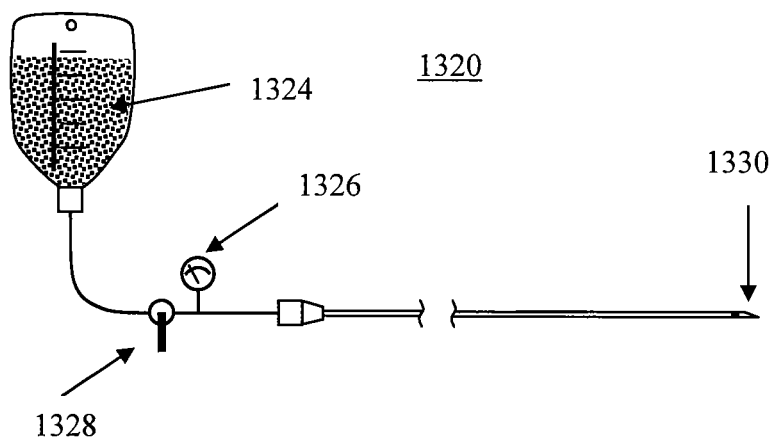
FIGS. 13N-13P depict one variation of a method for detecting a tissue location or boundary.
Figure 13O:
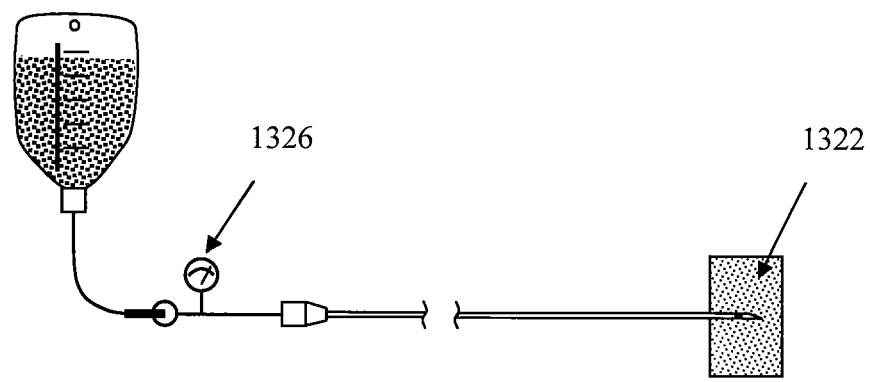
Figure 13P:
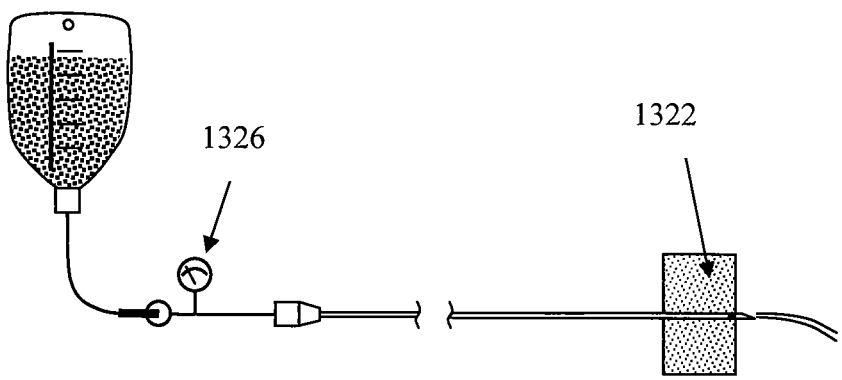

As briefly mentioned above, in some instances, it may be desirable to identify, detect, or otherwise locate one or more tissue surfaces or boundaries while employing the devices or methods described herein. FIG. 13N provides one illustrative system (1320) variation for detecting a tissue (1322) boundary or the like. Shown there is a pressurized fluid (1324), here in the form of fluid in a hanging IV bag, which is connected to tissue-piercing member (1330). In this variation, valve (1328) controls release of the pressurized fluid (1324), which may be saline, an antibiotic, a sterilizing agent, or any agent. Pressure is detected in this variation via gauge (1326). As the tissue-piercing member (1330) is advanced into tissue (1322), and while the tissue-piercing member (1330) is within tissue, the pressure should be relatively high, or higher than the initial pressure, as shown in FIG. 13O. Once the tissue-piercing member is advanced through the boundary of the tissue, the fluid may flow more freely through it, and the pressure should drop again, as depicted by FIG. 13P. Additionally, a radioopaque marker or band (e.g., in a distal region or at the tip of the tissue-piercing member) may be used to further verify tissue boundaries when the device is used with fluoroscopy. Of course, the viscosity of the fluid may be chosen to accommodate the size and length of the needle, in addition to other factors. Similarly, while pressure in this variation is shown measured on the proximal end of the system, it may be measured at any desirable distance from the tissue-piercing member tip. In some variations, for example, it might be desirable to measure fluid pressure close to the tissue-piercing member tip.

Figure 14A:
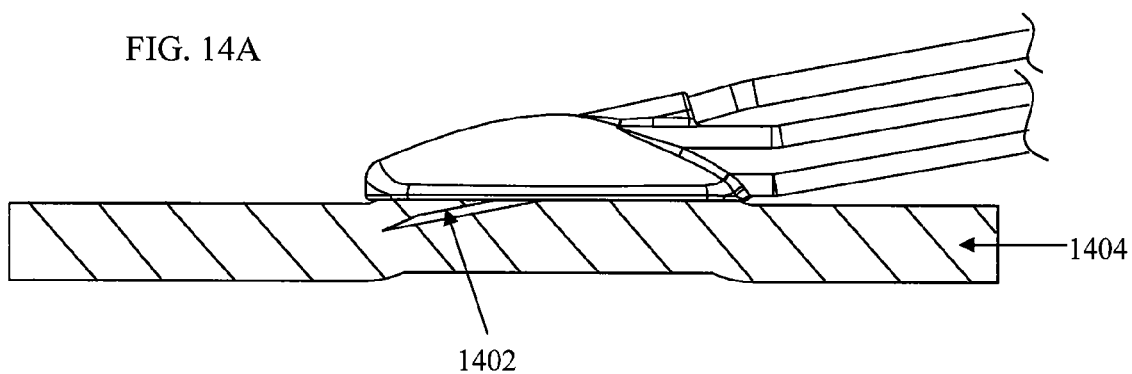
FIGS. 14A-14C depict another illustrative method for forming a tract in or through tissue, here where the device is articulated to redirect the tissue-piercing member.
Figure 14B:
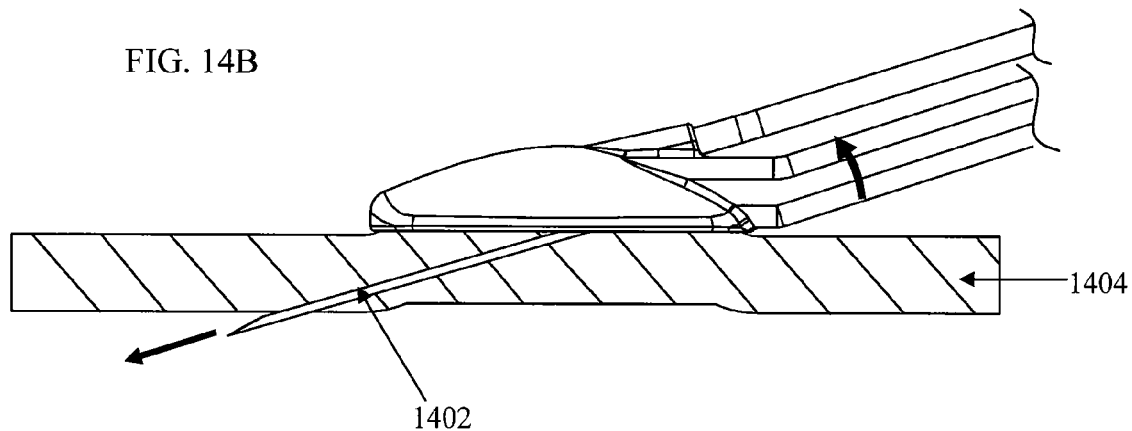
Figure 14C:
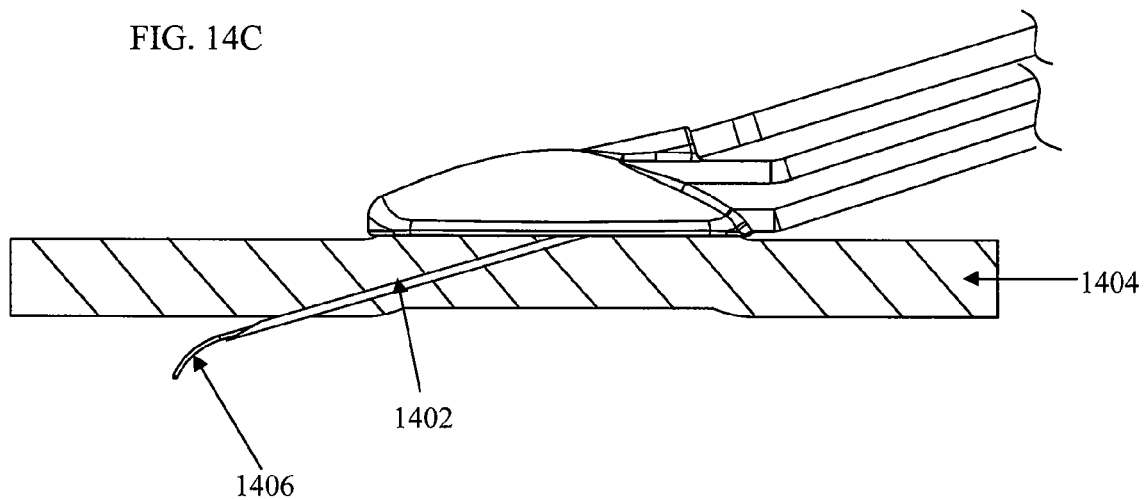

FIGS. 14A-14C depict another method for forming a tract in tissue. In this variation, once the tissue-piercing member (1402) has been advanced into tissue (1404), the device (1400) may be articulated to redirect the tissue-piercing member (1402). The tissue-piercing member (1402) may then be advanced through the tissue (1404) in the repositioned direction. Similar to the method described just above, a guide wire (1406) may then be advanced through the tissue tract (via a lumen in the tissue-piercing member, for example), and one or more introducers may then be advanced over the guide wire (1406) for facilitating passage of tools therethrough.

Of course, it should be understood that the suction member may be articulated, the elongate member may be articulated, the suction member may be rotated to rotate the tissue prior to advancing a tissue-piercing member therethrough, and the like. Indeed, any of the methods of manipulating tissue described in U.S. patent application Ser. No. 11/873,957, which application is hereby incorporated by reference in its entirety, may be used here.

Figure 15A:
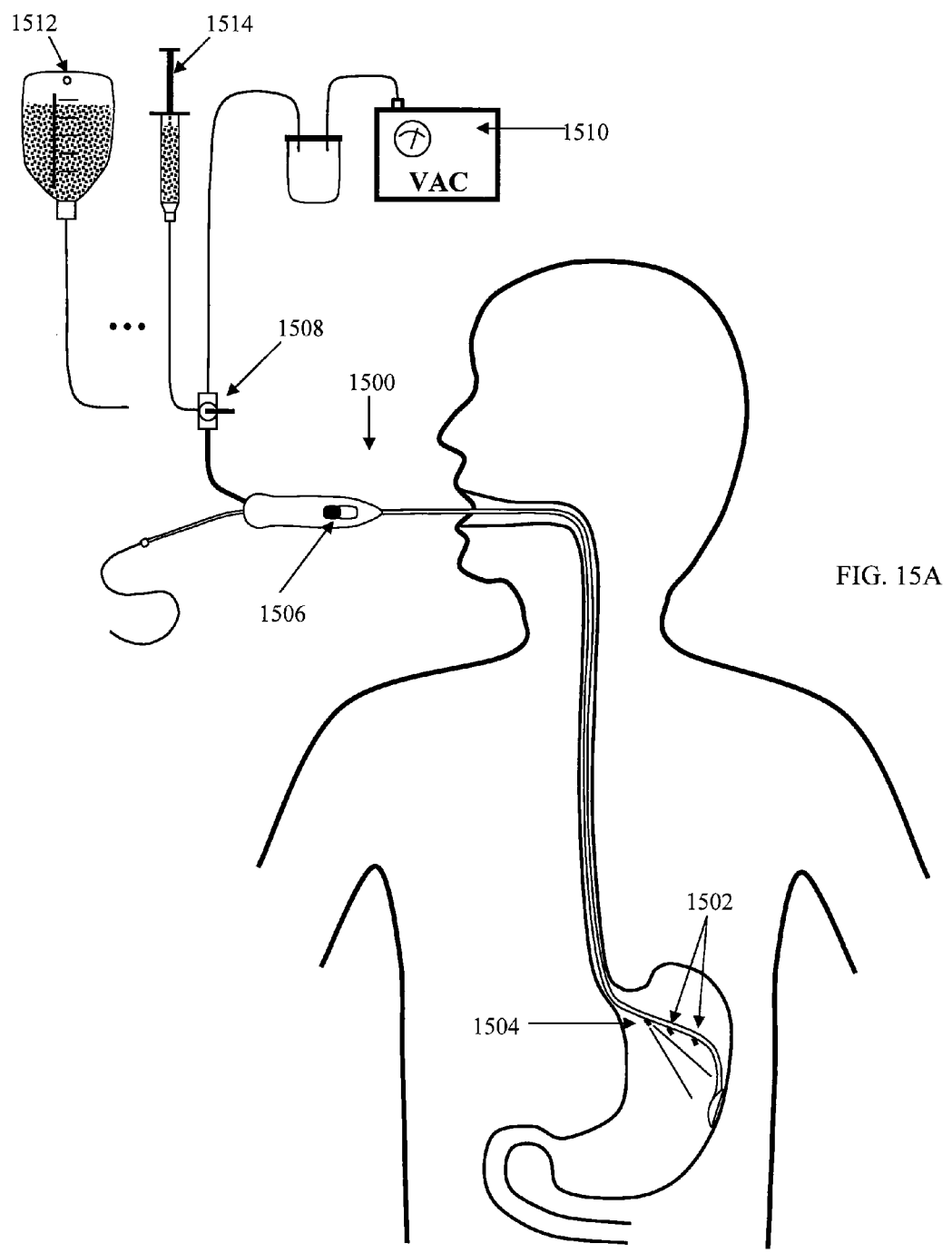
FIG. 15A is an overview illustration of how the devices described herein may advanced through a natural body orifice and used to form a tract in or through tissue, in this case, the stomach.

FIG. 15A is an overview illustration of how the devices described herein may be used to form tracts in tissue within or through the stomach, or stomach tissue. In this variation, the device is not used with a separate gastroscope, and here visualization is enabled by a series of cameras or other visualization devices (1502) in combination with light or illumination source (1504). This particular method may be quite useful, for example, in natural orifice transluminal endoscopic surgeries. FIG. 15A also details an illustrative proximal control of the device (1500), here in the form of a slide actuator (1506). The slide actuator (1506) may be used, for example, to advance and retract the tissue-piercing member, may be used to turn on and off one or more visualization devices (1502), may be used to turn on and off the illumination source (1504), or some combination thereof. Of course, the device (1500) may include any number and type of proximal controls (slides, switches, buttons, etc.) to control any number or combination of functions (e.g., vacuum, visualization, actuation of tissue-piercing member, illumination, fluid flush, etc.).

Also shown in FIG. 15A is the illustrative use of suction, fluid injection, and the like. Here, a three-way valve (1508) is shown, which connects to and helps control use of vacuum (1510), bag infuser (1512), and syringe injector (1514). That is, the three-way valve (1508) may be toggled between its various positions to turn off or on the vacuum, or fluid (via bag infuser or syringe injection). Having the ability to turn on and off the vacuum, for example, may be particularly useful in instances where the device has become stuck on or against one or more tissue surfaces. Turning on and off fluid injection or delivery, for example, may be particularly useful when it is desirable to flush, irrigate, unclog, or deliver one or more substances to the tissue. Of course, the control depicted in FIG. 15A is just one way to control or operate the described functions. It should be understood that any suitable configuration (having a two-way valve to control certain features, but not others, having additional proximal controls, combinations of the foregoing, and the like) may be used.

Figure 15B:
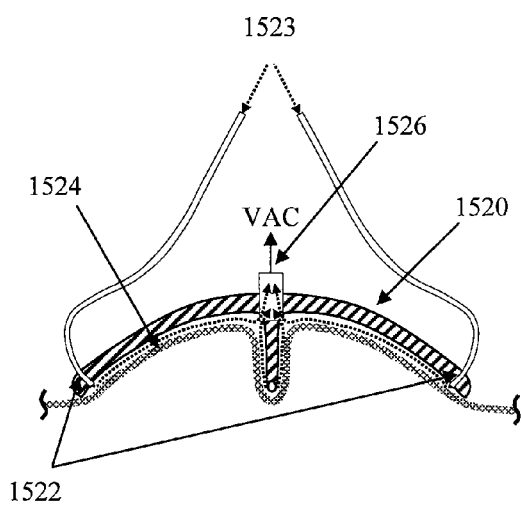
FIGS. 15B and 15C provide illustrative variations of fluid delivery and collection configurations.
Figure 15C:
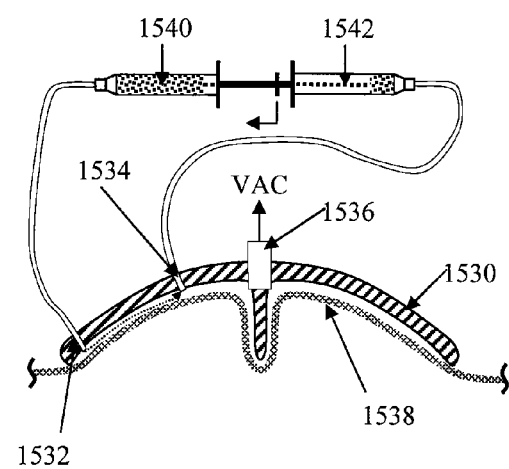

FIGS. 15B and 15C schematically represent variations where one or more fluids (therapeutic, flushing, sterilizing, etc.) are delivered to the tissue (1524) while the suction member (1520) is still under vacuum. For example, FIG. 15B depicts a suction member (1520) having one or more peripheral ports (1522) thereon or therealong for delivery or passage of one or more fluids therethrough (shown by arrows 1523). In this variation, fluids may be injected or delivered through the one or more peripheral (1522) or other ports (e.g., needle port, traction member port, etc.), and then collected through a vacuum port (1526) while the tissue (1524) remains captured by suction. The suction member of FIG. 9J, for example, may be useful in performing this method. FIG. 15C depicts an alternative variation where the fluid is not collected through a vacuum port (1536). Shown there is suction member (1530) having one or more peripheral ports (1532) thereon or therealong for delivering one or more fluids (e.g., therapeutic, flushing, sterilizing, etc.) to tissue (1538). In this variation, the fluid is injected through a first syringe (1540) or other delivery system, and is collected by a separate second syringe (1542) or other suitable collection system, so that the vacuum port (1536) need not function to collect fluid. The push pull syringe of this variation may, for example, help prevent the vacuum from emptying syringe contents.

Figure 15D:
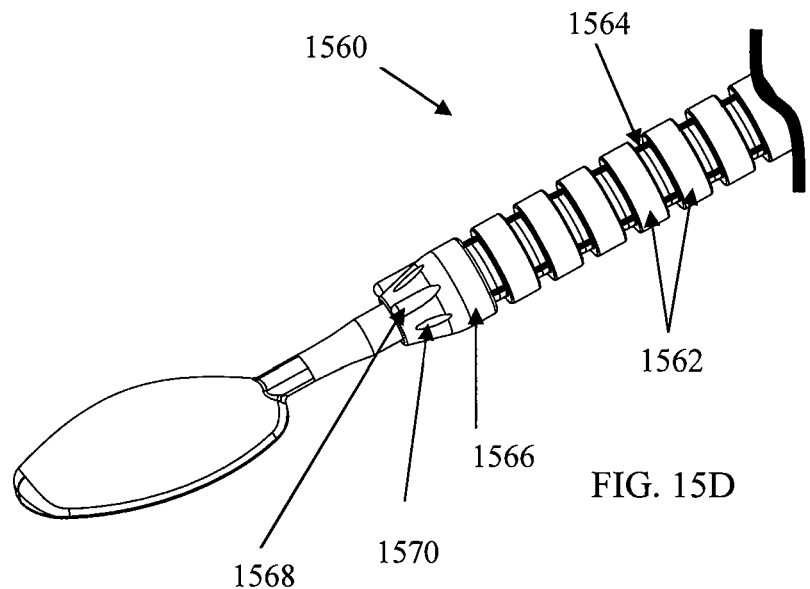
FIGS. 15D and 15E provide an illustrative depiction of an articulatable elongate member.
Figure 15E:
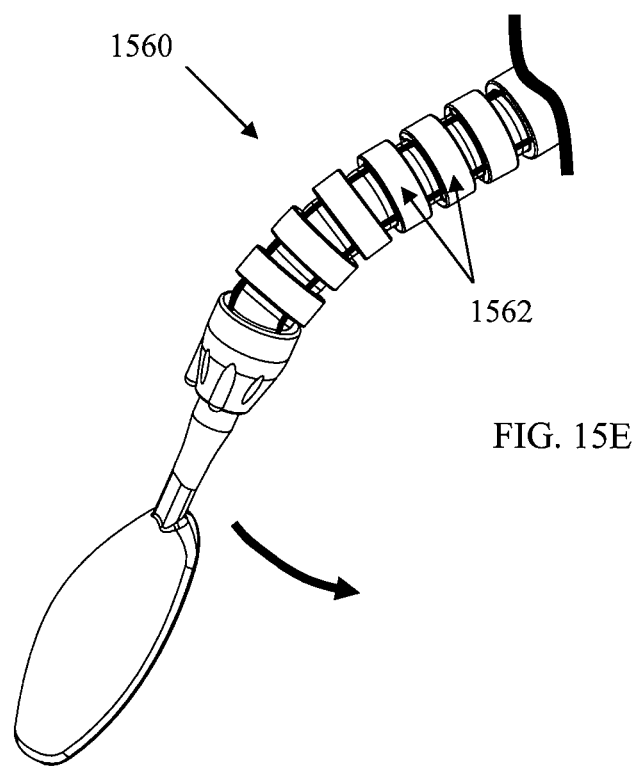

FIGS. 15D and 15E provide depictions of articulatable elongate members that may be used in connection with any of the devices and methods described here, shown in an unarticulated and articulated state respectively. The elongate member (1560) in these variations may comprise a series of links (1562) connected via a series of wires or cables (1564). Also shown in these figures is distal-most link (1566), comprising two discrete sets of features (1568, 1570). The features may be any of the features described above, and in one variation, features (1568) are cameras while features (1570) are illumination sources. Any combination, location, and number of features may be used as described above. Having the features located on or about the distal-most link (1566) is just one illustrative variation of a suitable location. It should also be understood that the individual links of the elongate member (1560) need not be exposed. The elongate member (1560) may be sheathed or otherwise covered. In addition, the elongate member of these variations, as with all the described device variations may be robotically or remotely controlled.

Figure 15F:
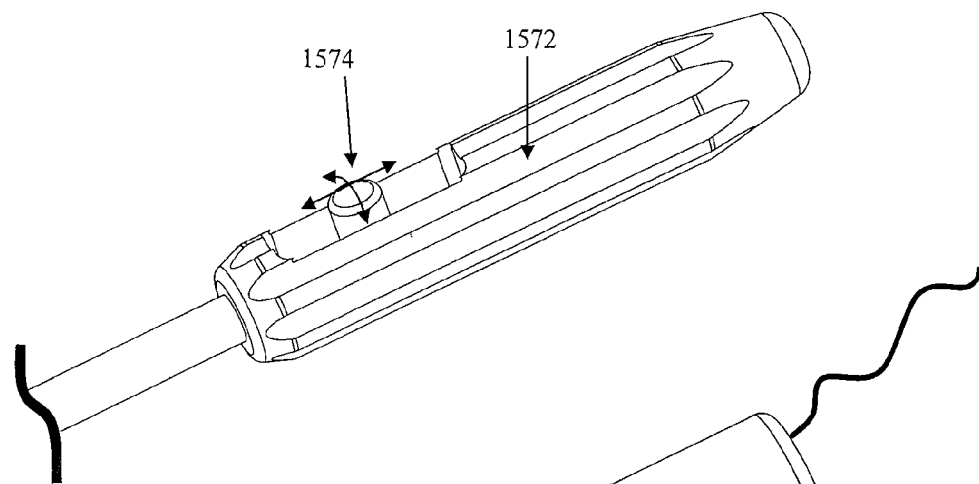
FIGS. 15F and 15G depict illustrative handles for use with the devices described herein.
Figure 15G:
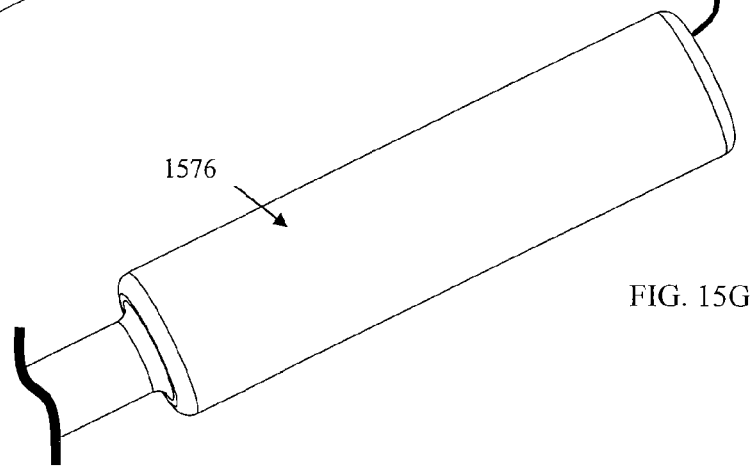

FIGS. 15F and 15G depict various handles or proximal controls for use with any of the described devices. Specifically, FIG. 15F depicts handle (1572) having a joystick type control (1574). In this variation, the joystick type control (1574) may be used to control movement of the elongate member in a way that corresponds to movement of the control (1574) itself. For example, movement of the control (1574) in a forward direction may effect movement of an elongate member in a forward direction. Similarly, movement of the control (1574) to the right may effect movement of an elongate member to the right, and so forth. This type of control may be particularly useful when it is desirable to have intuitive control of the device, which may help with user adoption and ease of use. FIG. 15G depicts another handle (1576) where all controls are enclosed therein. For example, handle (1576) may house one or more motors, linear actuators, pneumatic cylinders, or other electronic features. This type of handle (1576) may be particularly useful as a robotic interface.

Figure 15H:
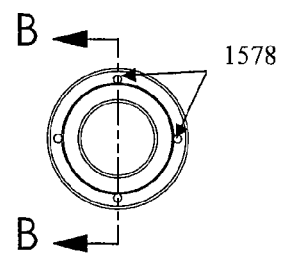
FIGS. 15H and 15I depict illustrative cross-sectional views of portions of illustrative elongate members.
Figure 15I:
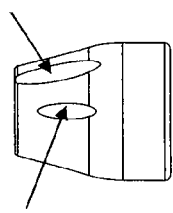
Figure 15I:
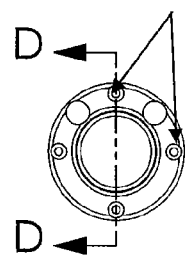

FIGS. 15H and 15I depict cross-sectional and perspective views of illustrative distal-most links in connection with the articulatable devices described above. The link of FIG. 15H is shown without having additional features. Shown there are through-lumens or apertures (1578) for passage of one or more wires or cables therethrough. The link of FIG. 15I is shown having one or more additional features, for example, like the distal-most link (1566) described just above with reference to FIGS. 15D and 15E. Shown in this variation, are discrete features (1582) and (1584), which may be cameras and illumination sources, as described just above, or any other described feature. Also shown in cross-sectional view are through-lumens (1580) for passage of connecting cables or wires.

Figure 16A:
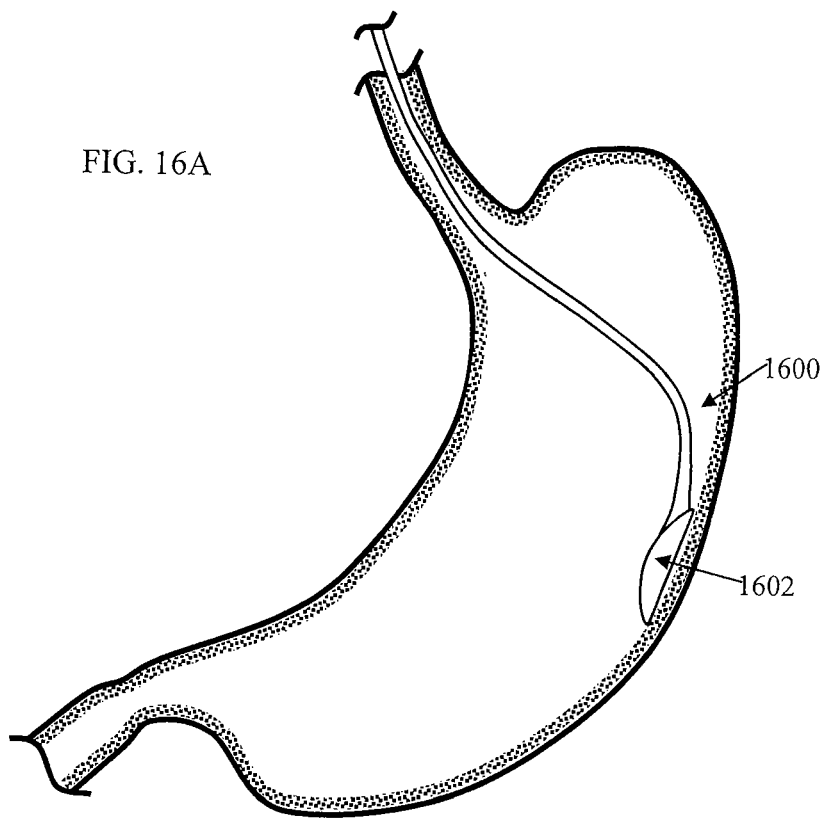
FIGS. 16A-16I depict an illustrative method for forming a tract in or through stomach tissue.
Figure 16B:
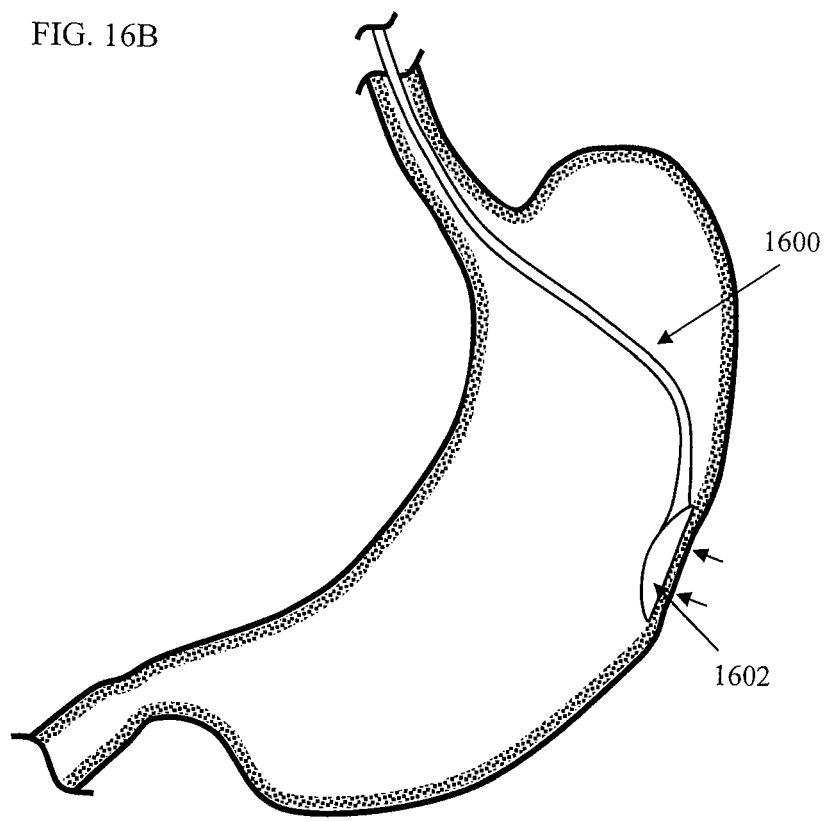
Figure 16C:
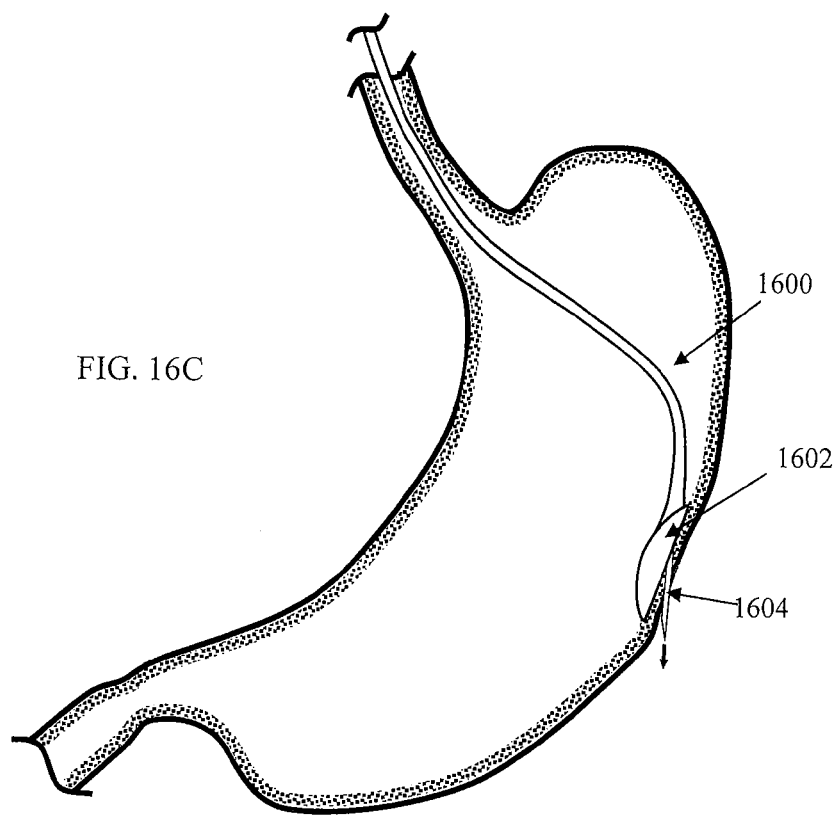

FIGS. 16A-I depict a method of forming a tract in or through stomach tissue. It should be understood that just the distal portion of the device is shown in these figures, and that this method may be used to form tissue tracts as depicted, whether or not the device is a stand alone device, or is used with a gastroscope or advanced through some other sheathed structure (including instances where the device is back-loaded into the working channel of any type of gastroscope, endoscope, laparoscope, etc., with or without steering, visualization, illumination, etc.). Turning now to FIG. 16A, the device (1600) comprising a suction member (1602) is shown advanced adjacent to tissue, here stomach tissue. In FIG. 16B, vacuum or suction has been turned on, and tissue is drawn against, or pulled into, the suction member (1602) as indicated by the arrows in that figure. Next, a tissue-piercing member (1604) (e.g., a needle or other tissue-piercing cannula) is advanced from the device and through the drawn tissue to form a tract in the tissue as shown in FIG. 16C.

Figure 16D:
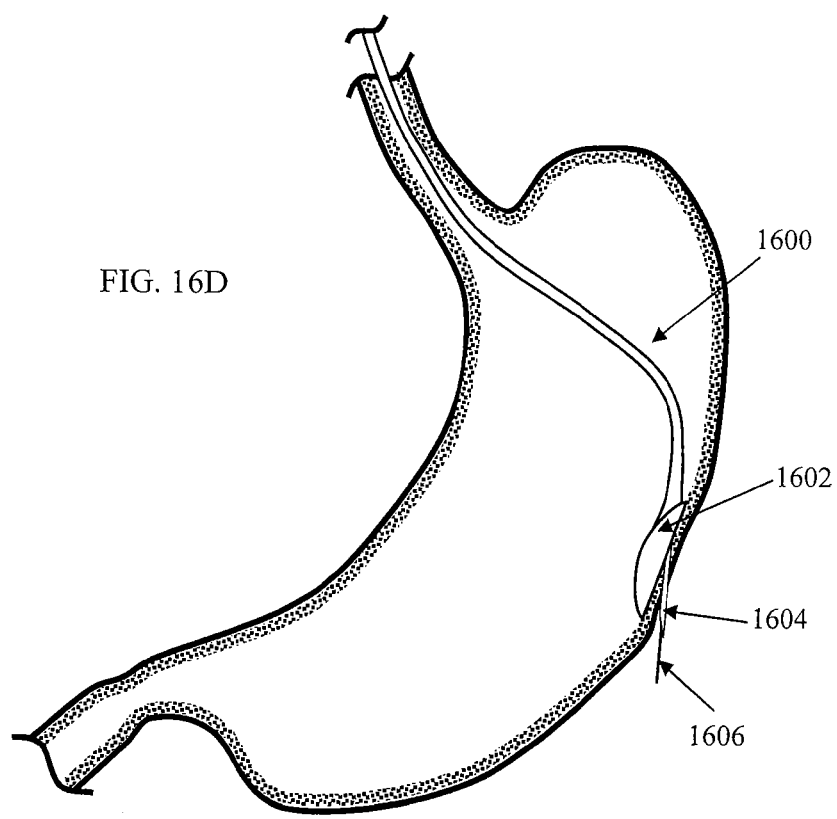
Figure 16E:
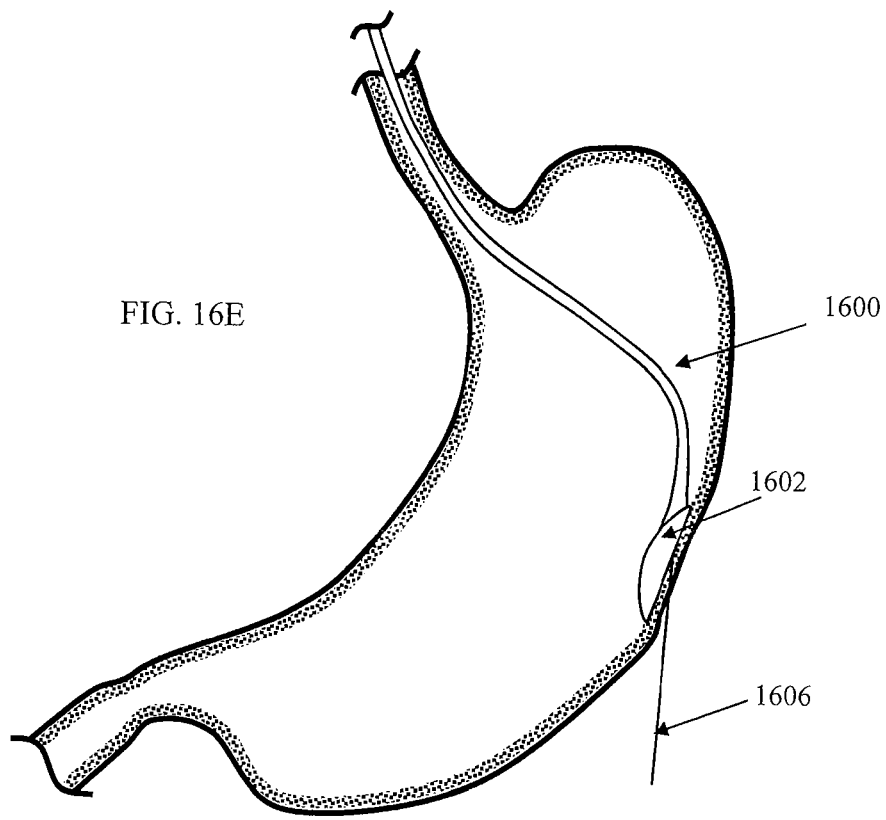
Figure 16F:
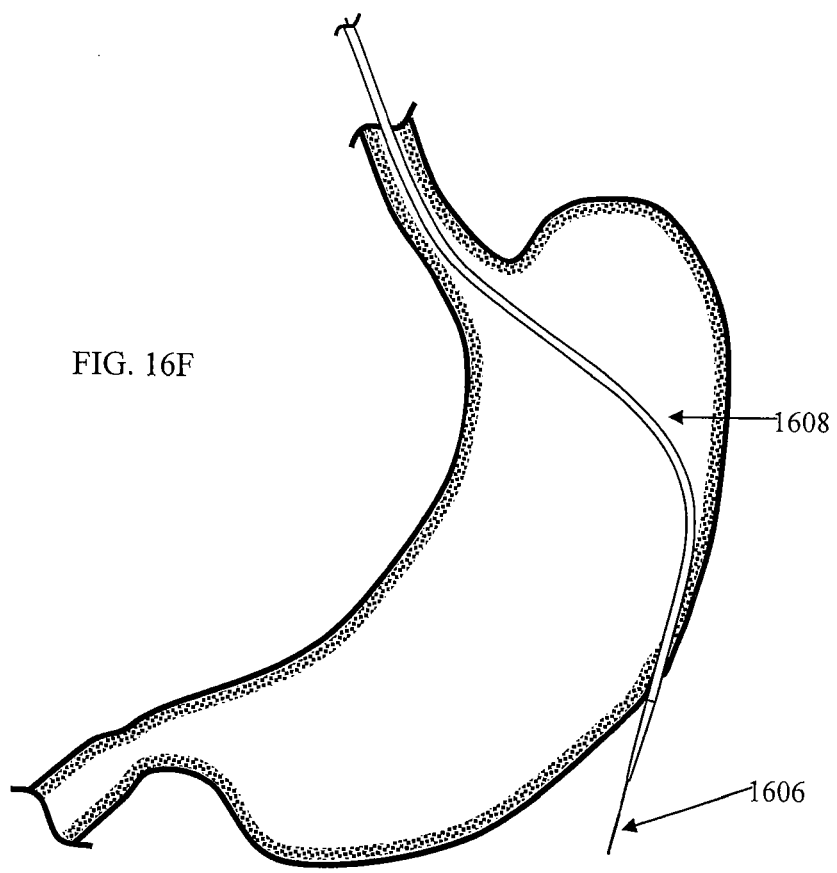
Figure 16G:
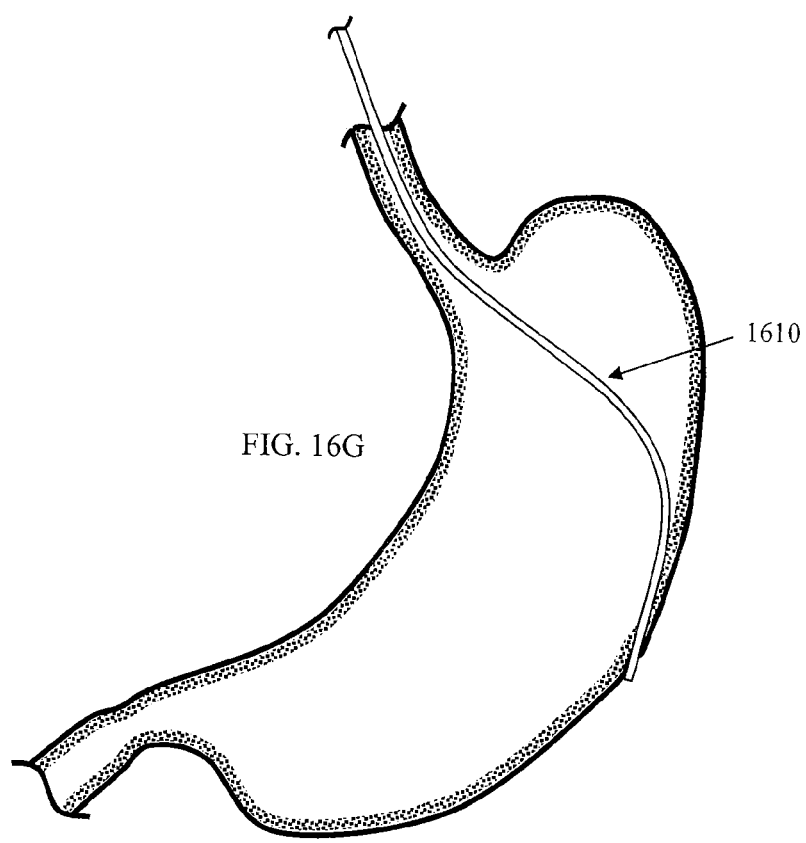
Figure 16H:
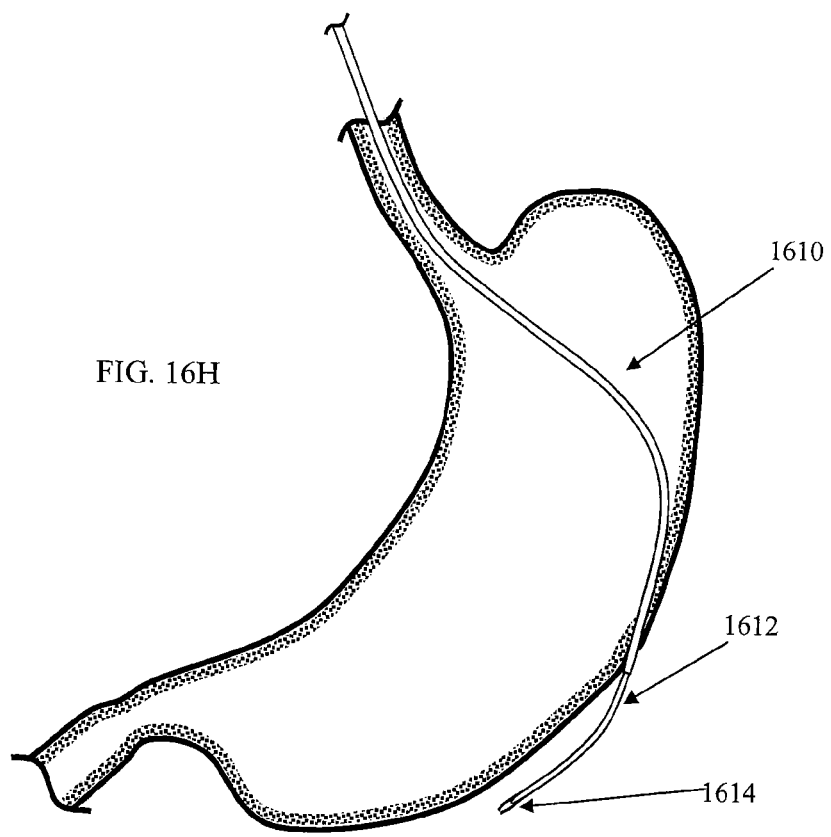
Figure 16I:
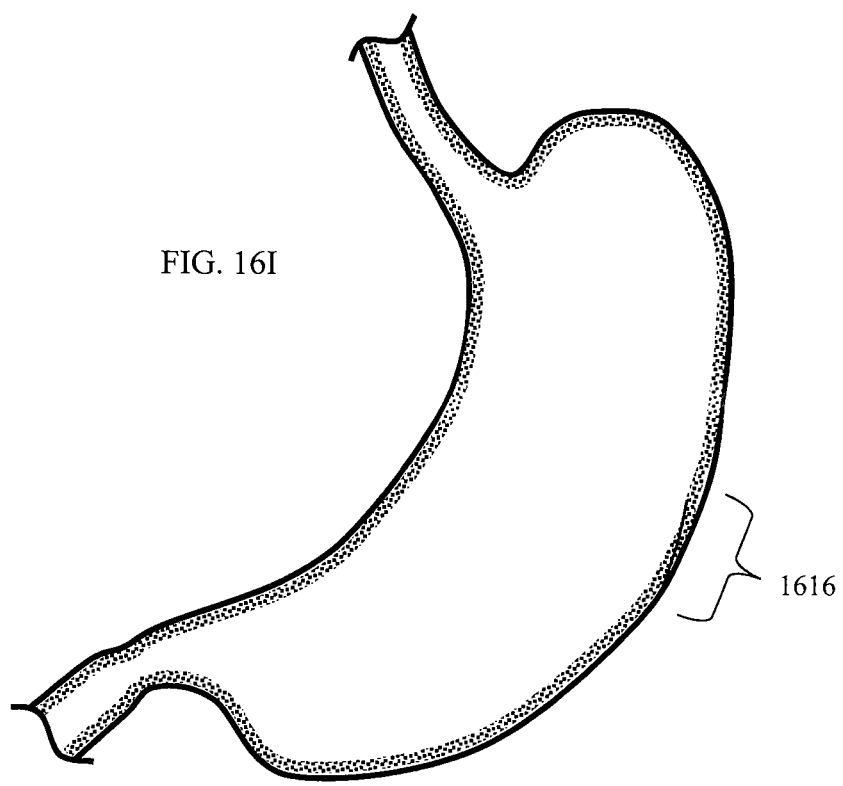
Figure 17A:
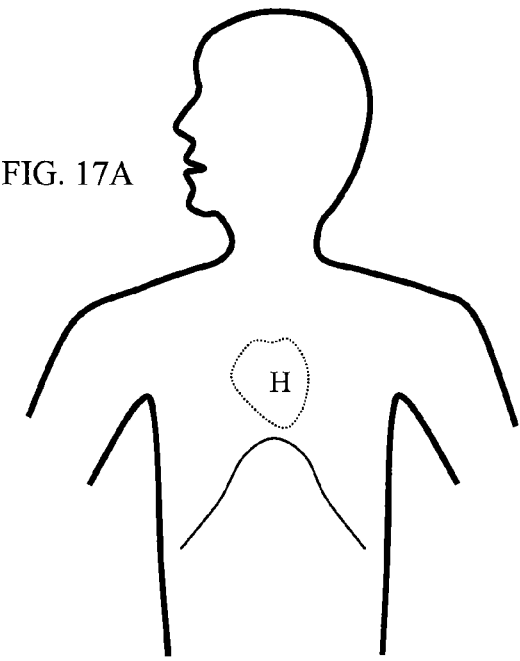
FIGS. 17A-17D depict an illustrative method of accessing the pericardial space in connection with the methods described herein.
Figure 17B:
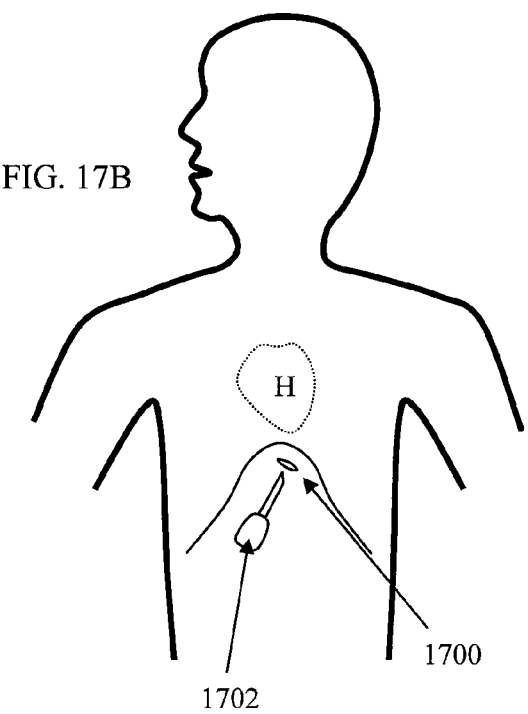
Figure 17C:
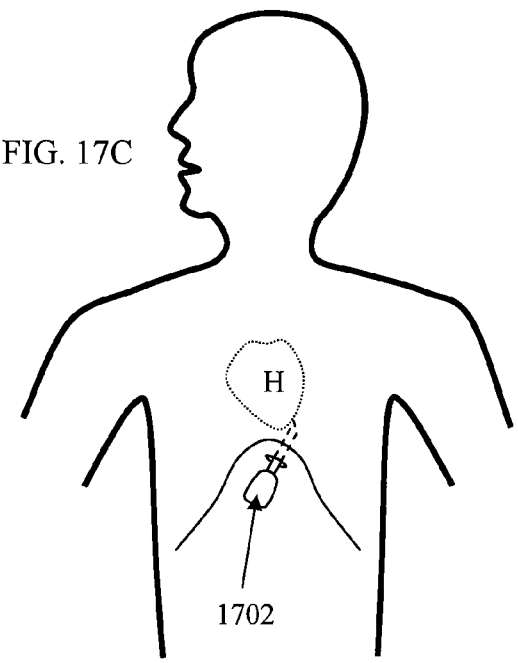
Figure 17D:
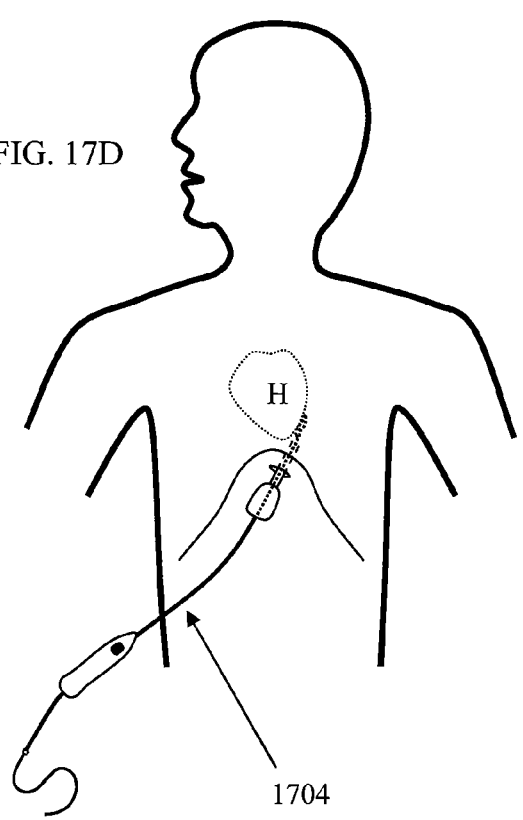

Once the tract has been formed, a guide wire (1606), guide element, or the like may be advanced through the tract (e.g., by advancing through a lumen in the tissue-piercing member), as shown in FIG. 16D, and the tissue-piercing element (1604) is withdrawn as shown in FIG. 16E. A stepped-up dilator (1608) or series of dilators (not shown) may then be advanced over the guide wire (1606) as shown in FIG. 16F. In this way, for example, the cross-sectional area of the tract may be expanded or enlarged. After the tract has been expanded, an introducer (1610), which may be part of the dilator (1608) can be left in place and used as a conduit for introducing additional tools through the tract, as shown in FIG. 16G. FIG. 16H shows one illustrative method where a tool (1612) having an end effector, e.g., grippers (1614) has been advanced through introducer (1610) for use in a procedure. Any number or type of tools may be advanced through the introducer in this way. After the procedure has been performed, the tools and introducer are removed leaving tract (1616) to self-seal. Of course, sealing may be enhanced any suitable additional mechanism (e.g., via mechanical pressure, via ultrasound, via one or more closure devices, and the like).

FIG. 17A-17D depict one method of advancing a device described herein into the pericardial space in order to form a tract through tissue of the heart (H). As shown in those figures, an incision (1700) may be made (e.g., sub-xyphoid, etc.) and a port (1702) placed therethrough to provide for suitable delivery or exchange of tools therethrough. Once the port (1702) has been placed, any of the devices (1704) described here may be placed through the port (1702) to form a tract in or through tissue of the heart (H), as will be described in more detail with reference to FIGS. 18A-18K.

Figure 18A:
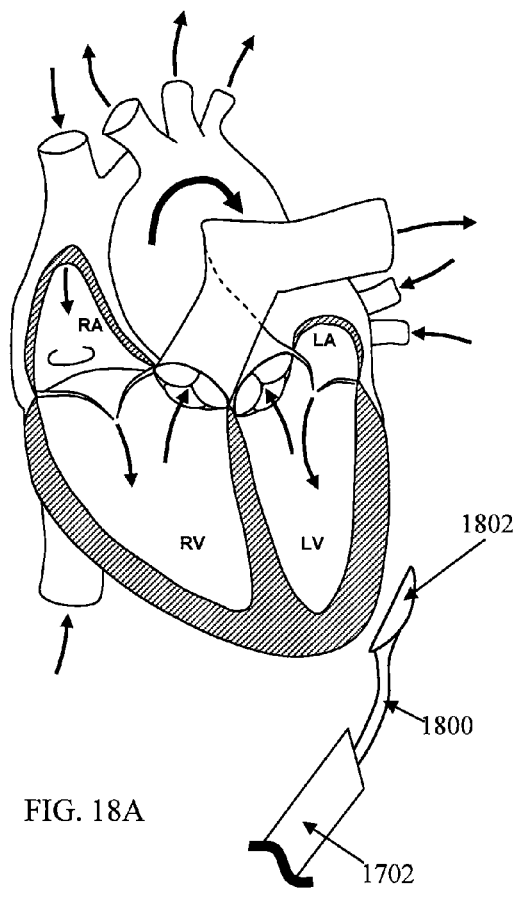
FIGS. 18A-18K depict an illustrative method for forming a tract in or through heart tissue.
Figure 18B:
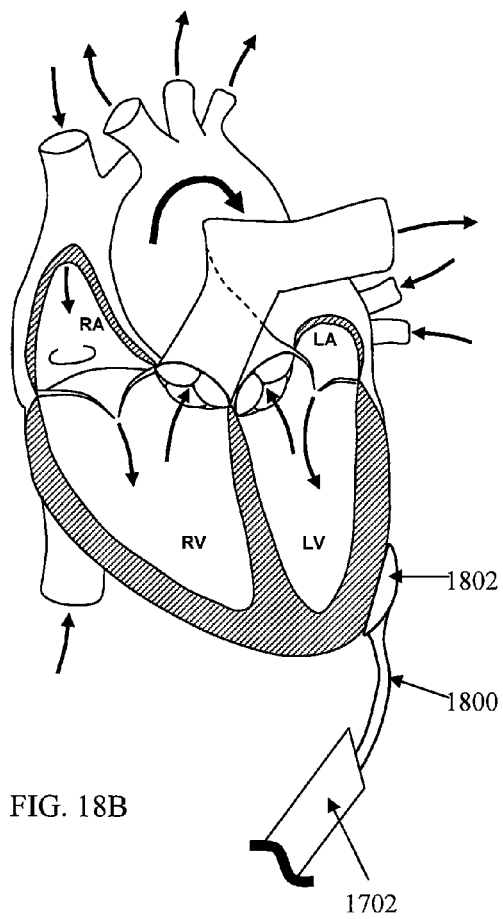
Figure 18C:
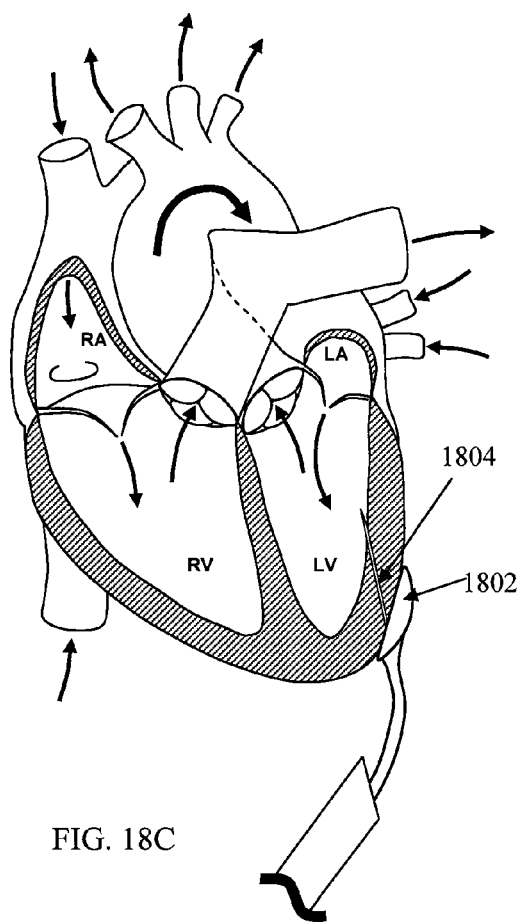
Figure 18D:
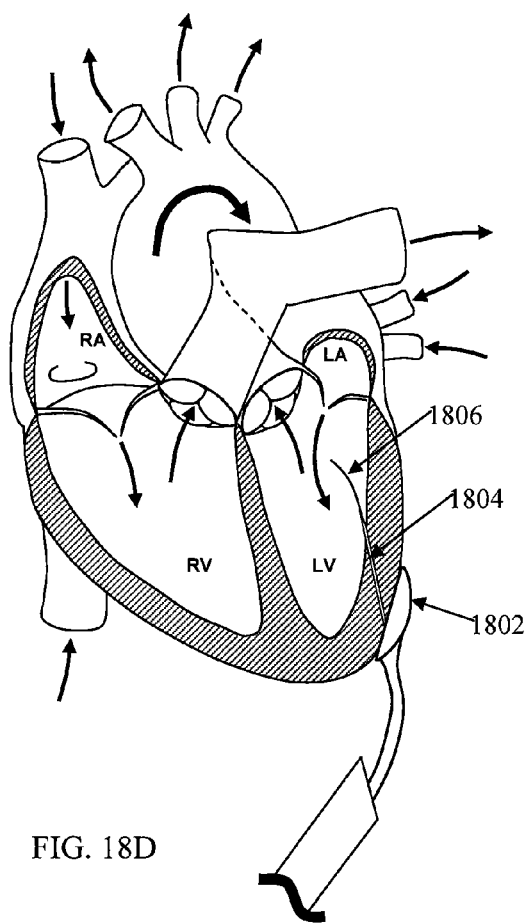
Figure 18E:
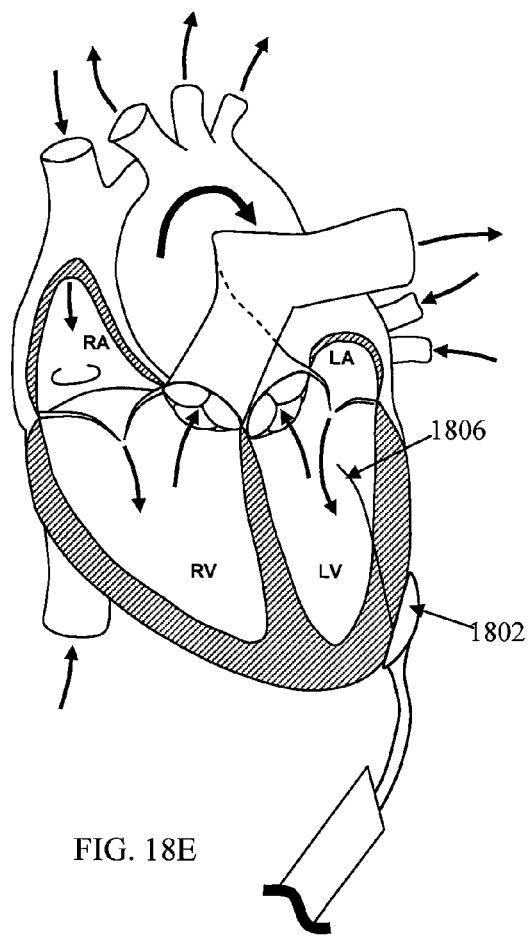
Figure 18F:
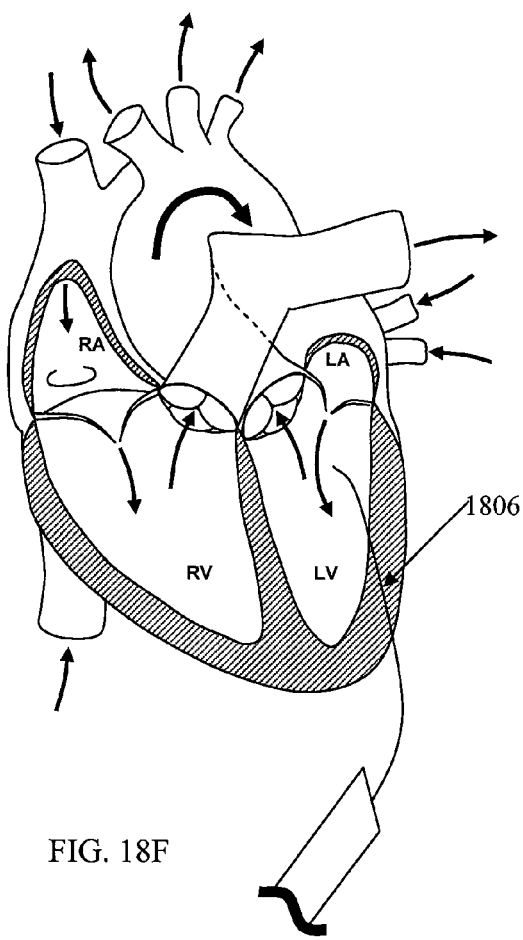

Turning to FIG. 18A, a device (1800) comprising a suction member (1802) is advanced adjacent to heart tissue. The device may be advanced adjacent to heart tissue in any suitable fashion, e.g., through port (1702) described above. Vacuum or suction may then be applied to draw heart tissue against or into suction member (1802) as shown in FIG. 18B. A tissue-piercing member (1804) may then be advanced from the device (e.g., through the suction member) and through the drawn tissue to form a tissue tract as shown in FIG. 18C. A guide wire (1806) or other suitable such guide element may then be advanced through the tract, e.g., by advancing through a lumen in the tissue-piercing member (1804), as shown in FIG. 18D. The tissue-piercing member (1804) and device (1800) may then be removed, as shown by FIGS. 18E and 18F respectively.

Figure 18G:
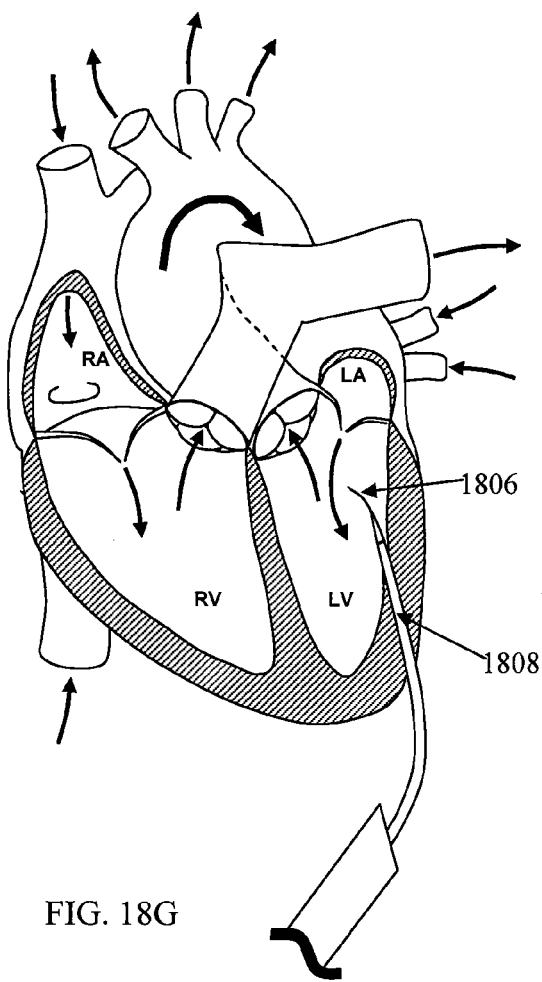
Figure 18H:
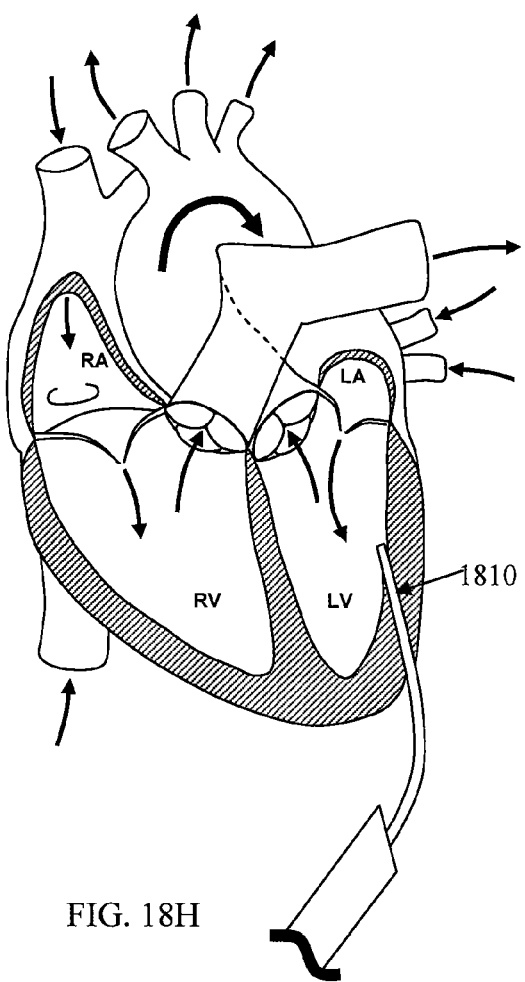
Figure 18I:
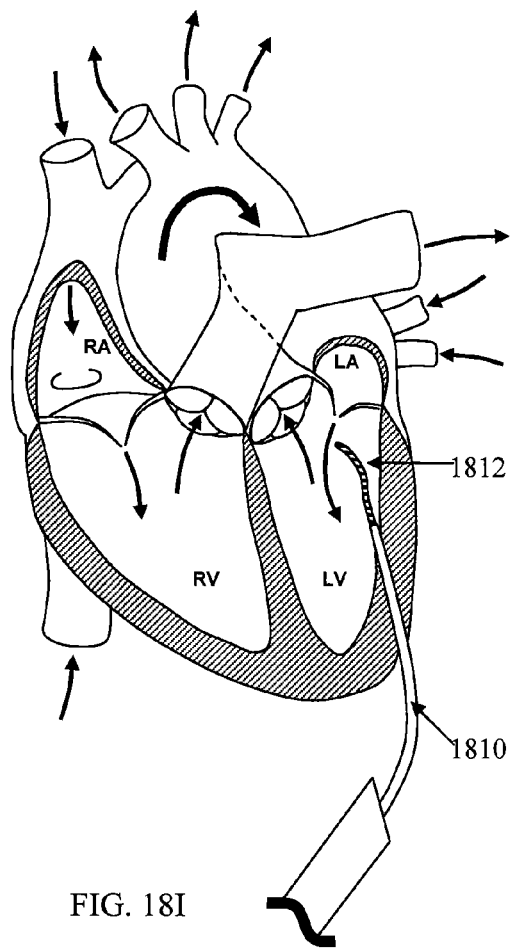
Figure 18J:
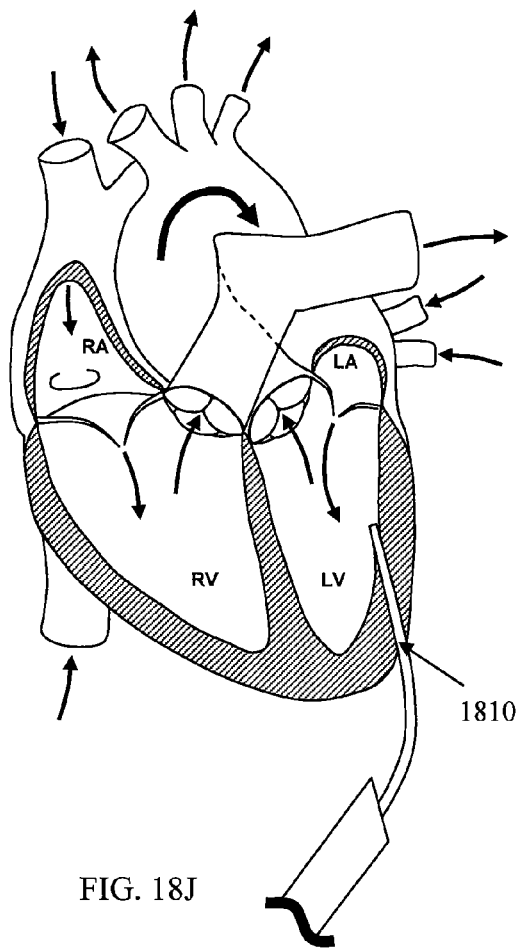
Figure 18K:
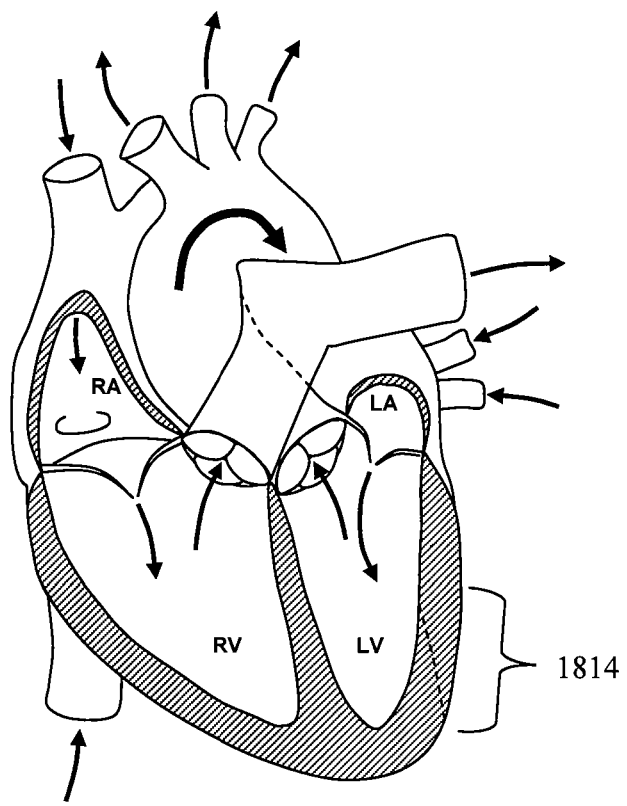

A stepped-up dilator (1808) or series of dilators (not shown) may then be advanced over the guide wire (1806) as shown in FIG. 18G. In this way, for example, the cross-sectional area of the tract may be expanded or enlarged. After the tract has been expanded, an introducer (1810), which may be part of the dilator (1808) can be left in place and used as a conduit for introducing additional tools through the tract, as shown in FIG. 18H. FIG. 18I shows one illustrative method where a tool (1812) has been advanced through introducer (1810) for use in a procedure. Here left ventricular access has been accomplished, and therefore, use of these methods in conjunction with repair or replacement of the aortic or mitral valve may find particular utility. Any number or type of tools may be advanced through the introducer in this way. After the procedure has been performed, the tools and introducer are removed leaving tract (1814) to self-seal, as shown by FIGS. 18J and 18K. Of course, sealing may be enhanced by any suitable additional mechanism (e.g., via mechanical pressure, via ultrasound, via one or more closure devices, and the like).

III. Kits

Kits are also described here. In some variations, the kits include a device for forming a tract through tissue, where the device comprises one or more suction members as described above, and one or more additional tools. For example, the tools may be those that are advanced through the tract during the performance of a procedure (e.g., guide wires, scissors, grippers, ligation instruments, etc.), one or more supplemental tools for aiding in closure (e.g., an energy delivering device, a closure device, and the like), one or more tools for aiding in the procedure (e.g., gastroscope, endoscope, cameras, light sources, etc.), combinations thereof, and the like. Of course, instructions for use may also be provided with the kits.

What we claimed is:

1. A device for forming a tract in tissue comprising:
   an elongate member;
   a suction member coupled to a distal portion of the elongate member, the suction member defining a basal surface and an underside surface, the underside surface configured to support an adjacent tissue portion as the adjacent tissue portion is drawn against the underside surface by a suction load which may be applied to the suction member; and
   a tissue-piercing member slidably housed within the elongate member and configured to create a tract in across the adjacent tissue portion to accommodate passage of one or more tools for conducting a procedure through the tract, wherein the tissue-piercing member is configured to be advanced across at least a portion of the adjacent tissue portion such that the tract created is a self-sealing tract that generally seals without supplemental closure devices after the one or more tools have been withdrawn from the tract.

2. The device of claim 1, wherein the elongate member is flexible.

3. The device of claim 1, wherein the suction member is coupled to the elongate member via a flexible portion.

4. The device of claim 3, wherein the flexible portion is a hinge.

5. The device of claim 1, wherein the elongate member is articulatable.

6. The device of claim 1, wherein the tissue-piercing member is articulatable.

7. The device of claim 1, wherein the suction member is articulatable.

8. The device of claim 1, wherein the suction member has one or more tissue apposition members thereon.

9. The device of claim 8, wherein the tissue apposition member is a rib.

10. The device of claim 1, further comprising one or more sensors.

11. The device of claim 1, wherein the tissue-piercing member is a needle.

12. The device of claim 11, wherein the needle is hollow.

13. The device of claim 1, wherein the suction member is connected to a vacuum source.

14. The device of claim 1, wherein the elongate member has one or more lumens therethrough.

* * * * *